US008361638B2

(12) United States Patent
Stoessel et al.

(10) Patent No.: US 8,361,638 B2
(45) Date of Patent: Jan. 29, 2013

(54) FLUORINE DERIVATIVES FOR ORGANIC ELECTROLUMINESCENCE DEVICES

(75) Inventors: Philipp Stoessel, Frankfurt am Main (DE); Holger Heil, Frankfurt am Main (DE); Dominik Joosten, Frankfurt am Main (DE); Christof Pflumm, Frankfurt am Main (DE); Anja Gerhard, Egelsbach (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 12/936,644

(22) PCT Filed: Mar. 11, 2009

(86) PCT No.: PCT/EP2009/001736

§ 371 (c)(1),
(2), (4) Date: Oct. 6, 2010

(87) PCT Pub. No.: WO2009/124627

PCT Pub. Date: Oct. 15, 2009

(65) Prior Publication Data

US 2011/0037027 A1 Feb. 17, 2011

(30) Foreign Application Priority Data

Apr. 7, 2008 (DE) ......................... 10 2008 017 591

(51) Int. Cl.
*H01L 51/54* (2006.01)

(52) U.S. Cl. ........ 428/690; 428/917; 313/504; 313/505; 313/506; 257/40; 257/E61.05; 257/E51.026; 257/E51.032; 544/234; 546/18; 546/79

(58) Field of Classification Search .................. 428/690, 428/917; 313/504, 505, 506; 257/40, E51.05, 257/E51.026, E51.032; 544/234; 546/18, 546/79

See application file for complete search history.

(56) References Cited

U.S. PATENT DOCUMENTS

| | | | |
|---|---|---|---|
| 5,007,945 A | 4/1991 | Tien et al. | |
| 5,176,977 A | 1/1993 | Molaire et al. | |
| 5,232,471 A | 8/1993 | Chen et al. | |
| 5,447,960 A | 9/1995 | Sinnott et al. | |
| 5,698,740 A * | 12/1997 | Enokida et al. | 564/308 |
| 2003/0162653 A1 | 8/2003 | Jeanes et al. | |
| 2004/0192848 A1 | 9/2004 | Angiolini et al. | |
| 2005/0209404 A1 | 9/2005 | Sakurai et al. | |
| 2007/0051944 A1 | 3/2007 | Vestweber et al. | |

FOREIGN PATENT DOCUMENTS

| | | | |
|---|---|---|---|
| EP | 0539778 | A1 | 5/1993 |
| EP | 1651013 | A1 | 4/2006 |
| EP | 1666970 | A1 | 6/2006 |
| JP | 9-80791 | A | 3/1997 |
| JP | 10-095972 | A | 4/1998 |
| JP | 11-255859 | A | 9/1999 |
| JP | 2005-085599 | A | 3/2005 |
| JP | 2005-272614 | A | 10/2005 |
| JP | 2006-89541 | A | 4/2006 |
| JP | 2007-49055 | A | 2/2007 |
| WO | WO-94/04250 | A1 | 3/1994 |
| WO | WO-98/02379 | A2 | 1/1998 |
| WO | WO-2005/053055 | A1 | 6/2005 |
| WO | WO-2006/033554 | A1 | 3/2006 |

OTHER PUBLICATIONS

Database: Beilstein, Accession No. 8563317, Jan. 2009. XP-002527926.

Tarbell, D.S., et al., "The Synthesis of 9-Phenanthrylmethyldichlorophenol and Related Compounds," *J. Am. Chem. Soc.*, vol. 68, pp. 1091-1094 (1946).

Setayesh, S., et al., "Polyfluorenes with Polyphenylene Dendron Side Chains: Toward Non-Aggregating, Light-Emitting Polymers," *J. Am. Chem. Soc.*, vol. 123, pp. 946-953 (2001).

Liu, et al., "Solvolysis of 9-Aryl-9-Chlorofluorenes Revisited, Solvent and Substituent Effects," *Organic Reactivity*, vol. 31, No. 1, pp. 59-66 (1997).

Liu, et al., "Solvent and Substituent Effects in the Solvolysis of 9-Aryl-9-Bromofluorenes," *Journal of Chinese Chemical Society*, vol. 47, pp. 71-76 (2000).

Pixton, et al., "Gas Transport Properties of Polyarylates Part II: Tetrabromination of the Bisphenol," *Journal of Polymer Science: Part B: Polymer Physics*, vol. 33, pp. 1353-1364 (1995).

Ballester, et al., "Inert Carbon Free Radicals. 5. Perchloro-9-Phenylfluorenyl Radical series," *J. Org. Chem.*, vol. 49, pp. 770-778 (1981).

Bolton, R., et al., "Competition in Intramolecular Arylation of Triphenylmethanols," *J. Chem. Soc. Perkin Trans. II*, pp. 405-408 (1986).

Chen, et al., "New Gas Separation Membrane Materials Hologenated Dicarbonyl Phenylene Based Polyarylates," *Polymeric Materials Science and Engineering*, vol. 66, pp. 412-413 (1992).

Ono, et al., "Synthesis and Properties of 9,9'-Diaryl-4,5-Diazafluorenes. A New Type of Electron-Transporting and Hole Blocking Material in EL Device," *Chemistry Letters*, vol. 33, No. 3, pp. 276-277 (2004).

Database WPI, Accession No. 2007-366366, Feb. 22, 2007. XP002527927.

* cited by examiner

*Primary Examiner* — Jennifer Chriss
*Assistant Examiner* — Gregory Clark
(74) *Attorney, Agent, or Firm* — Connolly Bove Lodge & Hutz LLP

(57) ABSTRACT

The present invention relates to fluorine derivatives and organic electronic devices in which said compounds are used as a matrix material in the emitting layer and/or as a hole transport material, and/or as an electron blocking or exciton blocking material, and/or as an electron transport material.

17 Claims, No Drawings

FLUORINE DERIVATIVES FOR ORGANIC ELECTROLUMINESCENCE DEVICES

RELATED APPLICATIONS

This application is a national stage application (under 35 U.S.C. §371) of PCT/EP2009/001736, filed Mar. 11, 2009, which claims benefit of German Application No. 10 2008 017 591.9, filed Apr. 7, 2008.

The present invention relates to organic semiconductors and to the use thereof in organic electronic devices.

Organic semiconductors are being developed for a number of electronic applications of different types. The construction of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136. However, further improvements for the use of these devices for high-quality and long-lived displays are still desirable. Thus, there is currently a need to improve, in particular, the lifetime and efficiency of blue-emitting organic electroluminescent devices. It is furthermore necessary that the compounds have high thermal stability and a high glass-transition temperature and that they can be sublimed without decomposition. In particular for use at elevated temperature, a high glass-transition temperature is essential in order to achieve long lifetimes.

There continues to be a demand for improved materials, for example host materials for fluorescent and phosphorescent emitters, but further improvements are also desirable, in particular, in the case of charge-transport materials, i.e. hole- and electron-transport materials, and charge-blocking materials. The properties of these materials in particular are frequently limiting for the lifetime and efficiency of the organic electroluminescent device.

Surprisingly, it has been found that 9,9-diphenylfluorene derivatives which are substituted in the 3'- and 5'-positions of each of the two phenyl groups are very highly suitable for use in organic electroluminescent devices, where they result in significant improvements over the prior art. This likewise applies if 9,10-dihydroanthracene derivatives or corresponding heterocyclic derivatives are used instead of the fluorene. The present invention therefore relates to these compounds and to the use thereof in organic electronic devices. Depending on the substitution on the phenyl groups, the compounds according to the invention are particularly suitable as hole-transport materials, electron- or exciton-blocking materials, matrix materials for fluorescent or phosphorescent compounds, hole-blocking materials and electron-transport materials. The materials according to the invention enable an increase in the efficiency for the same or improved lifetime of the organic electronic device compared with materials in accordance with the prior art. Furthermore, these compounds have high thermal stability. In general, these materials are very highly suitable for use in organic electronic devices since they have a high glass-transition temperature. The corresponding extended structures, in particular indenofluorene structures and indenocarbazole structures, likewise have very good properties.

As closest prior art, U.S. Pat. No. 5,698,740, JP 2005/085599 and JP 2007/049055 may be mentioned. U.S. Pat. No. 5,698,740 and JP 2005/085588 disclose 9,9-diphenylfluorene derivatives which are substituted by at least one amino group or mono- or disubstituted amino group on each of the two phenyl groups. Only structures which are substituted by amino groups in each of the 4'-positions of the phenyl groups, i.e. para to the link to the fluorene, are explicitly disclosed. Structures which are substituted by a plurality of amino groups on one phenyl group are not disclosed. JP 2007/049055 discloses 9,9-diphenylfluorene derivatives which are substituted by at least one substituted or unsubstituted pyrrole or benzimidazole group on at least one of the two phenyl groups. Only structures which are substituted by amino groups in each of the 4-positions of the phenyl groups, i.e. para to the link to the fluorene, are explicitly disclosed. Structures which are substituted by a plurality of pyrrole or benzimidazole groups on one phenyl group are not disclosed. However, the substitution pattern disclosed in these applications does not result in compounds which have sufficiently good properties on use in organic electronic devices. Surprisingly, it has been found that specifically simultaneous substitution of both phenyl groups in each of the 3'- and 5'-positions is responsible for the good properties of the compounds according to the invention.

Furthermore, WO 05/053055 discloses a 9,9-bis(triazinyl) fluorene which carries a phenyl group in the 3,5-position of each triazine group as hole-blocking material in phosphorescent electroluminescent devices. However, the effect of this compound is attributed to the presence of the triazine groups in the molecule. The presence of substituents in the 3,5-position of the triazine is not accorded any importance.

For reasons of clarity, the structure and numbering of 9,9-diphenylfluorene are shown below:

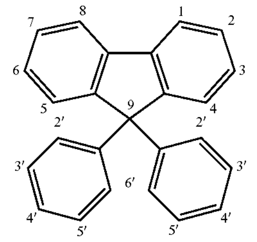

The invention thus relates to compounds of the formula (1)

formula (1)

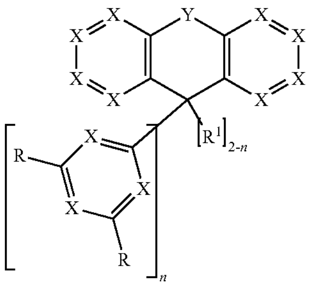

where the following applies to the symbols used:

X is on each occurrence, identically or differently, $CR^1$ or N, where a maximum of 3 groups X in each ring stand for N;

or two directly adjacent groups X stand for a unit of the following formula (7)

formula (7)

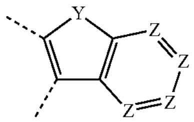

where the dashed bonds indicate the link of the unit to the adjacent C or N atoms;

Y is on each occurrence, identically or differently, a single bond or a group selected from $BR^1$, $C(R^1)_2$, C(=O), $C(=NR^1)$, $C(=C(R^1)_2)$, $Si(R^1)_2$, $NR^1$, $PR^1$, $P(=O)R^1$, O, S, S(=O), $S(=O)_2$, $C(R^1)_2$—$C(R^1)_2$, $C(R^1)_2$—$NR^1$ or $CR^1$=$CR^1$;

Z is on each occurrence, identically or differently, $CR^1$ or N, where a maximum of two symbols Z in each ring stand for N;

R is on each occurrence, identically or differently, Cl, Br, I, triflate, $B(OR^2)_2$, $B(R^2)_2$, $B(N(R^2)_2)_2$, $NAr_2$, $N(R^2)_2$, $SiAr_3$, $Si(R^2)_3$, C(=O)Ar, $C(=O)R^2$, OAr, $OR^2$, SAr, $SR^2$, S(=O)Ar, $S(=O)R^2$, $S(=O)_2Ar$, $S(=O)_2R^2$, $PAr_2$, $P(R^2)_2$, $P(=O)Ar_2$, $P(=O)(R^2)_2$ or an aromatic or heteroaromatic ring system having 5 to 60 aromatic ring atoms, which may be substituted by one or more radicals $R^1$;

Ar is on each occurrence, identically or differently, an aromatic or heteroaromatic ring system having 5 to 30 aromatic ring atoms, which may be substituted by one or more non-aromatic radicals $R^1$; two radicals Ar here which are bonded to the same nitrogen or phosphorus atom may also be linked to one another by a single bond or a bridge selected from $B(R^2)$, $C(R^2)_2$, $Si(R^2)_2$, C=O, $C=NR^2$, $C=C(R^2)_2$, O, S, S=O, $SO_2$, $N(R^2)$, $P(R^2)$ and $P(=O)R^2$;

$R^1$ is on each occurrence, identically or differently, H, D, F, Cl, Br, I, CHO, $N(R^2)_2$, $N(Ar)_2$, C(=O)Ar, $P(=O)(Ar)_2$, S(=O)Ar, $S(=O)_2Ar$, $CR^2$=$CR^2Ar$, CN, $NO_2$, $Si(R^2)_3$, $B(OR^2)_2$, $B(R^2)_2$, $B(N(R^2)_2)_2$, $OSO_2R^2$, a straight-chain alkyl, alkenyl, alkynyl, alkoxy or thioalkoxy group having 1 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C$=$CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems; two or more adjacent substituents $R^1$ here may also form a mono- or polycyclic, aliphatic or aromatic ring system with one another;

$R^2$ is on each occurrence, identically or differently, H, D or an aliphatic, aromatic and/or heteroaromatic hydrocarbon radical having 1 to 20 C atoms, in which, in addition, H atoms may be replaced by F; two or more adjacent substituents $R^2$ here may also form a mono- or polycyclic, aliphatic or aromatic ring system with one another;

n is 1 or 2;

the following compound is excluded from the invention:

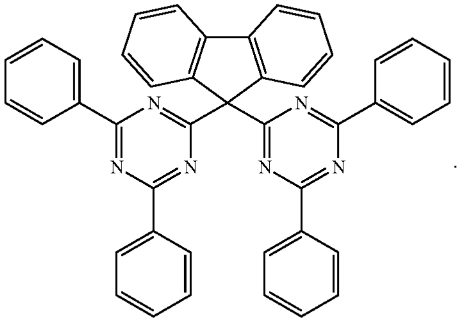 [SMILES: c1ccc(-c2nc(-c3ccccc3)nc(C3(c4nc(-c5ccccc5)nc(-c5ccccc5)n4)c4ccccc4-c4ccccc43)n2)cc1 ; "."]

.

The compounds of the formula (1) preferably have a glass-transition temperature $T_G$ of greater than 70° C., particularly preferably greater than 100° C., very particularly preferably greater than 110° C.

As evident from the formula (1), n=2 means that two aryl radicals which are substituted in the 3,5-position are bonded in the 9,9-position of the fluorene or of the corresponding derivative in the compound, while n=1 means that one such aryl radical and furthermore one group $R^1$ are present.

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a single aromatic ring, i.e. benzene, or a single heteroaromatic ring, for example pyridine, pyrimidine, thiophene, etc., or a condensed aryl or heteroaryl group, for example naphthalene, anthracene, pyrene, quinoline, isoquinoline, etc.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to mean aromatic ring systems for the purposes of this invention. An aromatic or heteroaromatic ring system is likewise taken to mean systems in which a plurality of aryl or heteroaryl groups are linked to one another by single bonds, for example biphenyl, terphenyl or bipyridine.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoro-ethyl and 2,2,2-trifluoroethyl. For the purposes of this invention, an alkenyl group is taken to mean, in particular, ethenyl, propenyl, butenyl, pentenyl, cyclopentenyl, hexenyl, cyclohexenyl, heptenyl, cycloheptenyl, octenyl or cyclooctenyl. For the purposes of this invention, an alkynyl group is taken to mean, in particular, ethynyl, propynyl, butynyl, pentynyl, hexynyl, heptynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the above-mentioned radicals R and which can be linked to the aromatic or heteroaromatic ring system via any desired positions, is taken to mean, in particular, groups derived from benzene, naphthalene, anthracene, phenanthrene, benzanthracene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the invention, the symbol X stands, identically or differently on each occurrence, for $CR^1$ or N, where a maximum of one symbol X per ring in the fluorene unit stands for N and where either all symbols X in the substituents in the 9-position of the fluorene unit stand for $CR^1$ or all symbols X stand for N. In a further preferred embodiment of the invention, precisely two adjacent groups X stand for a unit of the above-mentioned formula (7). The substituents in the 9-position of the fluorene thus preferably stand for 3,5-substituted phenyl or triazine. A corresponding situation applies if the central unit does not represent fluorene, but instead one of the other derivatives covered by formula (1). The symbol X particularly preferably stands for $CR^1$.

The symbol Z in the unit of the formula (7) preferably stands for $CR^1$.

A preferred embodiment of the compounds of the formula (1) are the compounds of the formulae (2), (3), (8), (9), (10) and (11):

formula (2)

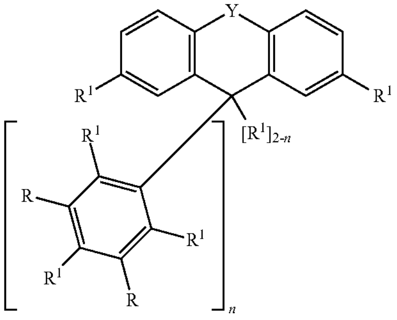

formula (3)

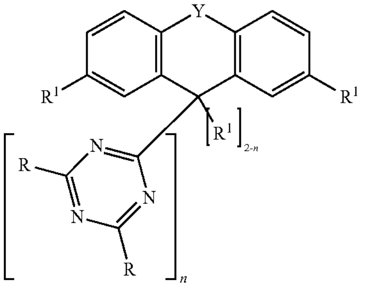

formula (8)

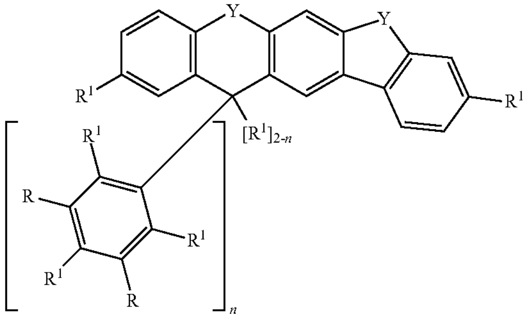

formula (9)

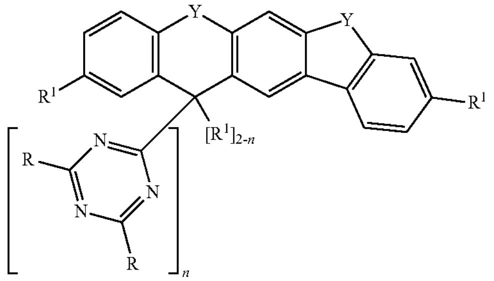

formula (10)

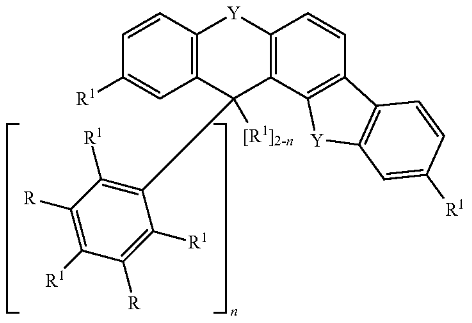

-continued formula (11)

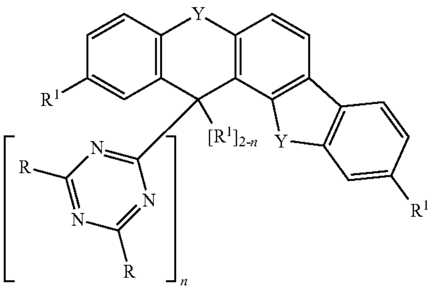

where the symbols and indices used have the meanings indicated above.

In a preferred embodiment of the invention, the symbol Y in the six-membered ring in compounds of the formula (1), (2), (3), (8), (9), (10) or (11) stands for a single bond or a group selected from $C(R^1)_2$, O or $NR^1$, particularly preferably for a single bond, and in the five-membered ring preferably stands for a group selected from $C(R^1)_2$, O or $NR^1$, particularly preferably for $C(R^1)_2$ or N, very particularly preferably for $C(R^1)_2$.

Preference is therefore given to the compounds of the formulae (2a), (3a), (8a), (8b), (9a), (9b), (10a), (10b), (11a) and (11b):

formula (2a)

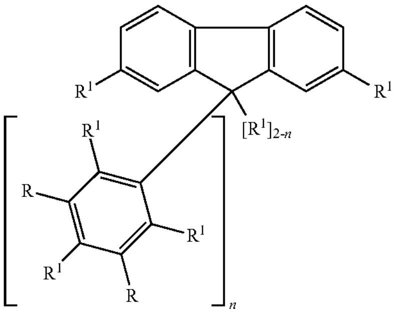

formula (3a)

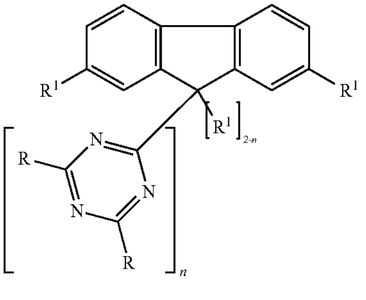

-continued formula (8a)

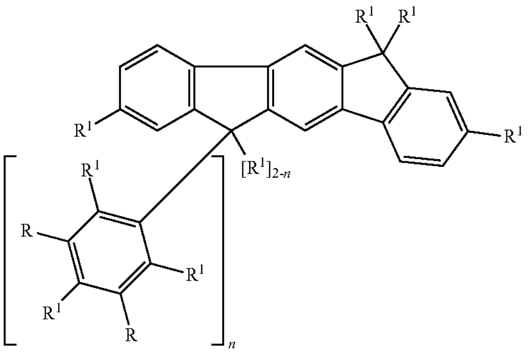

formula (8b)

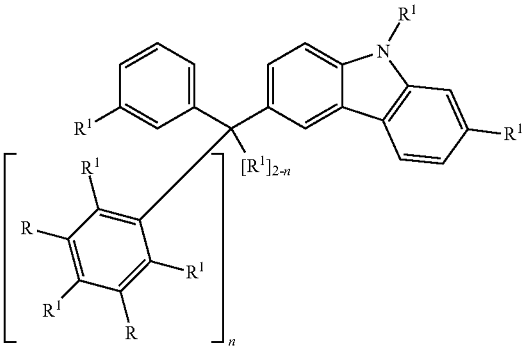

formula (9a)

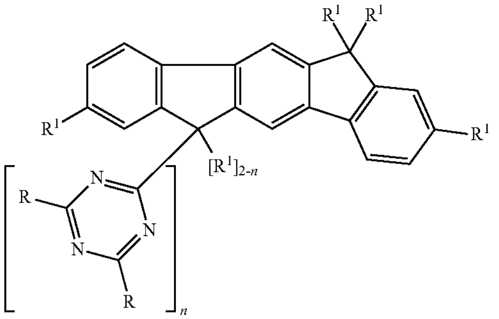

formula (9b)

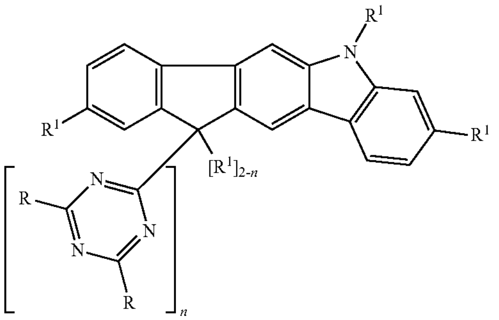

-continued formula (10a)

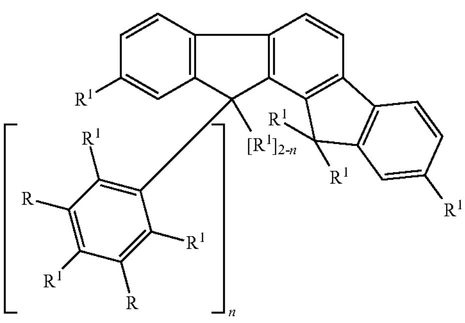

formula (10b)

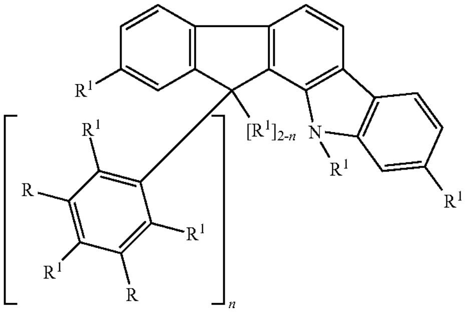

formula (11a)

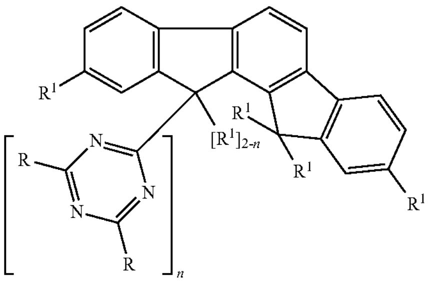

formula (11b)

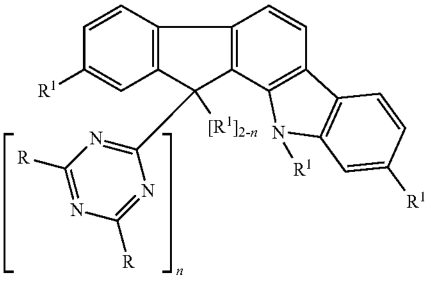

where the symbols and indices used have the meanings mentioned above.

In a preferred embodiment of the invention, n=2.

A further preferred embodiment of the compounds of the formula (1) are the compounds of the formulae (4a) and (4b):

formula (4a)

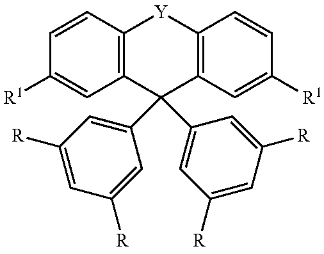

formula (4b)

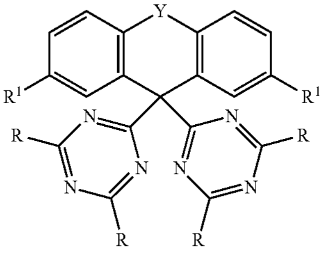

where the symbols used have the meanings indicated above.

A particularly preferred embodiment of the invention are the compounds of the following formulae (4c), (4d), (8c), (8d), (9c), (9d), (10c), (10d), (11c) and (11d):

formula (4c)

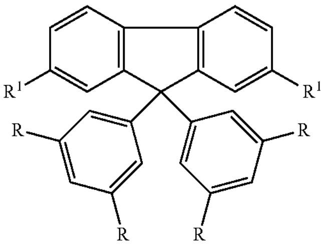

formula (4d)

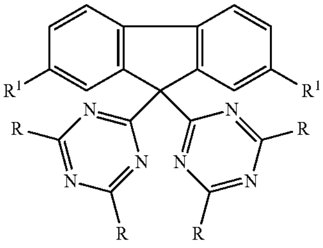

formula (8c)

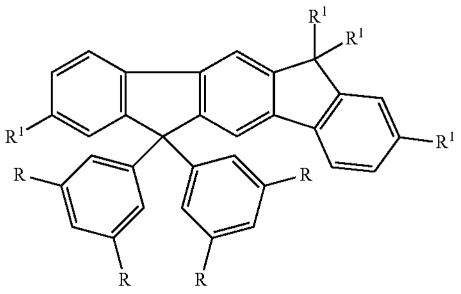

-continued formula (8d)

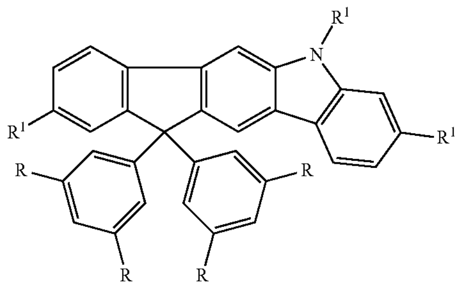

formula (9c)

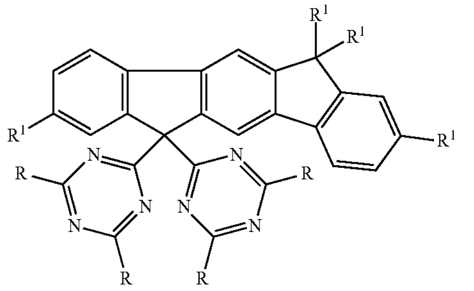

formula (9d)

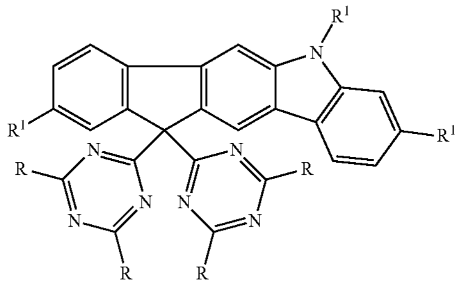

formula (10c)

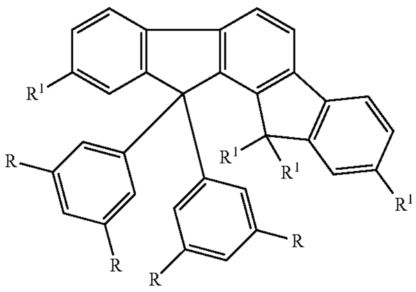

formula (10d)

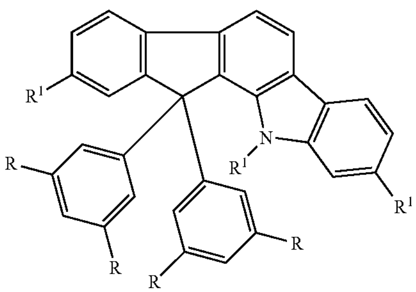

-continued formula (11c)

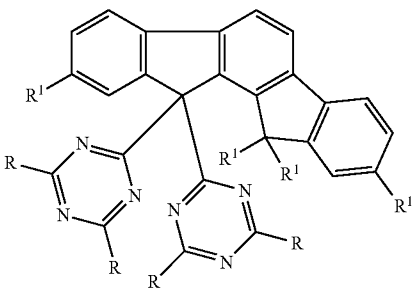

formula (11d)

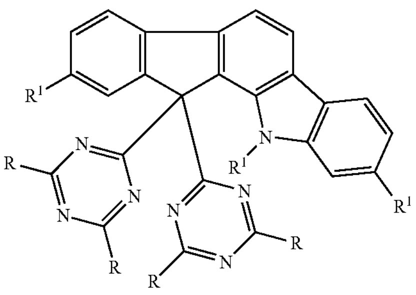

where the symbols and indices used have the meanings mentioned above.

In a further preferred embodiment of the invention, the symbol R in compounds of the formulae mentioned above stands, identically or differently on each occurrence, for $NAr_2$, C(═O)Ar, P(═O)$Ar_2$ or for an aromatic or heteroaromatic ring system having 5 to 30 aromatic ring atoms, which may be substituted by one or more non-aromatic radicals $R^1$. R particularly preferably, if it is bonded to a phenyl group, stands, identically or differently, preferably identically, on each occurrence for $NAr_2$ or C(═O)Ar, very particularly preferably for $NAr_2$. R particularly preferably, if it is bonded to a triazine group, stands for an aryl or heteroaryl group having 5 to 10 aromatic ring atoms. Substituents R which are furthermore preferred are Cl, Br, I and triflate, in particular Br, since these are valuable intermediates in the synthesis of further compounds according to the invention.

In a further preferred embodiment of the invention, all symbols R in compounds of the above-mentioned formulae are selected identically. This preference can be explained by the easier synthetic accessibility of the compounds.

If the radical R or $R^1$ stands for a group $N(Ar)_2$, this group is preferably selected from the groups of the formula (5) or formula (6):

formula (5)

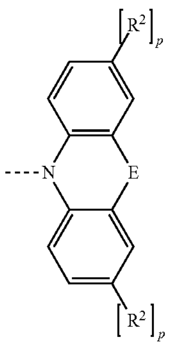

-continued formula (6)

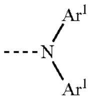

where $R^2$ has the meaning indicated above, and furthermore:

E stands for a single bond, O, S, $N(R^2)$ or $C(R^2)_2$;

$Ar^1$ is, identically or differently on each occurrence, an aromatic or heteroaromatic ring system having 5 to 20 aromatic ring atoms or a triarylamine group having 15 to 30 aromatic ring atoms, each of which may be substituted by one or more radicals $R^2$, preferably an aryl or heteroaryl group having 6 to 14 aromatic ring atoms or a triarylamine group having 18 to 30 aromatic ring atoms, preferably having 18 to 22 aromatic ring atoms, each of which may be substituted by one or more radicals $R^2$;

p is on each occurrence, identically or differently, 0 or 1.

$Ar^1$ particularly preferably stands, identically or differently on each occurrence, for phenyl, biphenyl, 1-naphthyl, 2-naphthyl, 2-, 3- or 4-triphenylamine, 1- or 2-naphthyldiphenylamine, each of which may be bonded via the naphthyl or phenyl group, or 1- or 2-dinaphthylphenylamine, each of which may be bonded via the naphthyl or phenyl group, N-carbazolyl or N-phenyl-2-carbazolyl or N-phenyl-3-carbazolyl. These groups may each be substituted by one or more alkyl groups having 1 to 4 C atoms or by fluorine.

If the radical R or $R^1$ represents an aromatic or heteroaromatic ring system, this is preferably selected from aromatic or heteroaromatic ring systems having 5 to 30 aromatic ring atoms, in particular having 6 to 20 aromatic ring atoms, very particularly preferably from phenyl, 1-naphthyl, 2-naphthyl, anthracenyl, phenylanthracenyl, 1- or 2-naphthylanthracenyl, binaphthyl, pyrenyl, fluoranthenyl, 2-, 3-, 4-, 5-, 6- or 7-benzanthracenyl, N-benzimidazolyl, phenyl-N-benzimidazolyl, N-phenylbenzimidazolyl and phenyl-N-phenylbenzimidazolyl.

In a further preferred embodiment of the invention, the symbol $R^1$ in compounds of the above-mentioned formulae stands, identically or differently on each occurrence, for H, F, $N(Ar)_2$, C(=O)Ar, $P(=O)(Ar)_2$, S(=O)Ar, $S(=O)_2Ar$, $CR^2{=}CR^2Ar$, a straight-chain alkyl group having 1 to 10 C atoms or a branched or cyclic alkyl group having 3 to 10 C atoms, each of which may be substituted by one or more radicals $R^2$, where one or more non-adjacent $CH_2$ groups may be replaced by $R^2C{=}CR^2$ or O and where one or more H atoms may be replaced by F, or an aromatic or heteroaromatic ring system having 5 to 20 aromatic ring atoms, which may in each case be substituted by one or more radicals $R^2$, or a combination of these systems; two or more adjacent substituents $R^1$ here may also form a mono- or polycyclic, aliphatic or aromatic ring system with one another. In a particularly preferred embodiment of the invention, the symbol $R^1$ in compounds of the above-mentioned formulae stands, identically or differently on each occurrence, for H, F, $N(Ar)_2$, a straight-chain alkyl group having 1 to 6 C atoms or a branched or cyclic alkyl group having 3 to 6 C atoms, each of which may be substituted by one or more radicals $R^2$, where one or more H atoms may be replaced by F, or an aromatic or heteroaromatic ring system having 5 to 14 aromatic ring atoms, which may in each case be substituted by one or more radicals $R^2$; two or more adjacent substituents $R^1$ here may also form a mono- or polycyclic, aliphatic or aromatic ring system with one another. In particular, $R^1$ stands, identically or differently on each occurrence, for H, F, methyl, ethyl, isopropyl or tert-butyl, in particular for H. In the case of compounds which are processed from solution, linear or branched alkyl chains having up to 10 C atoms are also preferred.

Preferred radicals $R^1$ which are present in the bridge Y on corresponding choice of Y are identical or different on each occurrence and are preferably selected from H, straight-chain alkyl groups having 1 to 6 C atoms or branched alkyl groups having 3 to 6 C atoms, where one or more non-adjacent $CH_2$ groups may be replaced by $-R^2C{=}CR^2-$, $-C{\equiv}C-$ or —O— and where one or more H atoms may be replaced by F, or aryl groups having 6 to 20 C atoms or heteroaryl groups having 2 to 20 C atoms, each of which may be substituted by one or more radicals $R^2$, or a combination of two or three of these systems; two of the radicals $R^1$ here which are both bonded to Y may also form a ring system with one another and thus form a Spiro system. Particularly preferred radicals $R^1$ which are bonded to the bridges Y are identical or different on each occurrence and are selected from methyl, ethyl, isopropyl, tert-butyl, where in each case one or more H atoms may be replaced by F, or aryl groups having 6 to 14 C atoms, which may be substituted by one or more radicals $R^2$; two radicals $R^1$ here may also form a ring system with one another. In the case of compounds which are processed from solution, linear or branched alkyl chains having up to 10 C atoms are also preferred. If the bridge Y is a group $NR^1$, the group $R^1$ is also particularly preferably selected from an aromatic or heteroaromatic ring system having 5 to 20 aromatic ring atoms.

Examples of preferred compounds of the formulae (1) to (4) are structures (1) to (276) depicted below.

(1)

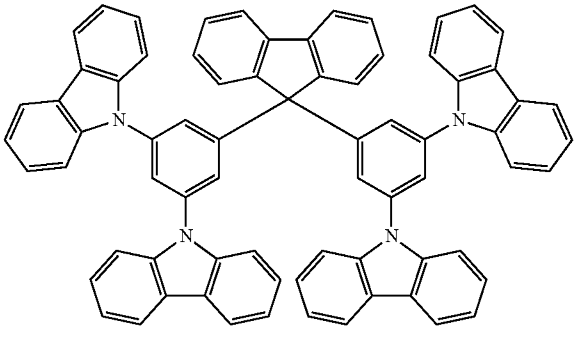

(2)

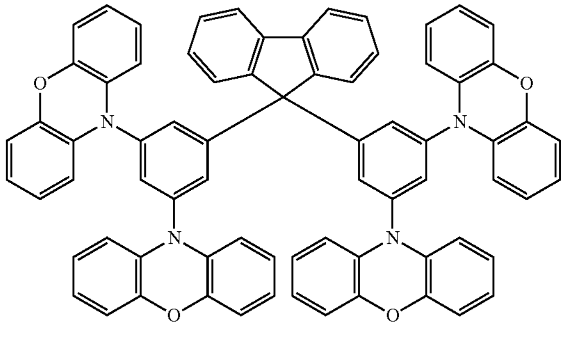

-continued
(3)
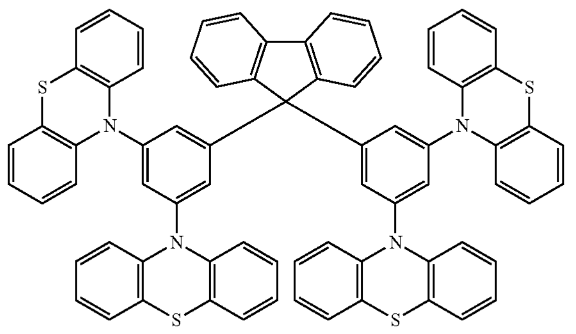
(4)
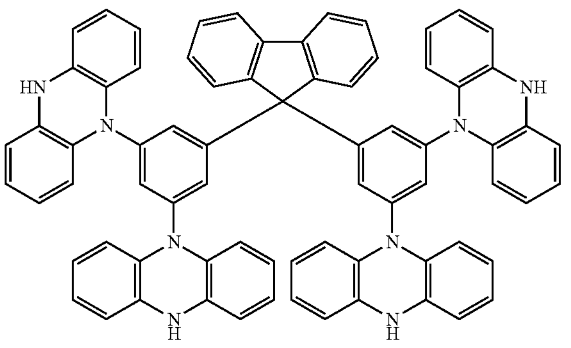
(5)
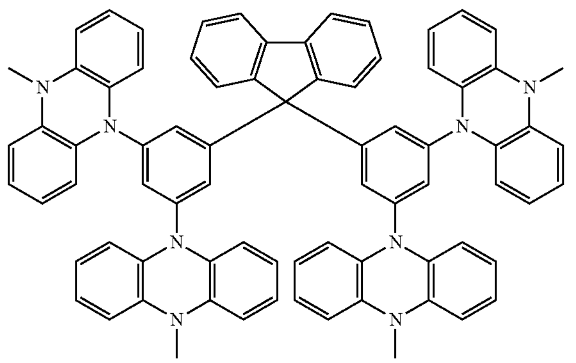
(6)
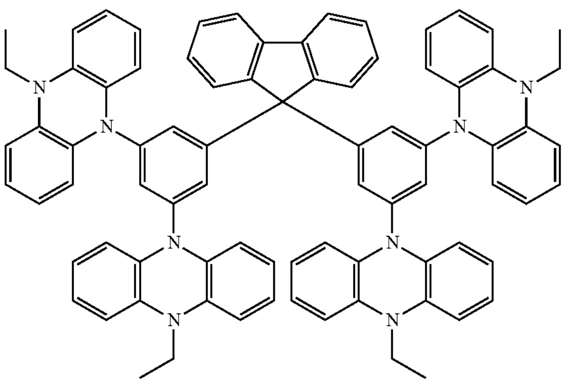
(7)
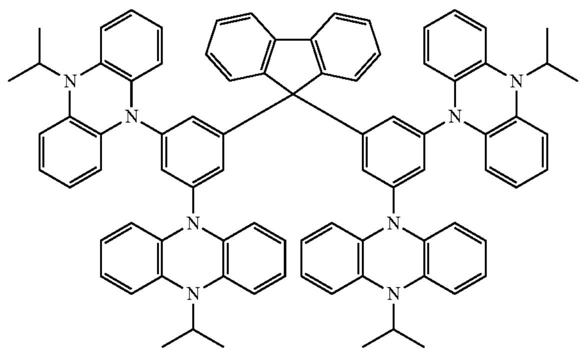
(8)
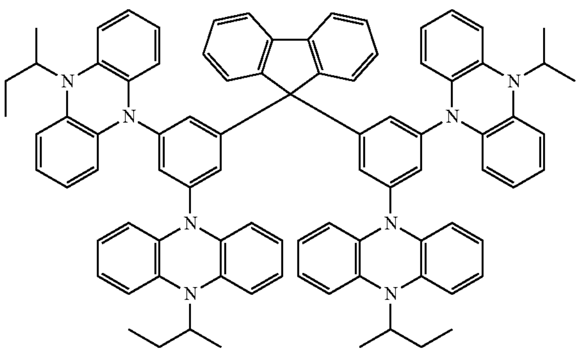
(9)
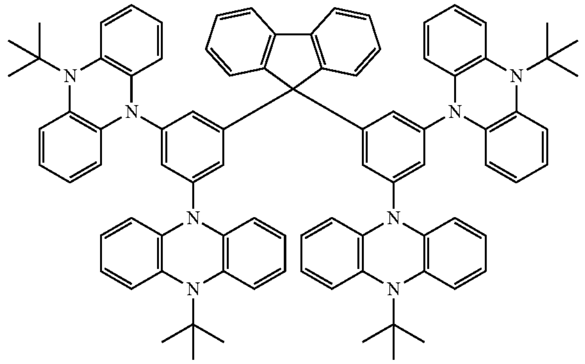
(10)
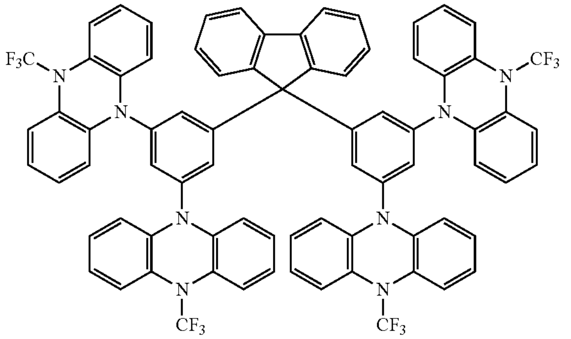

-continued
(11)
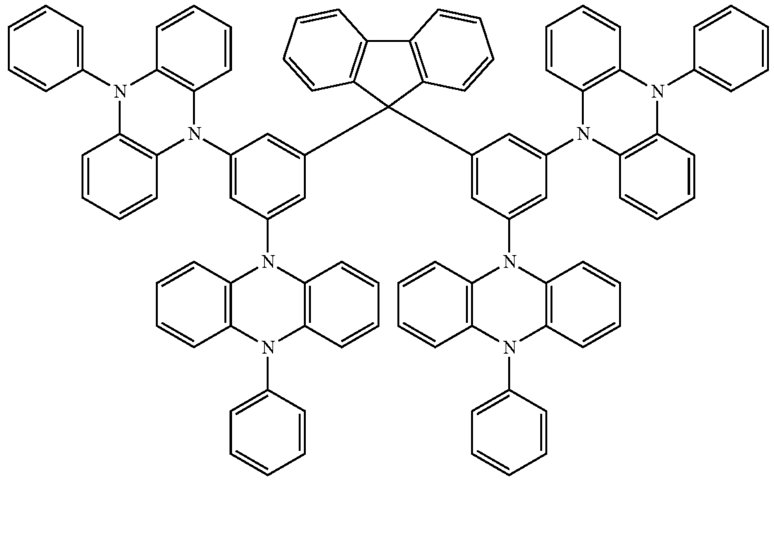
(12)
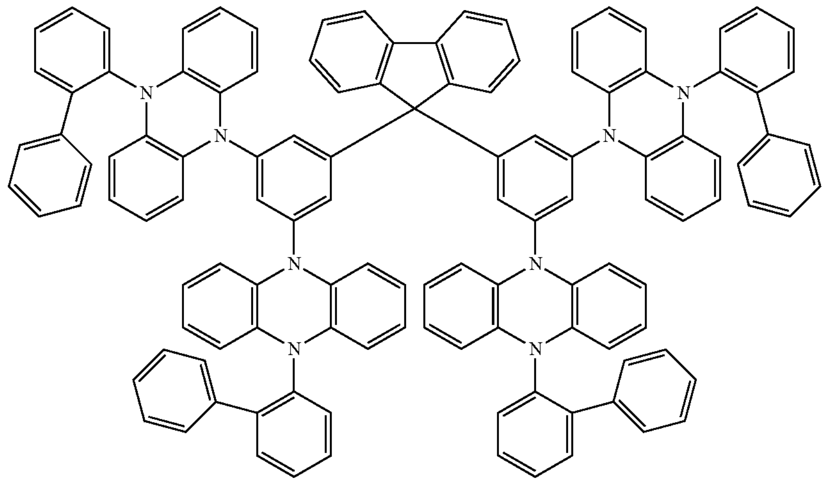
(13)
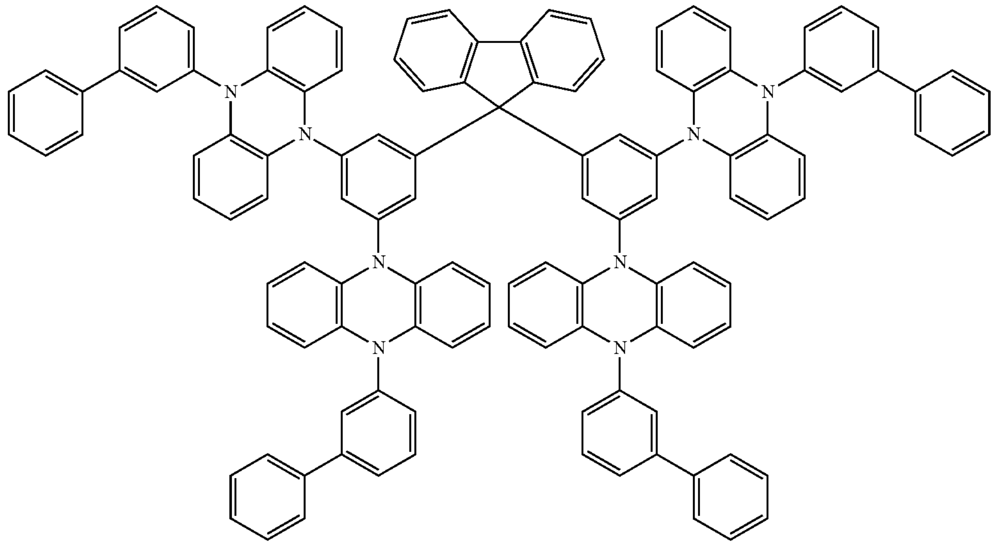

-continued
(14)
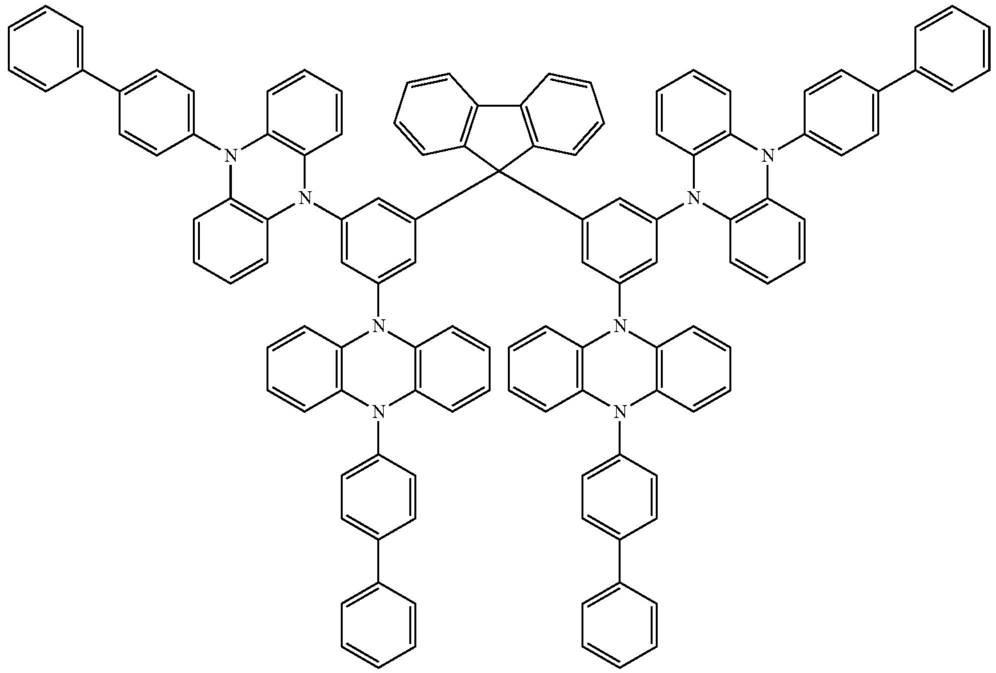
(15)
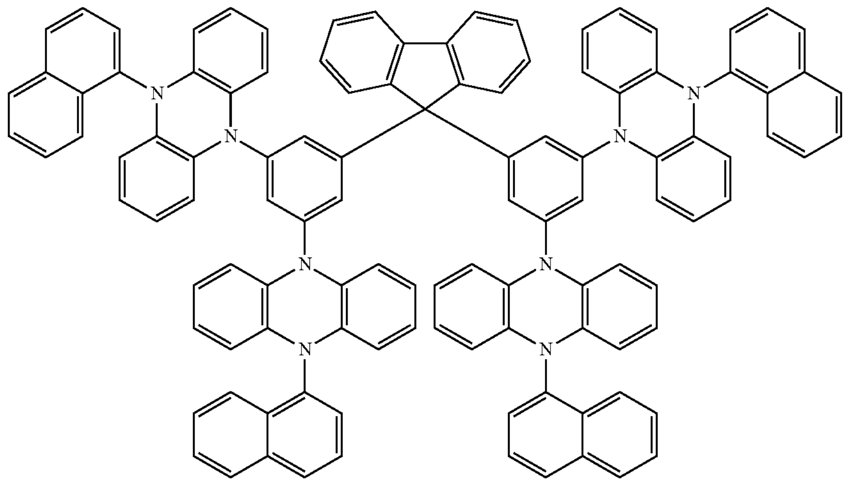

-continued
(16)
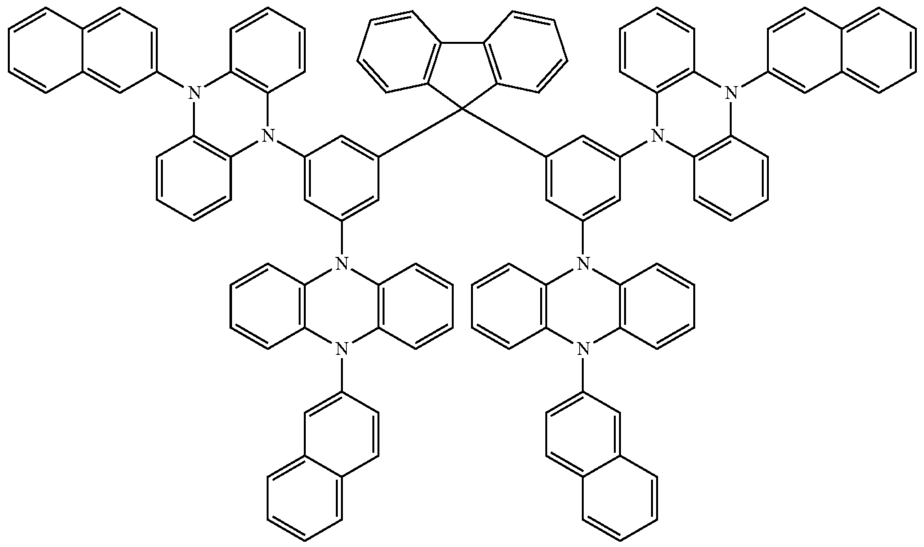
(17)
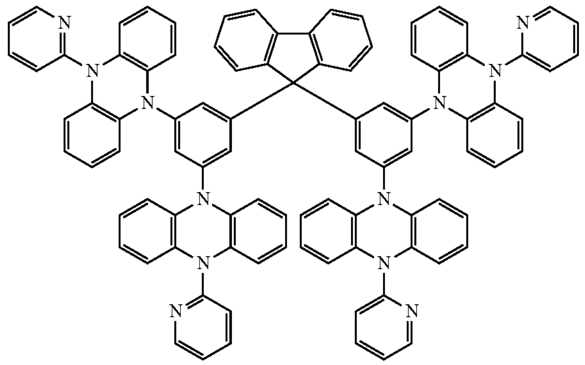
(18)
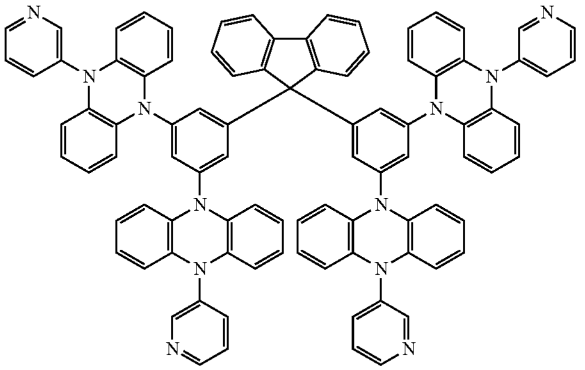
(19)
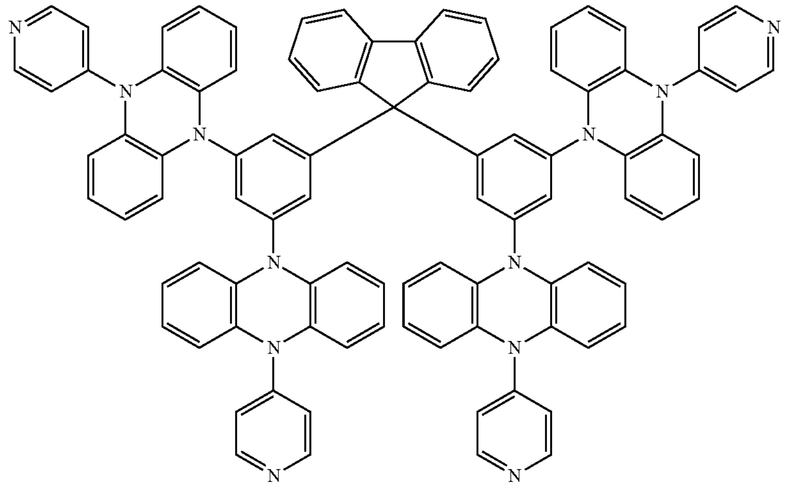

-continued
(20)
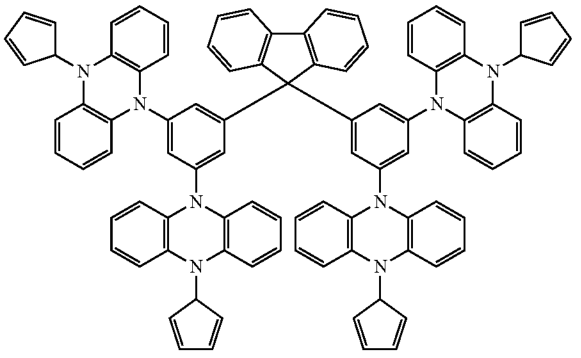
(21)
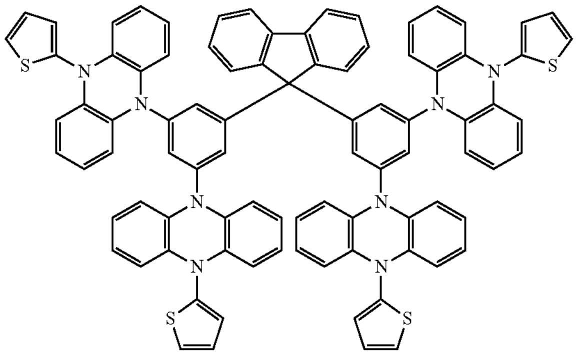
(22)
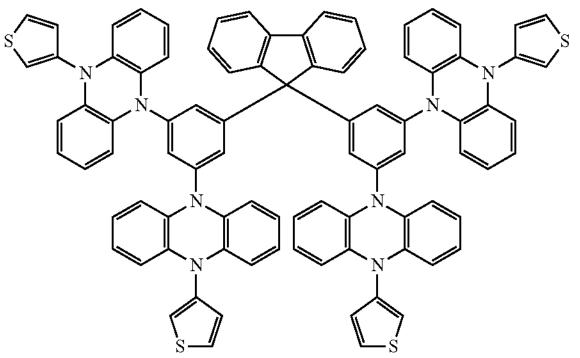
(23)
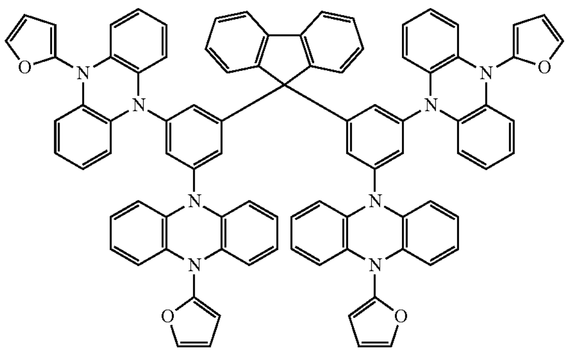
(24)
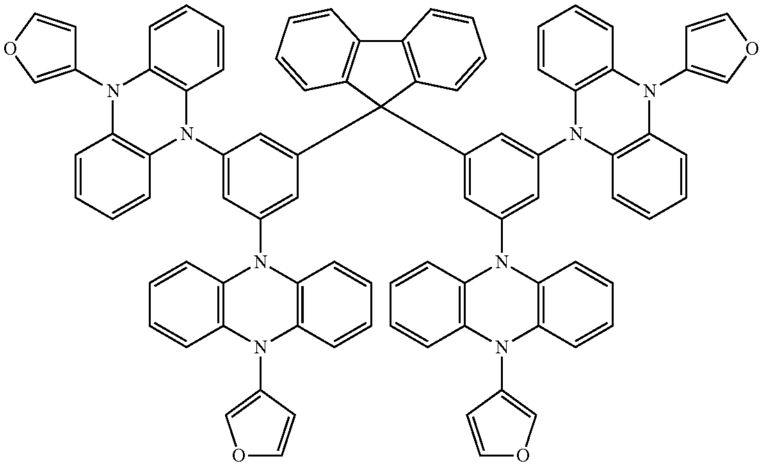
(25)
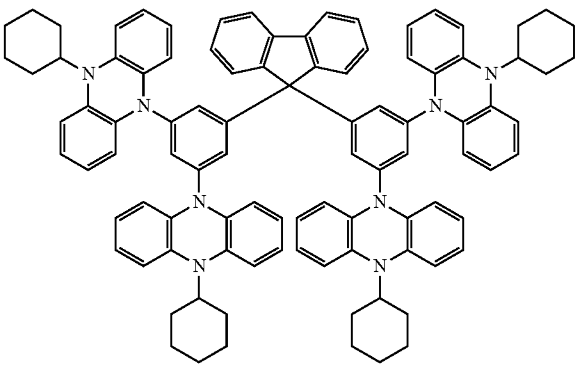
(26)
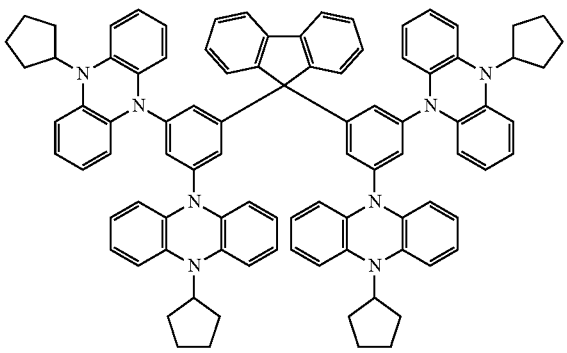

-continued
(27)
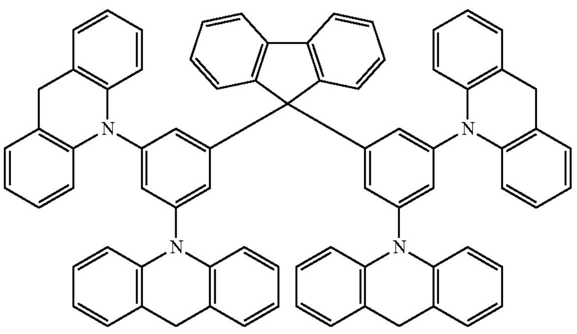
(28)
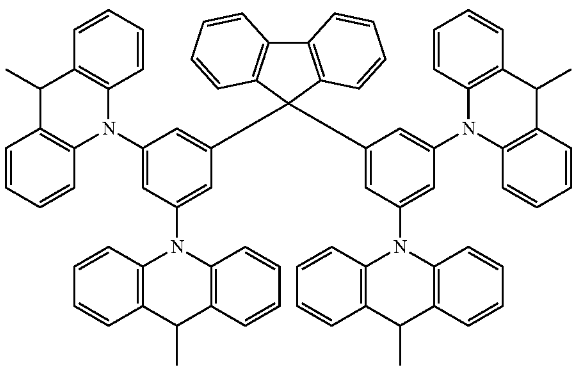
(29)
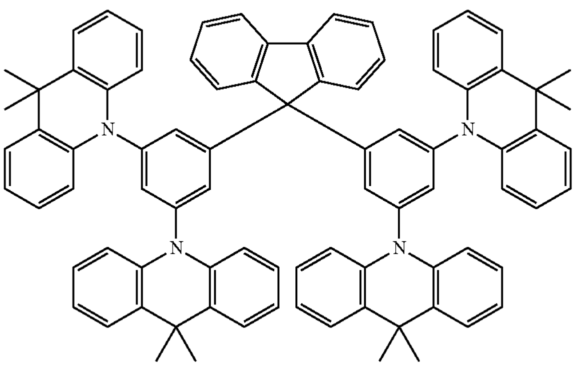
(30)
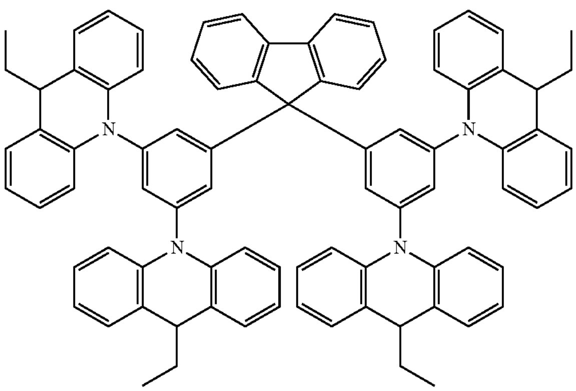
(31)
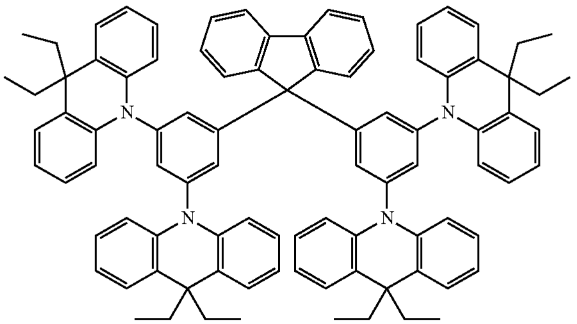
(32)
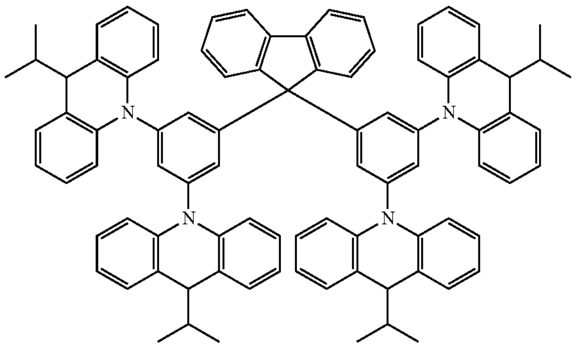
(33)
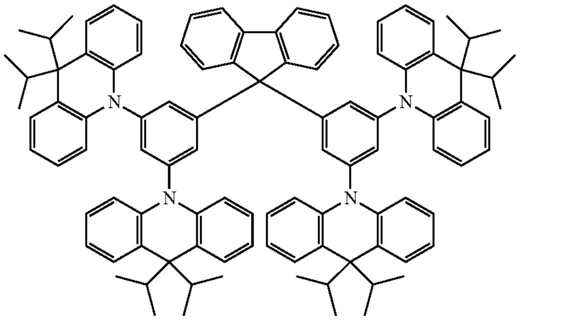
(34)
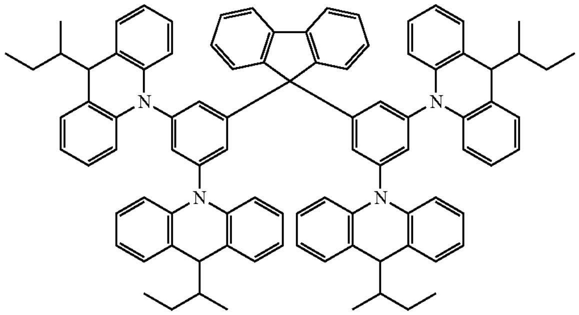

-continued
(35)
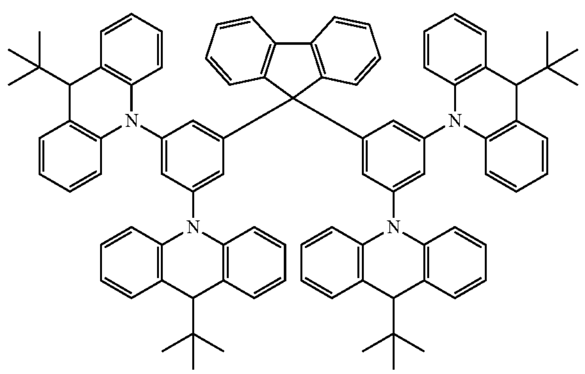
(36)
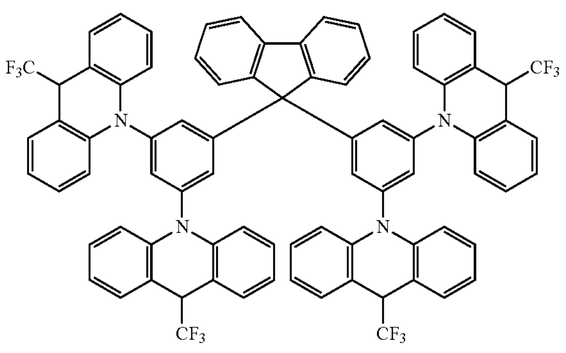
(37)
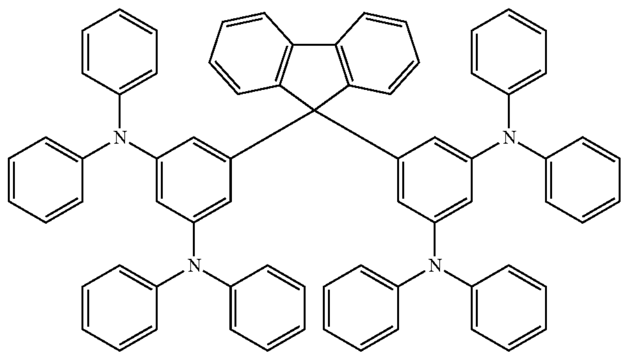
(38)
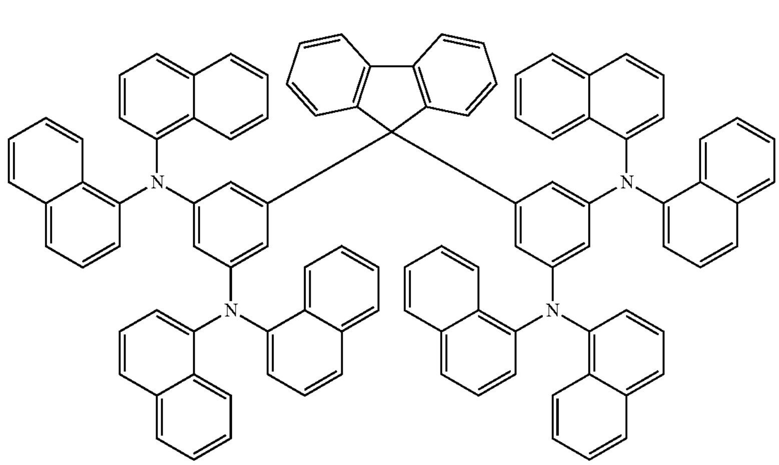

-continued
(39)
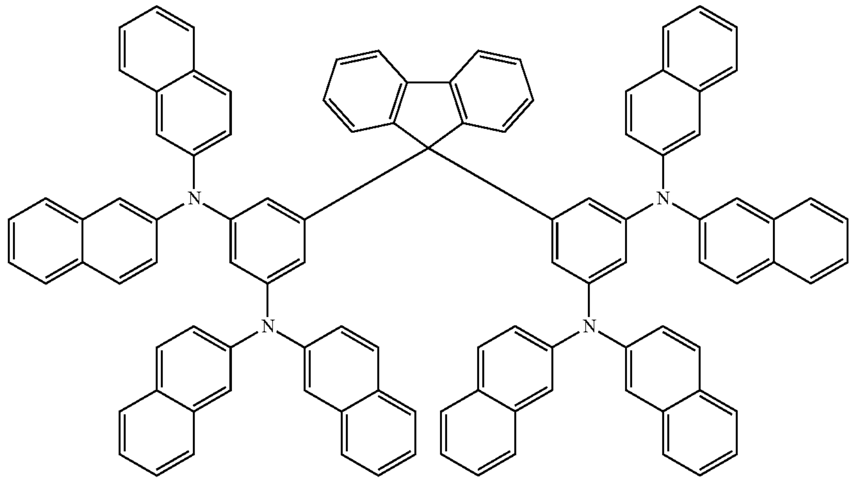
(40)
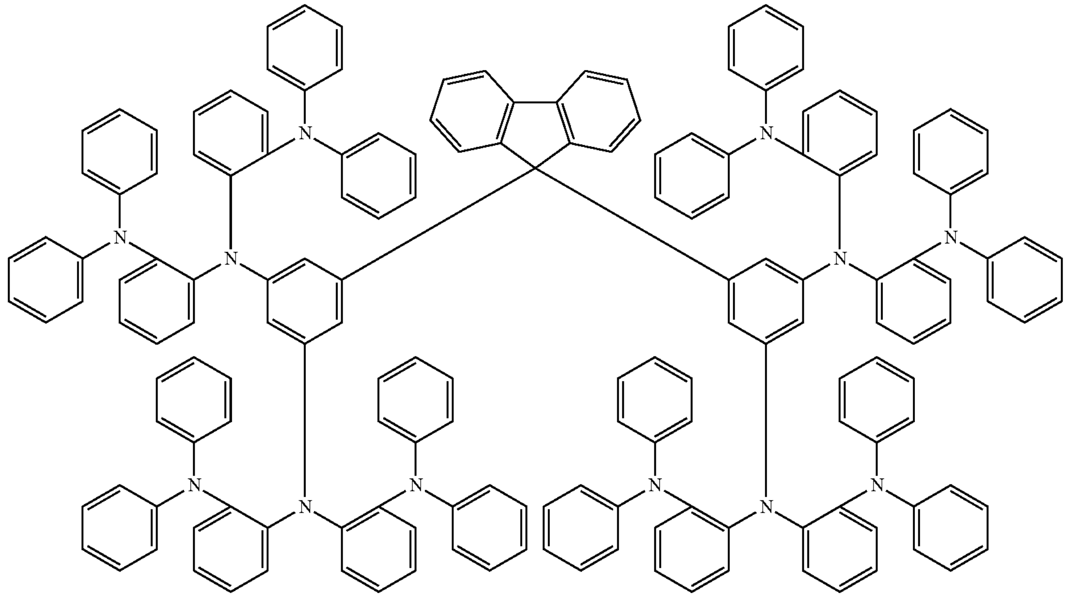
(41)
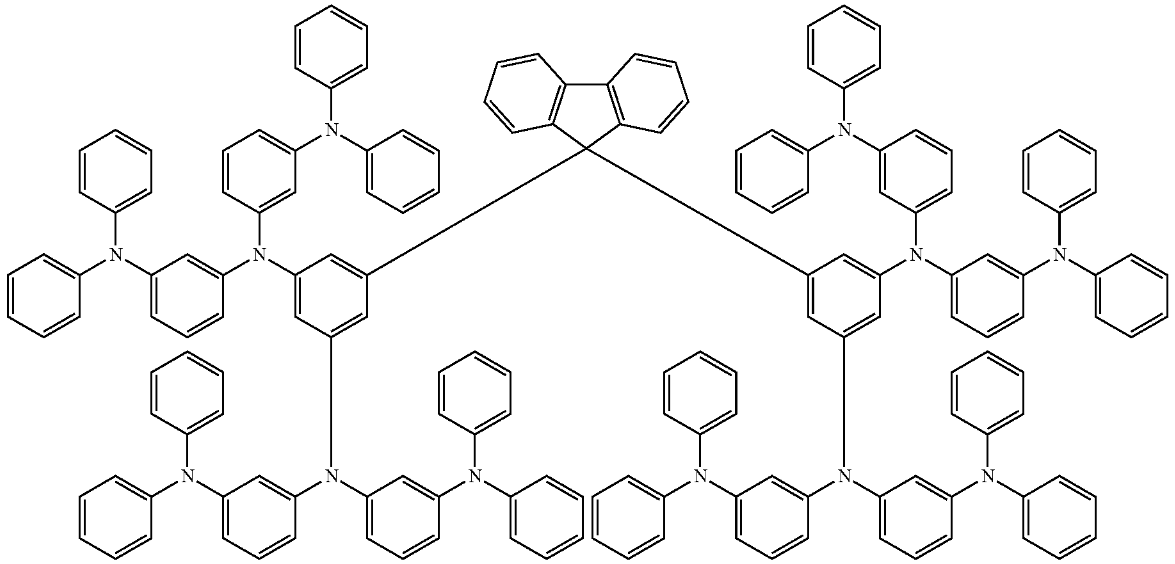

-continued
(42)
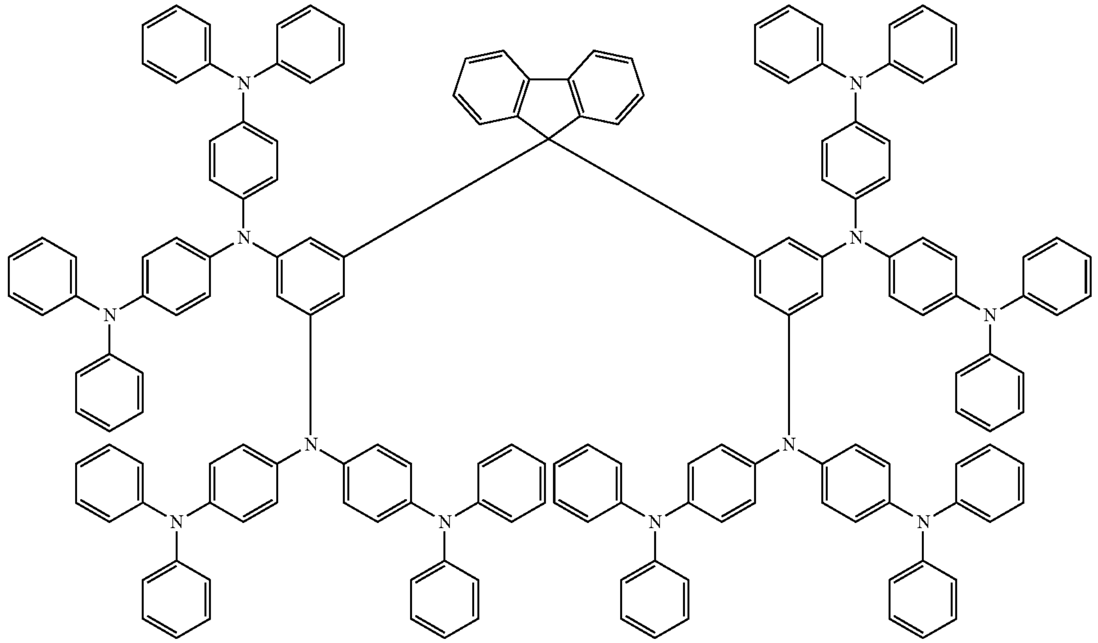
(43)
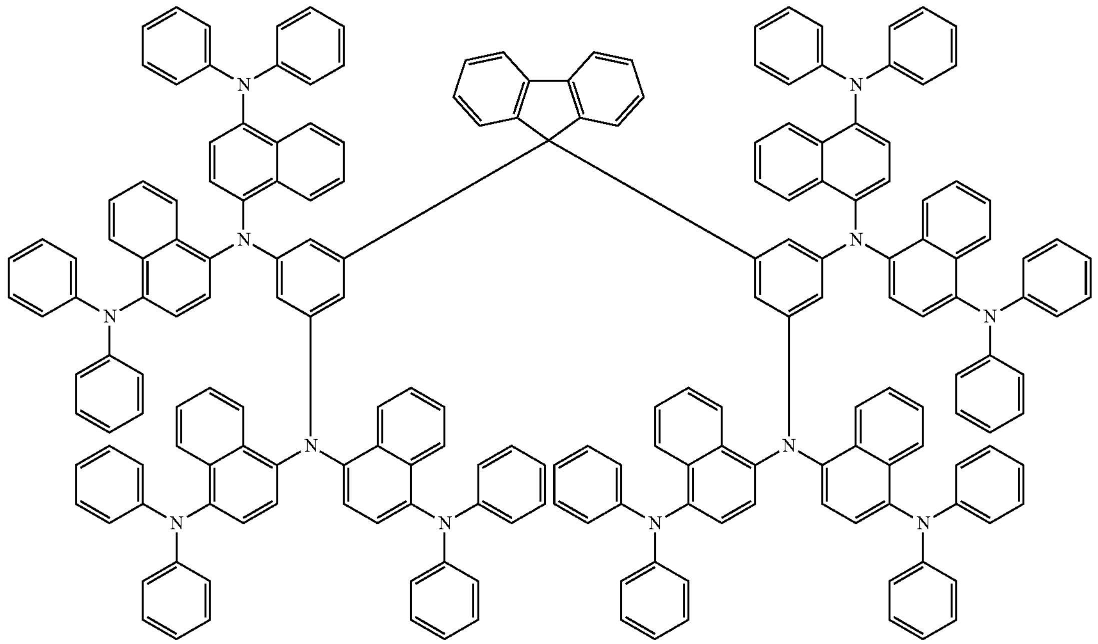

-continued
(44)
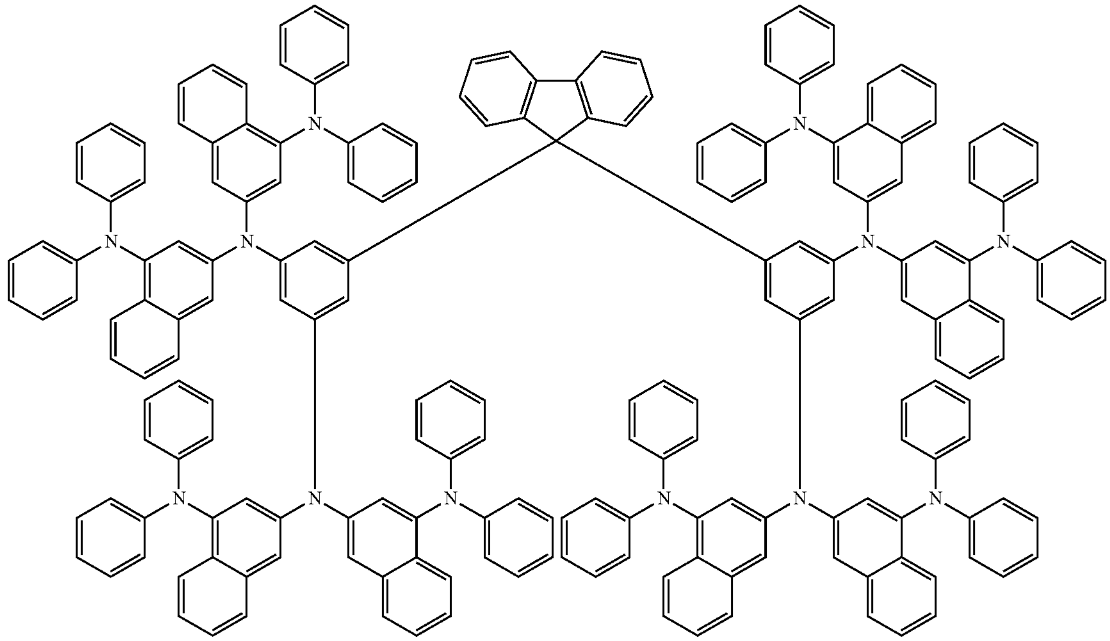
(45)
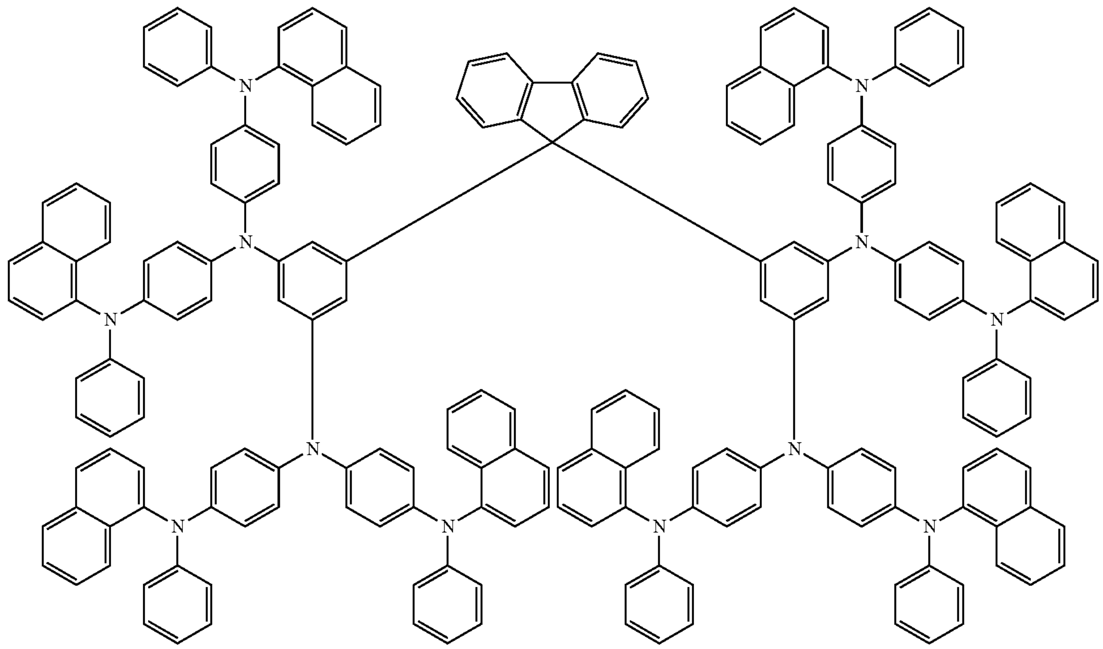

-continued
(46)
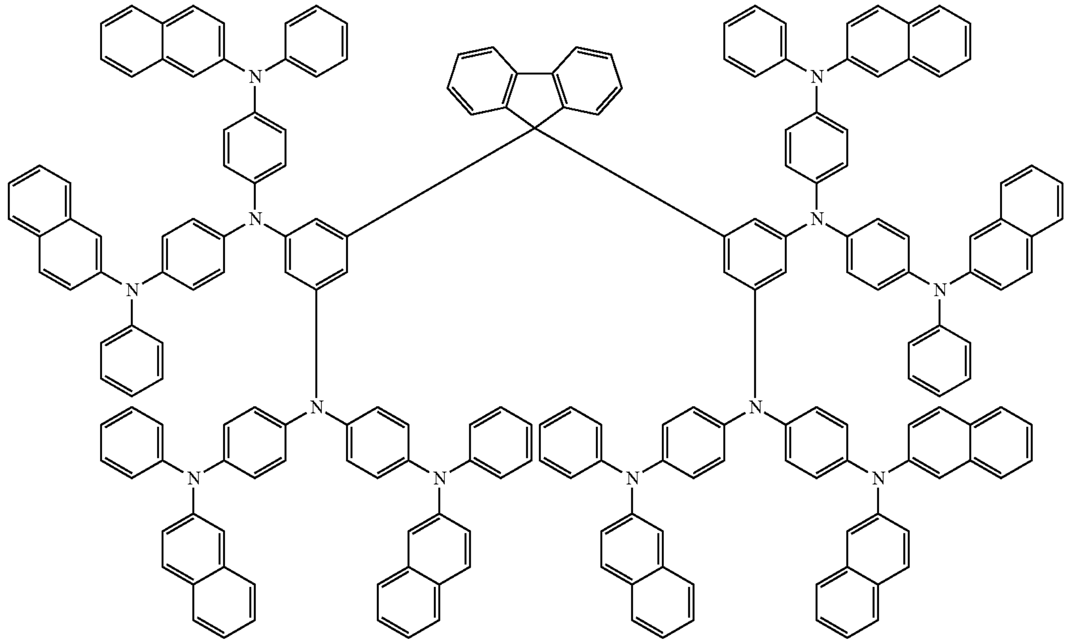
(47)
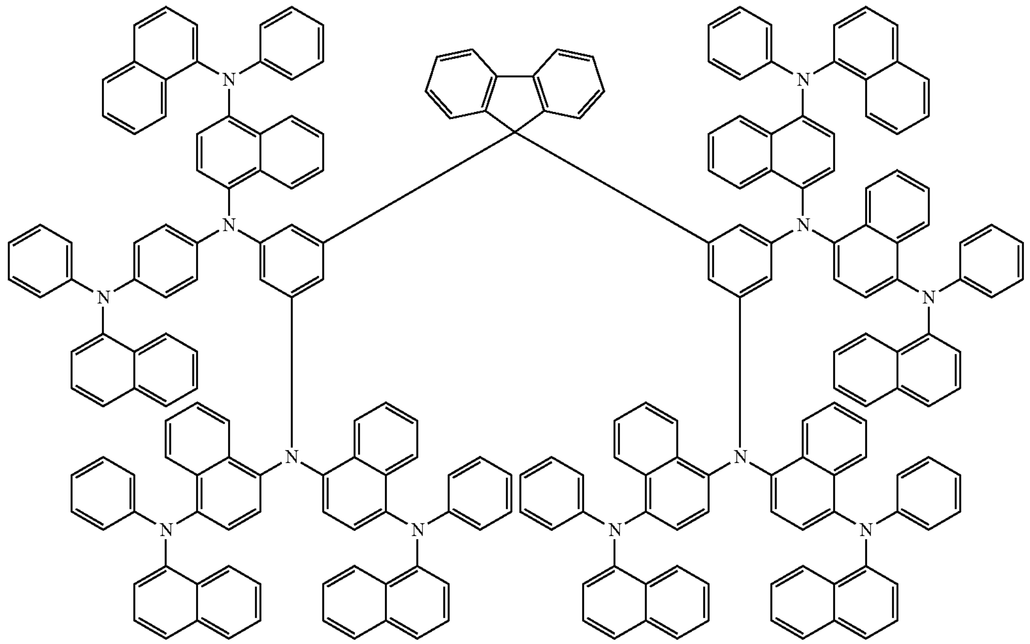

-continued
(48)
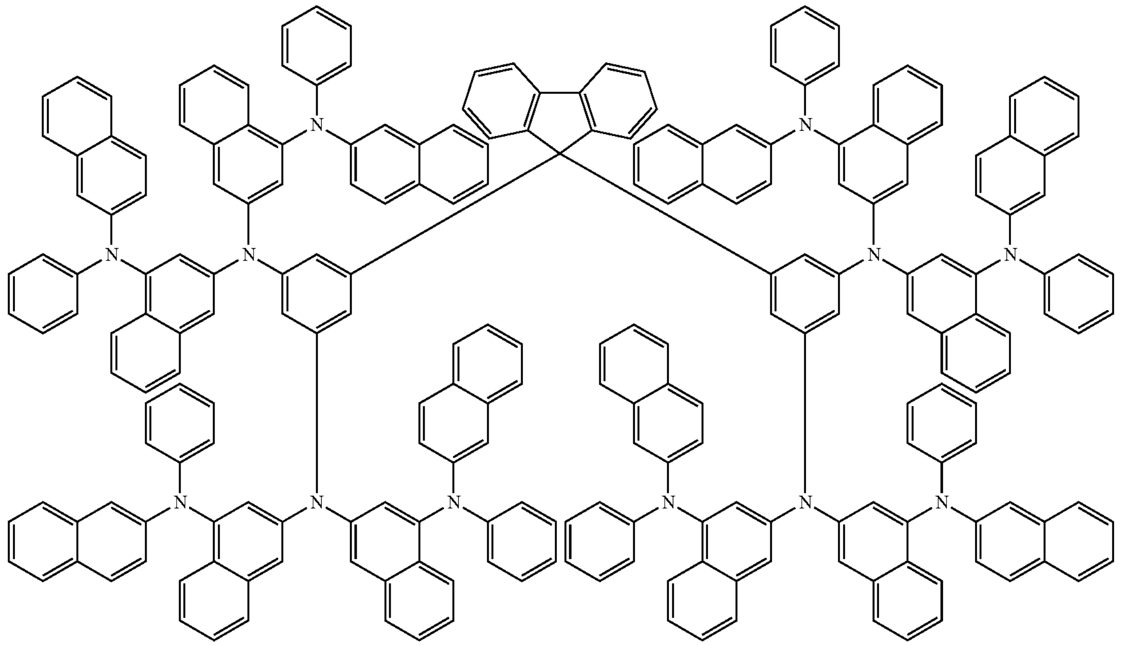
(49)
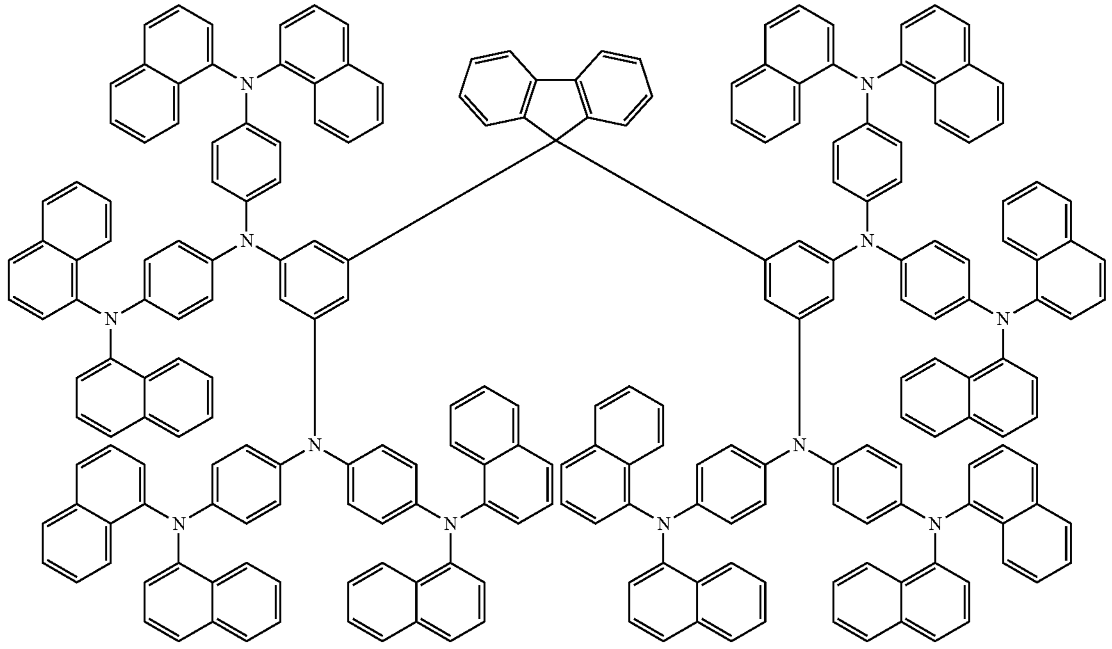

-continued
(50)
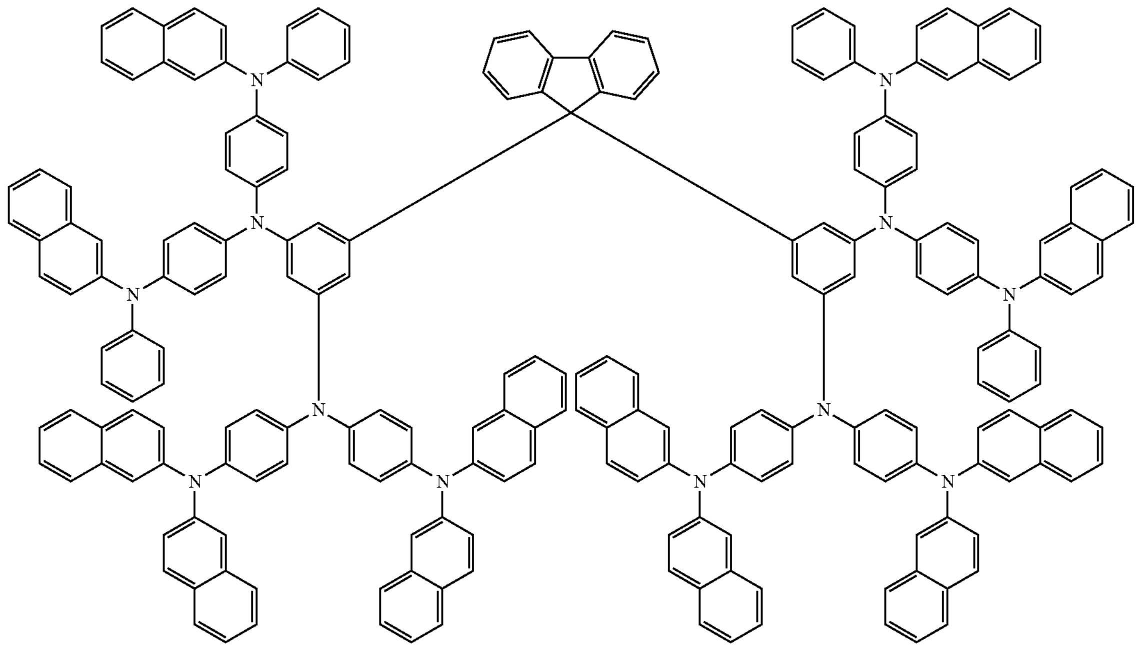
(51)
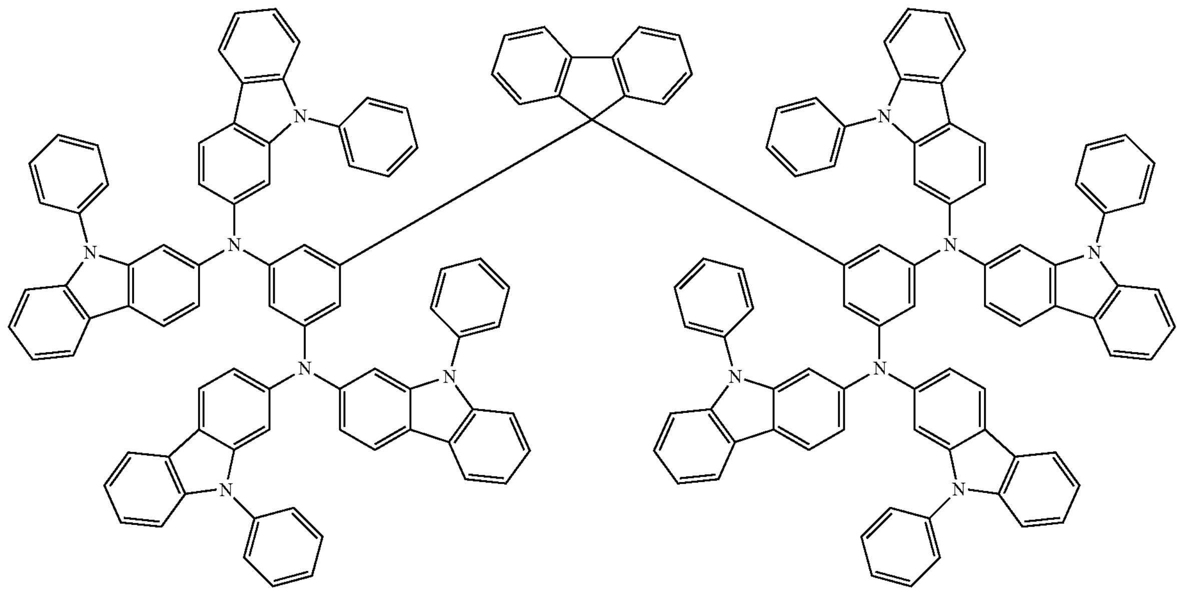

-continued
(52)
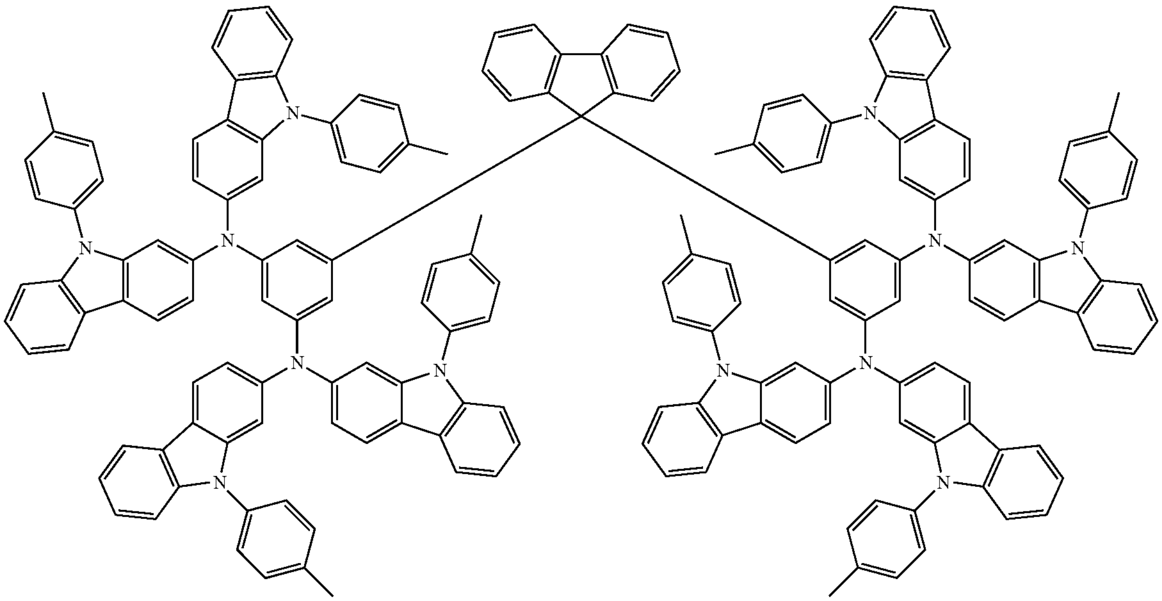
(53)
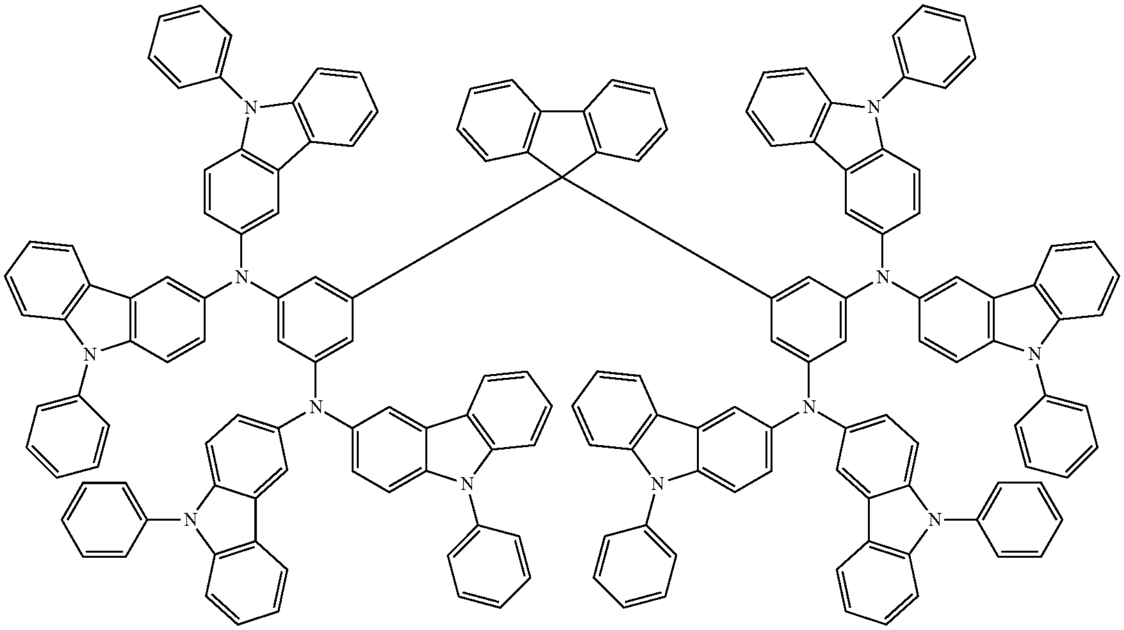
(54)
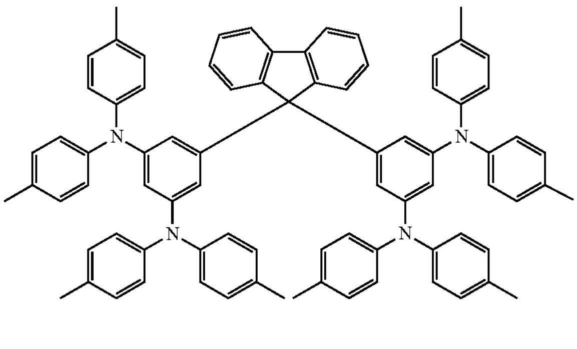
(55)
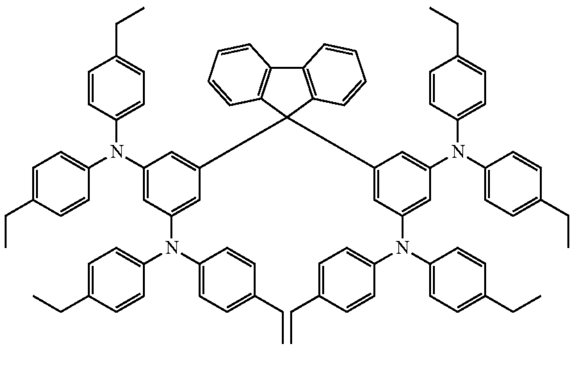

-continued
(56)
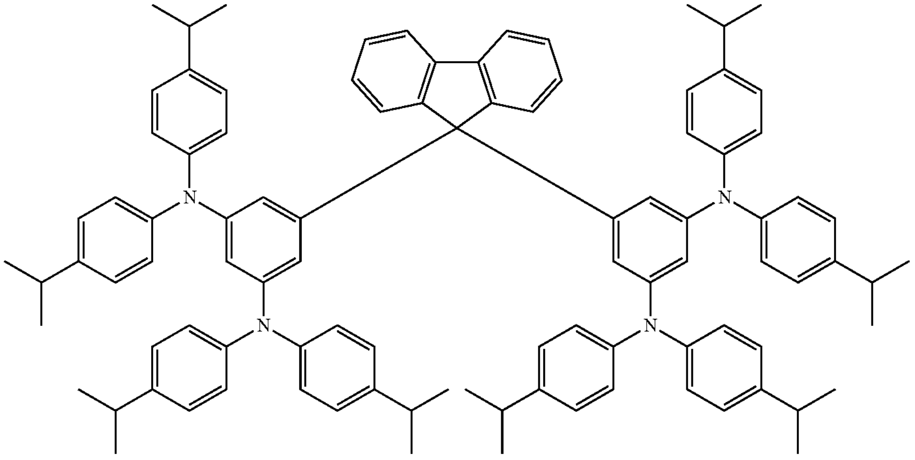
(57)
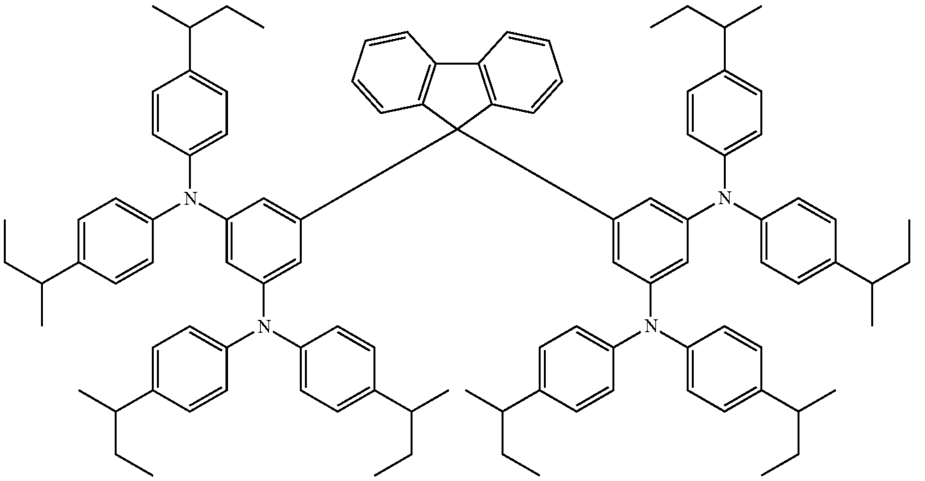
(58)
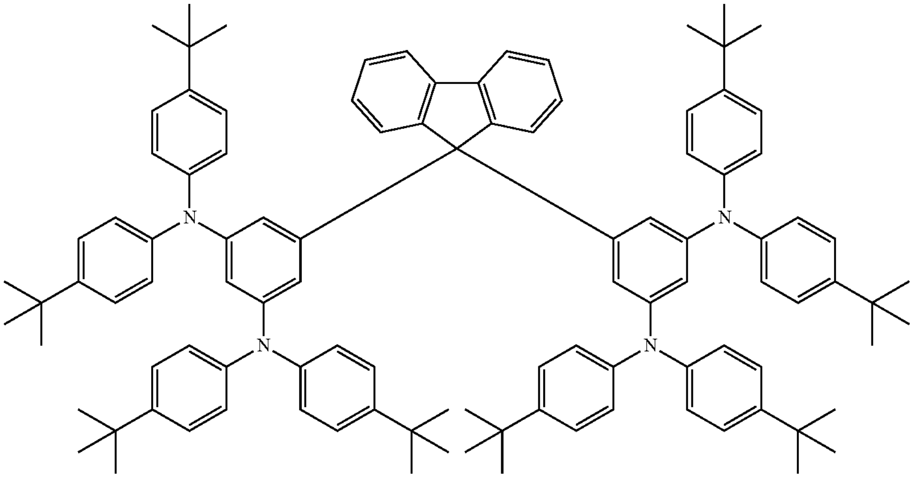

-continued
(59)
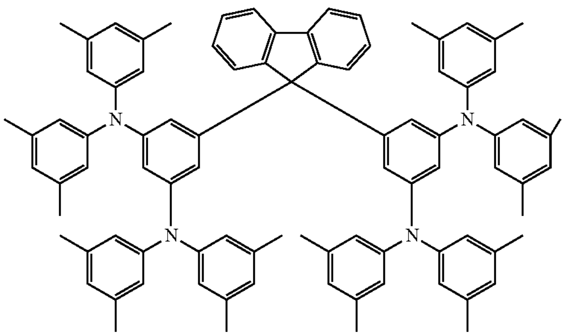
(60)
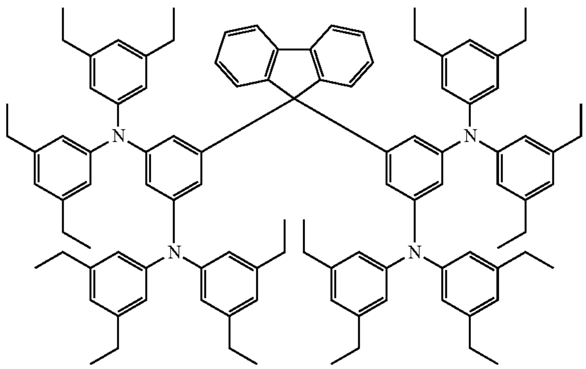
(61)
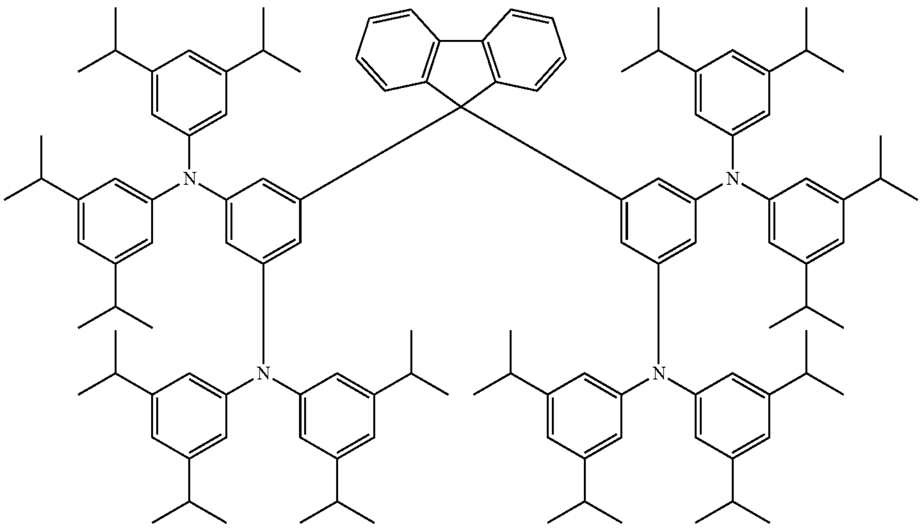
(62)
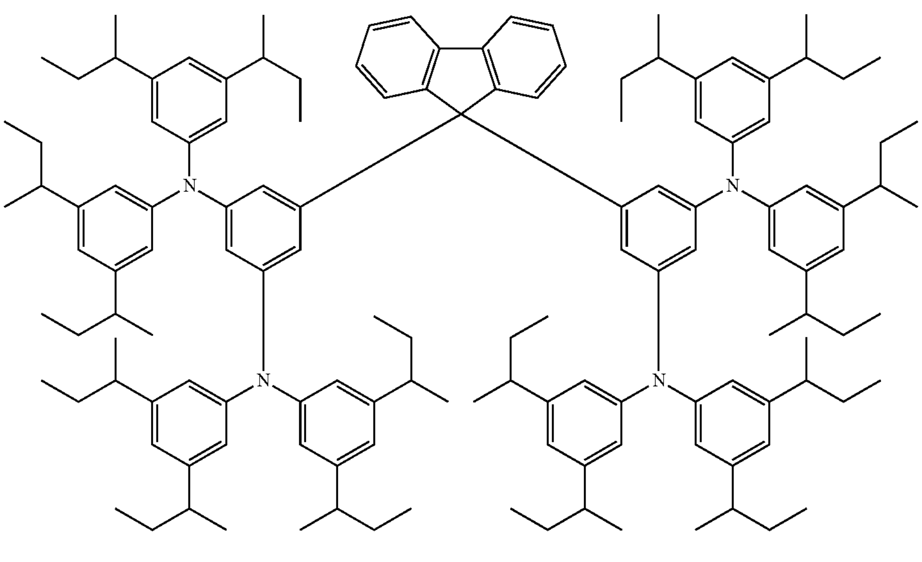

-continued
(63)
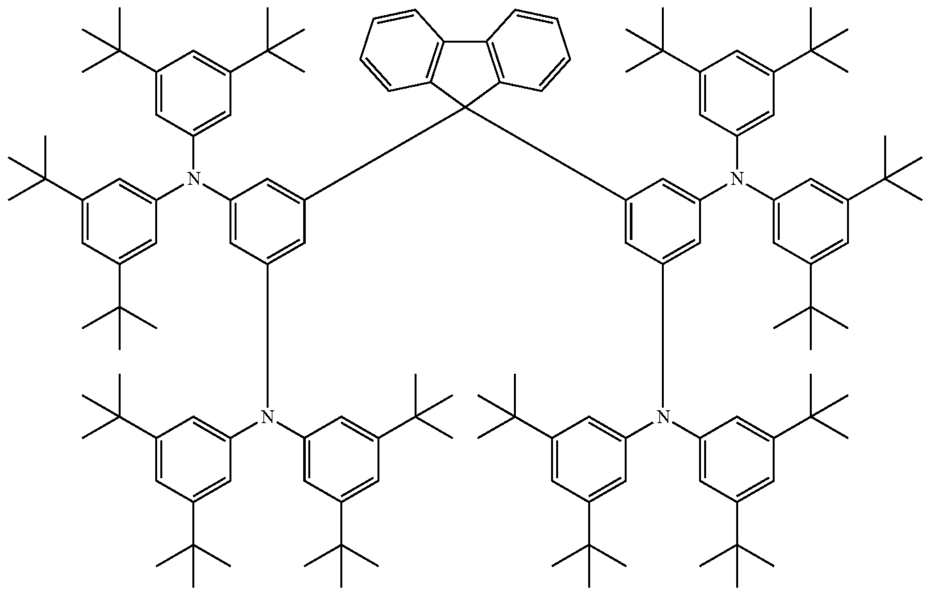
(64)
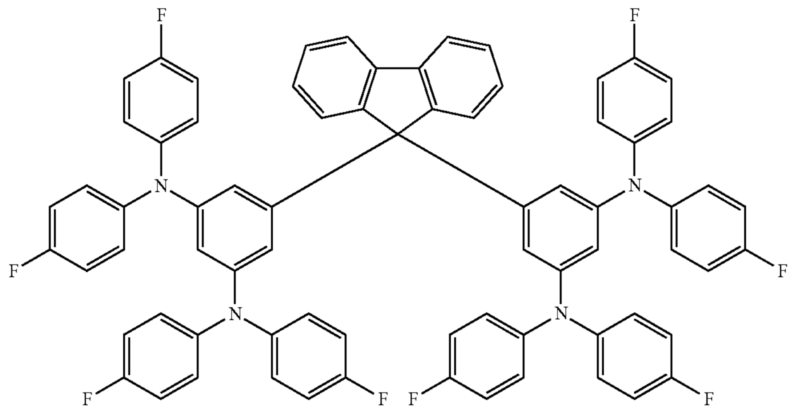
(65)
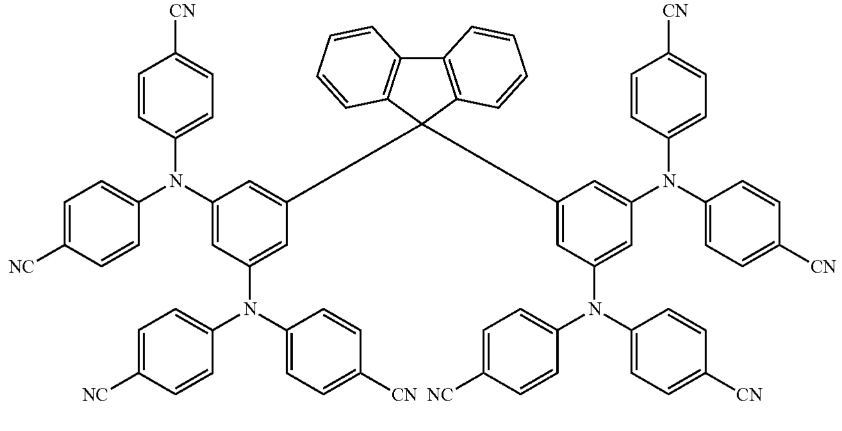

-continued
(66)
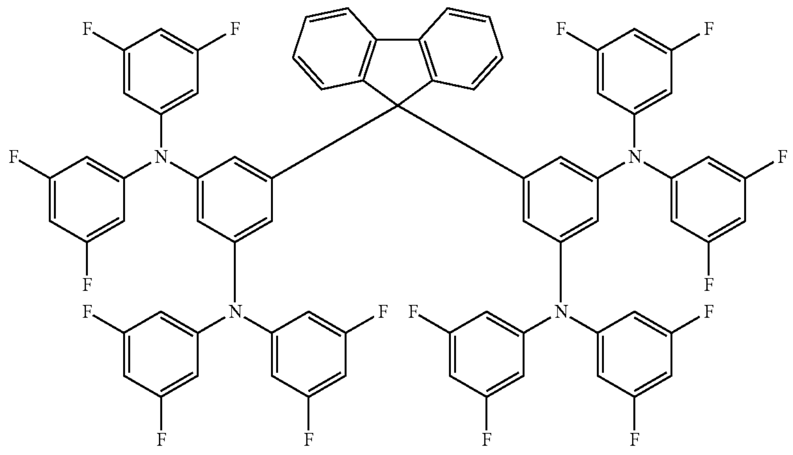
(67)
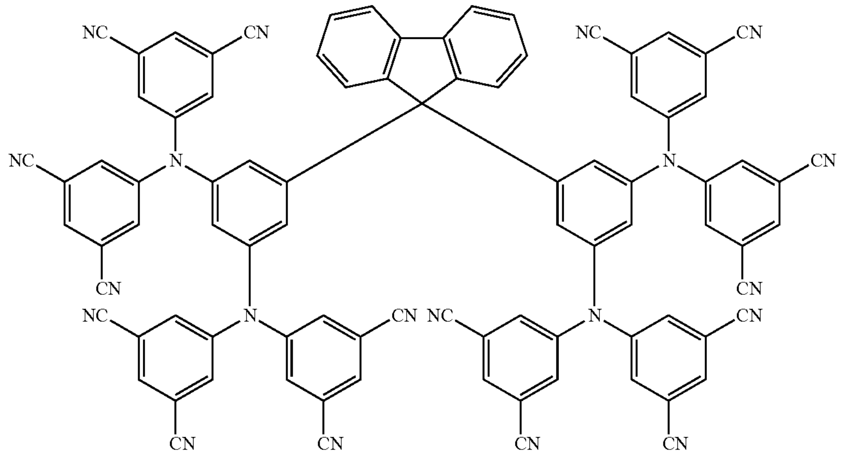
(68)
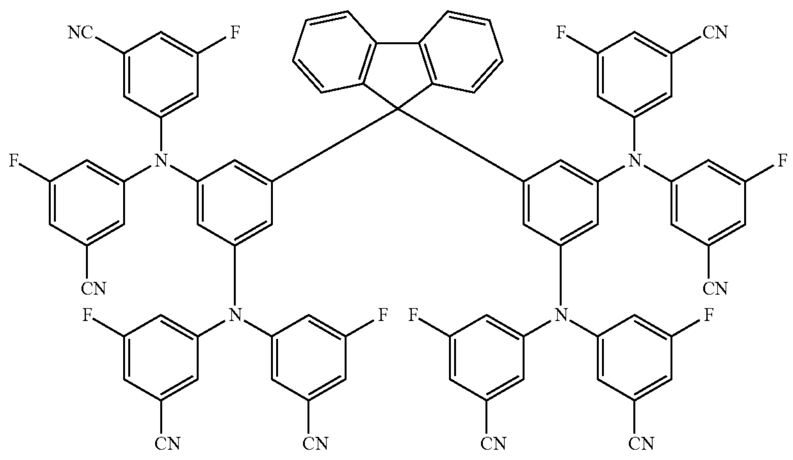

-continued
(69)
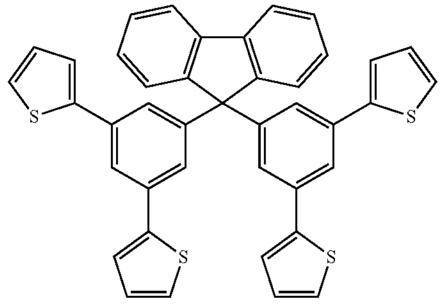
(70)
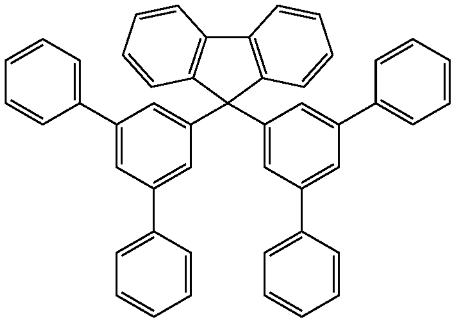
(71)
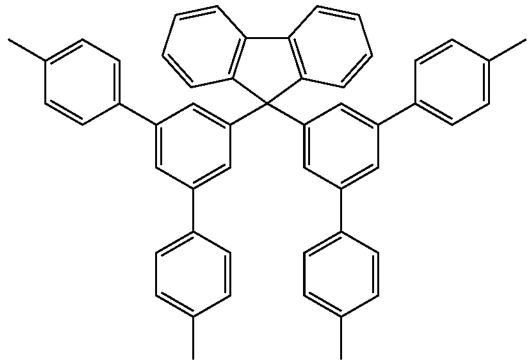
(72)
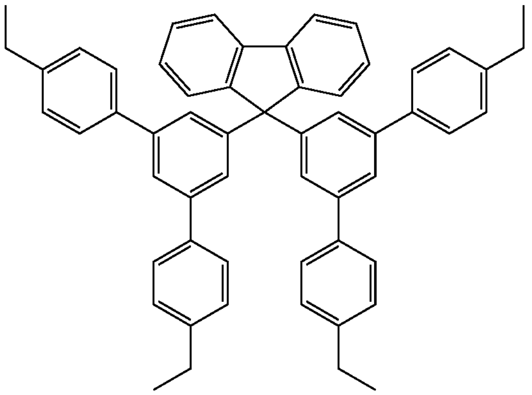
(73)
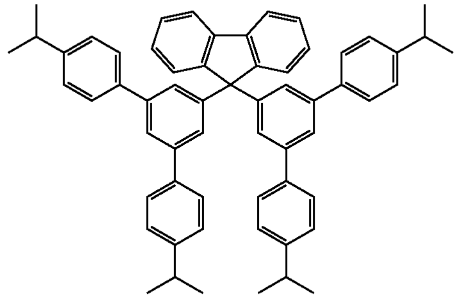
(74)
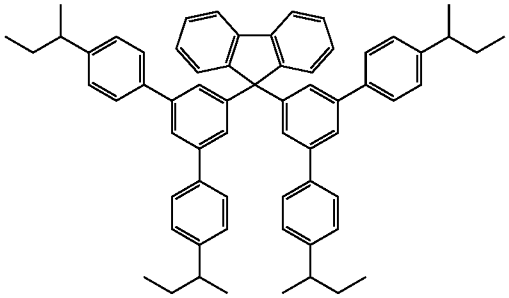
(75)
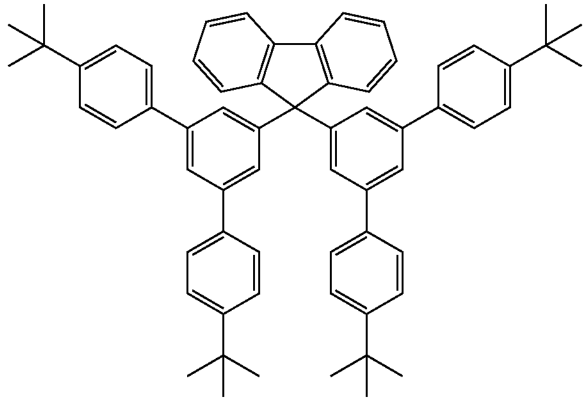
(76)
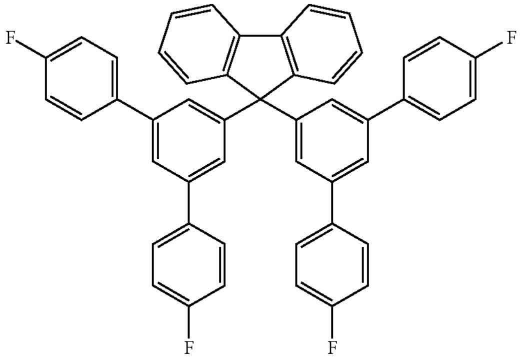

-continued
(77)
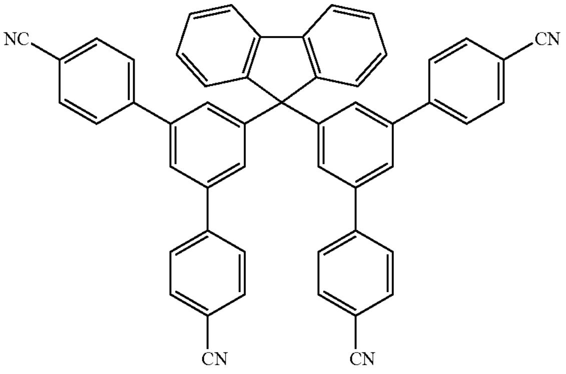
(78)
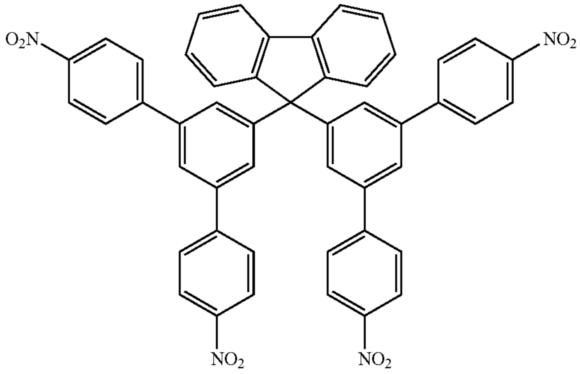
(79)
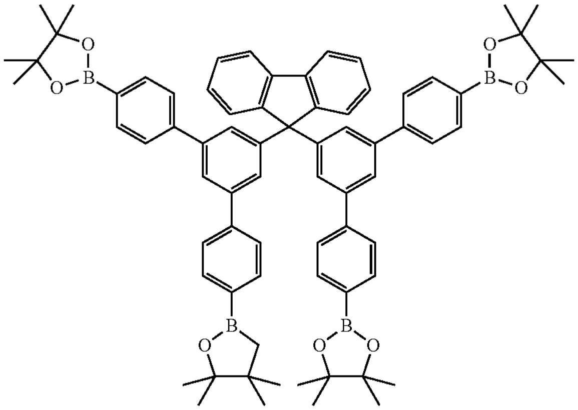
(80)
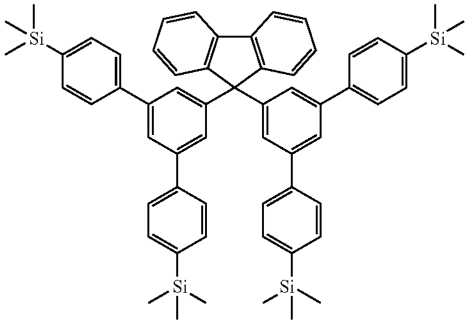
(81)
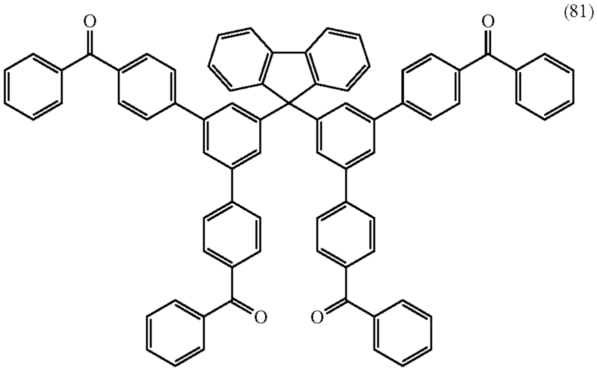
(82)
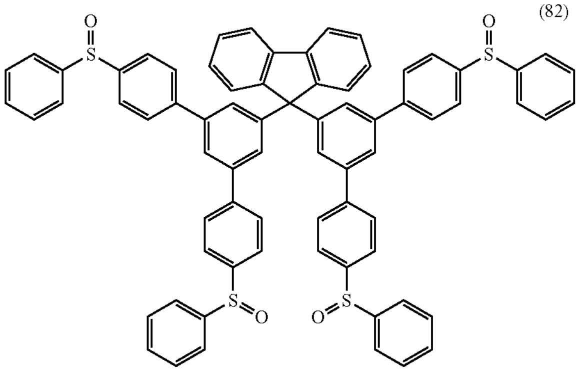
(83)
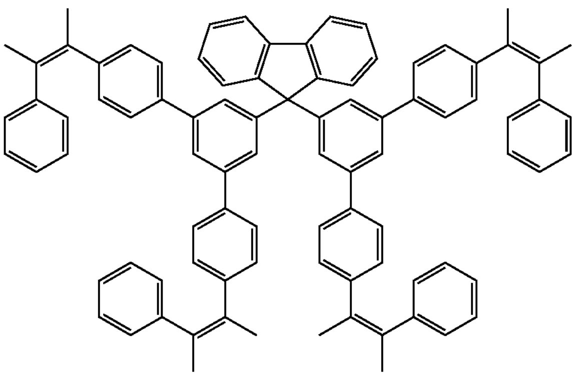
(84)
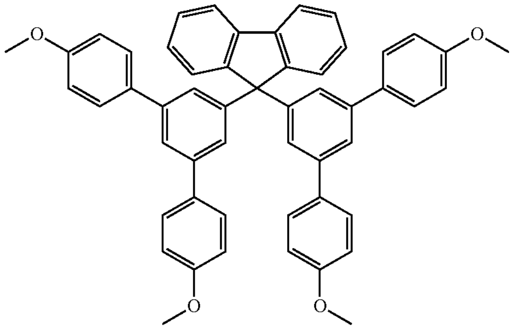

-continued
(85)
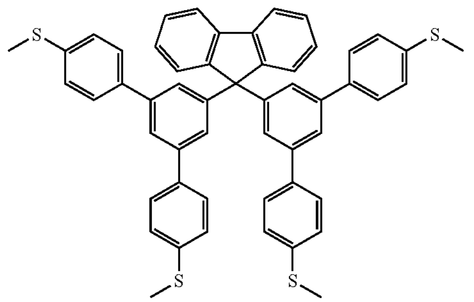
(86)
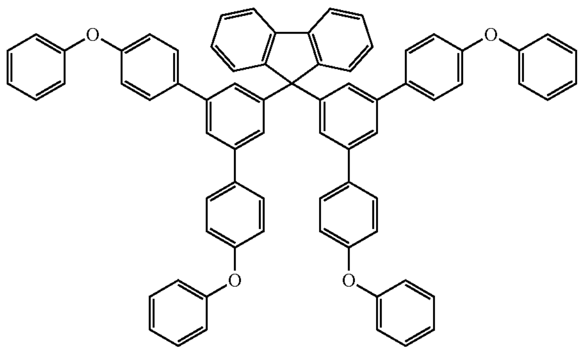
(87)
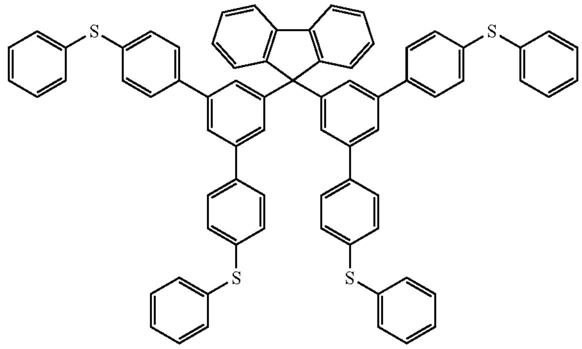
(88)
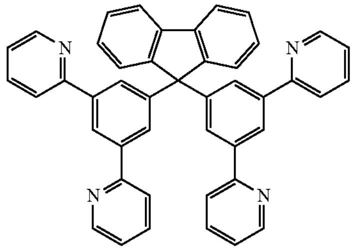
(89)
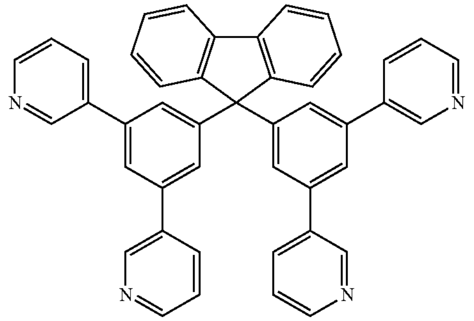
(90)
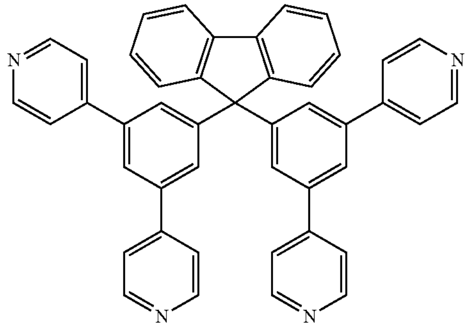
(91)
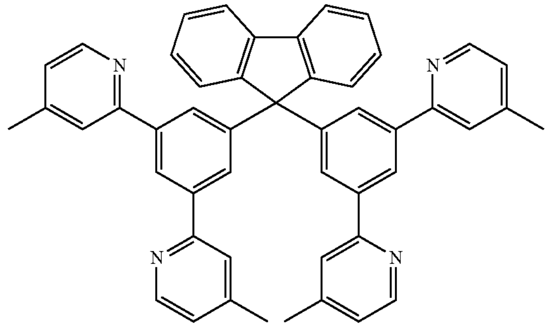
(92)
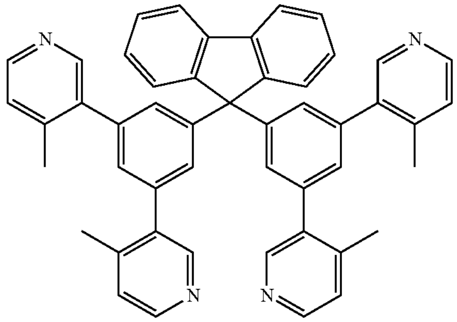

-continued
(93)
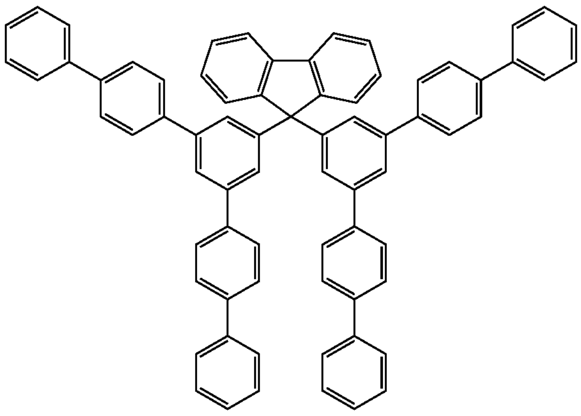
(94)
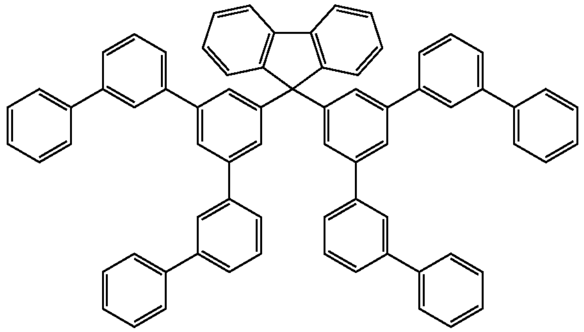
(95)
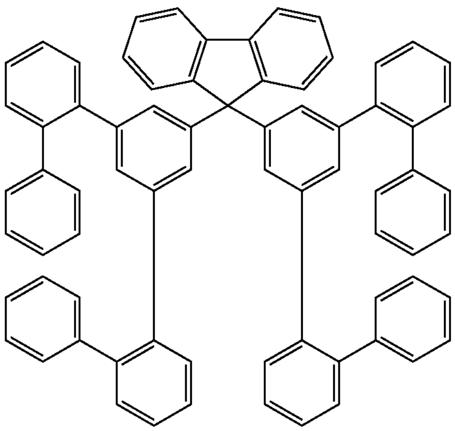
(96)
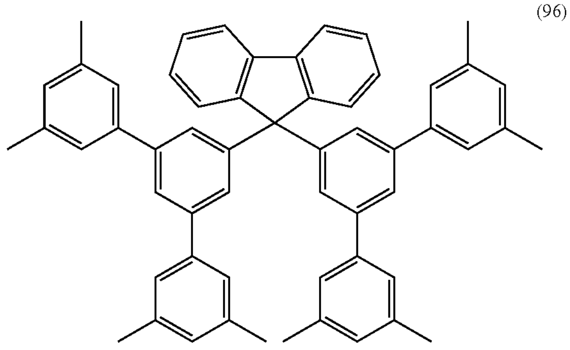
(97)
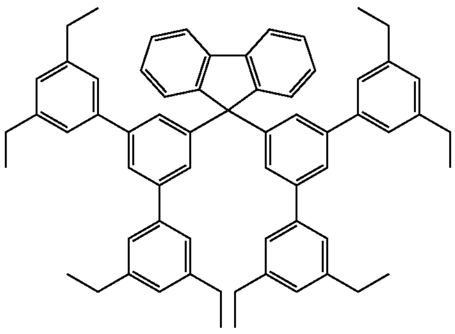
(98)
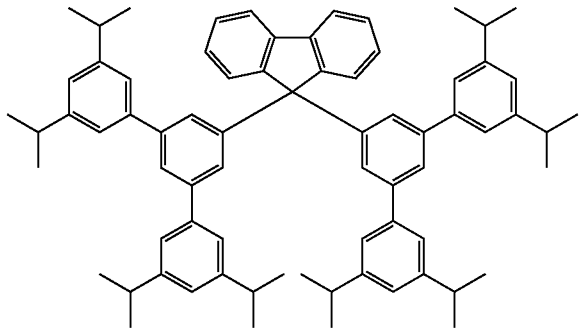
(99)
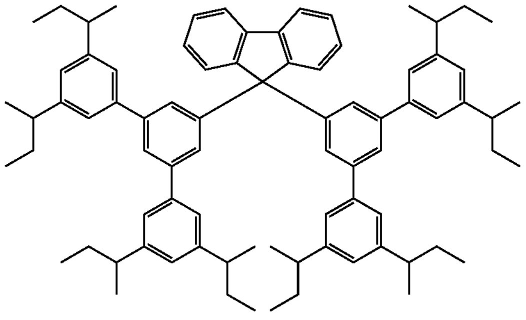
(100)
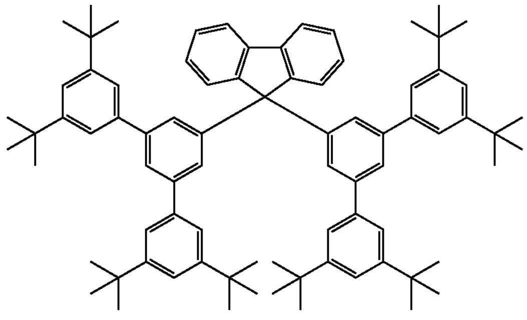

-continued
(101)
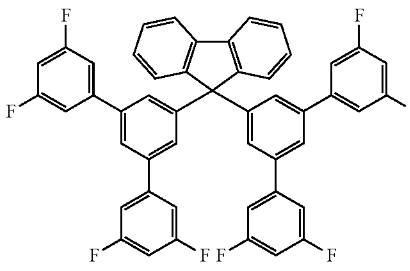
(102)
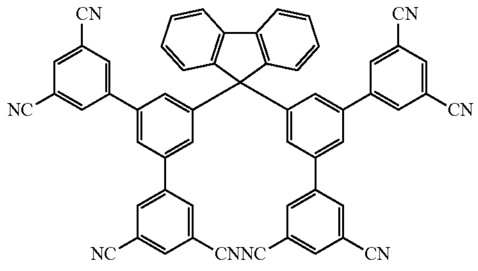
(103)
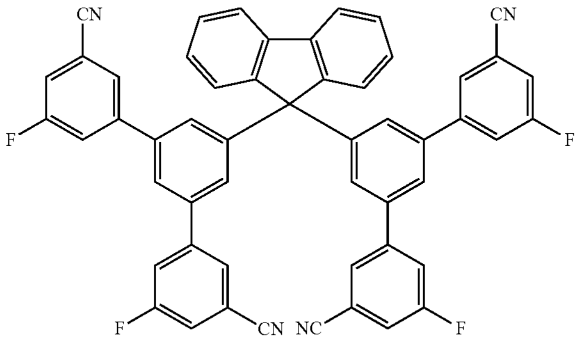
(104)
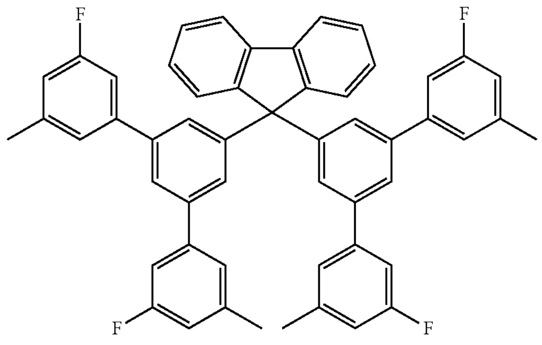
(105)
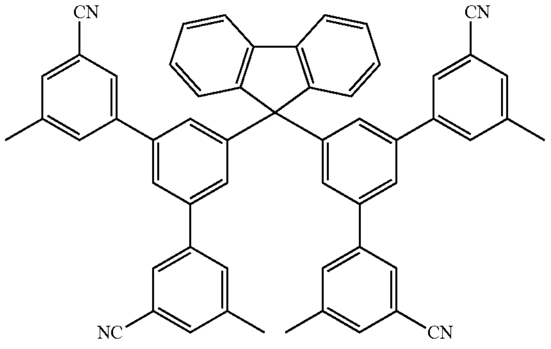
(106)
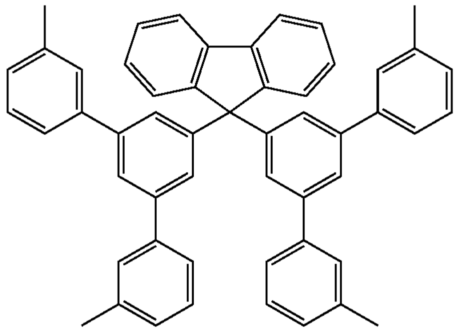
(107)
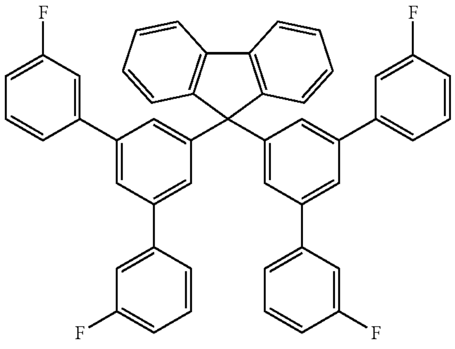
(108)
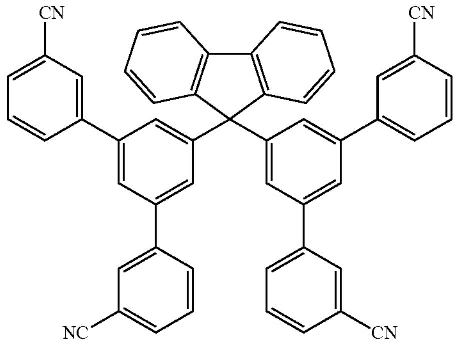
(109)
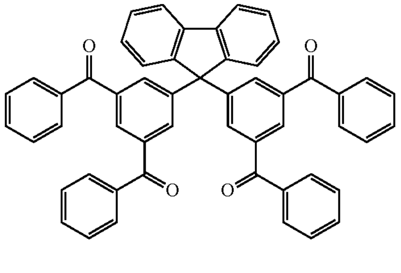
(110)
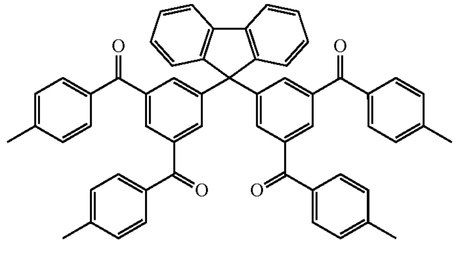

-continued
(111)
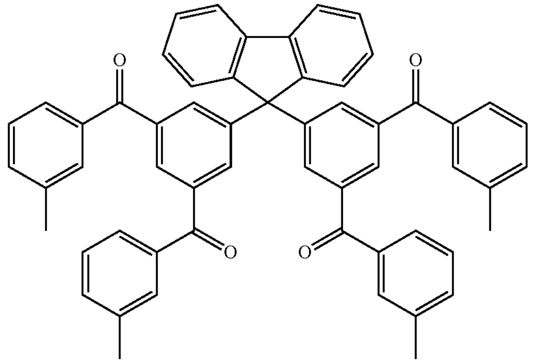
(112)
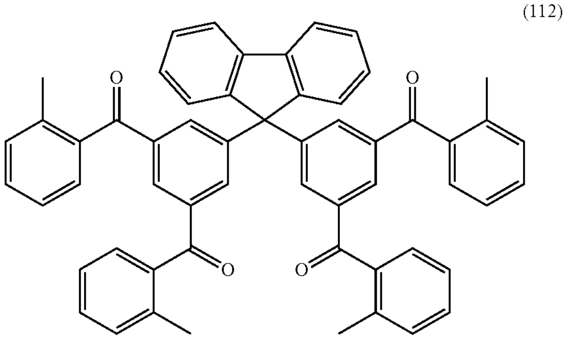
(113)
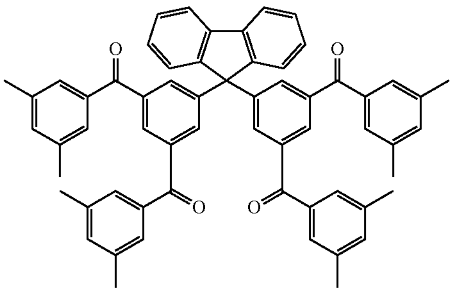
(114)
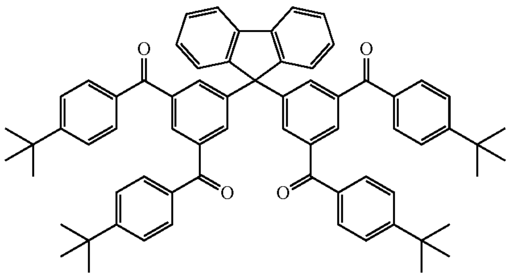
(115)
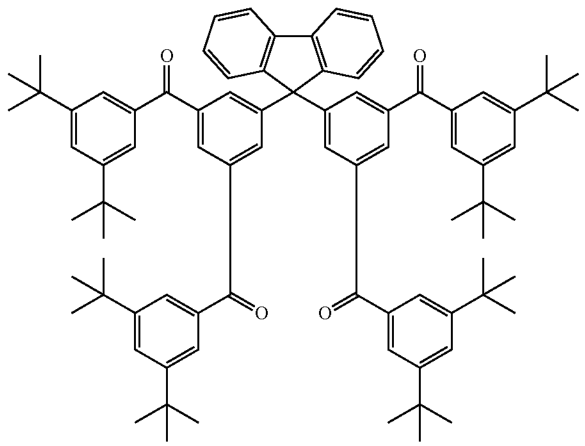
(116)
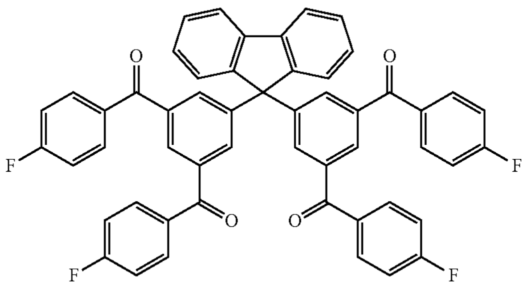
(117)
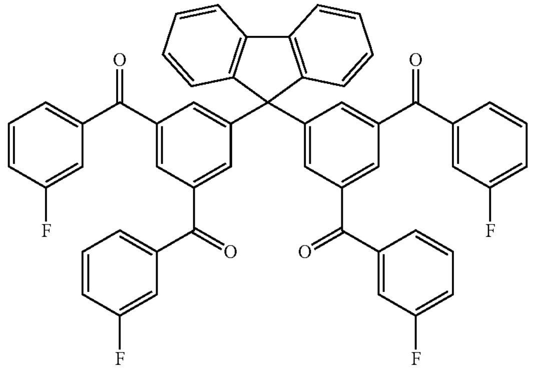
(118)
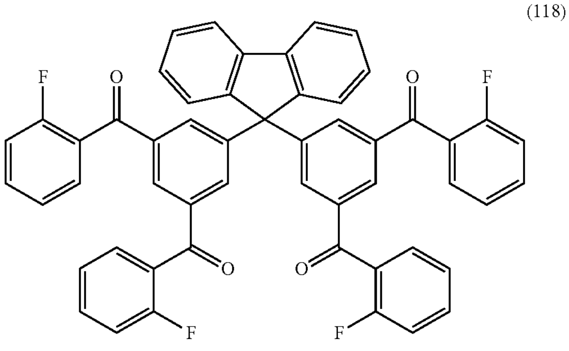

-continued
(119)
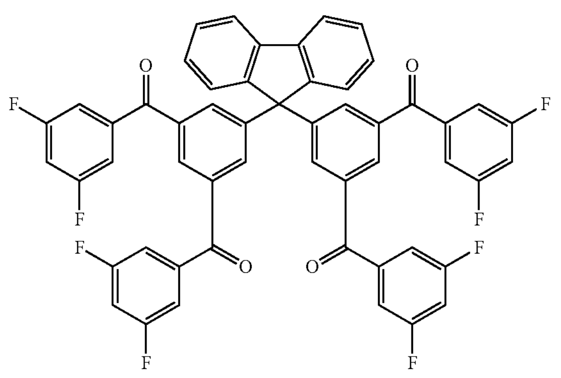
(120)
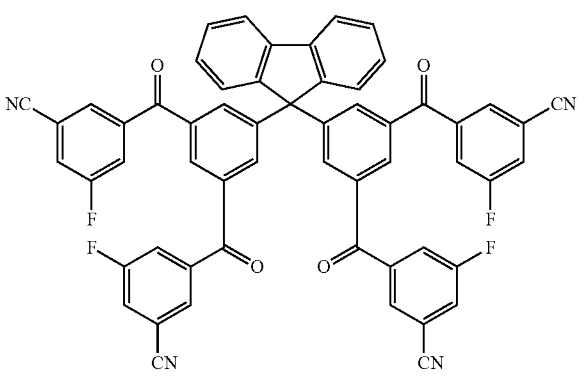
(121)
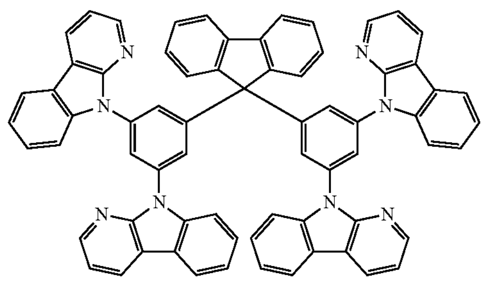
(122)
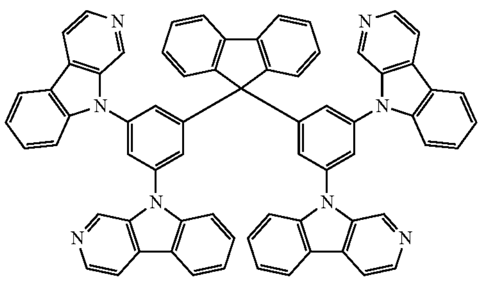
(123)
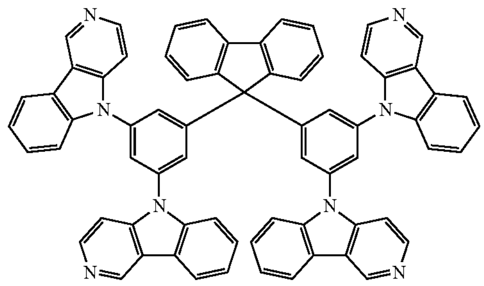
(124)
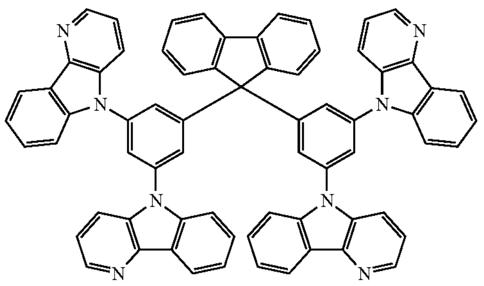
(125)
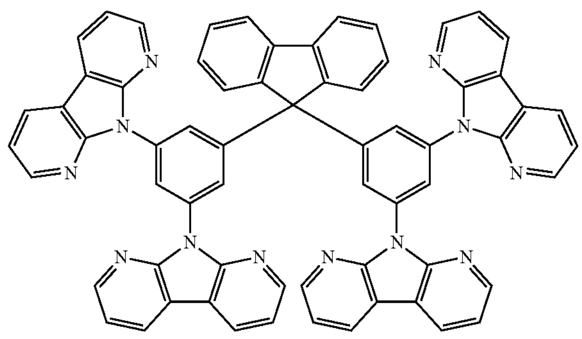
(126)
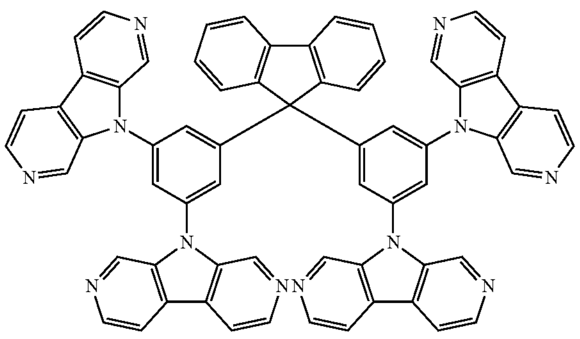

-continued
(127)
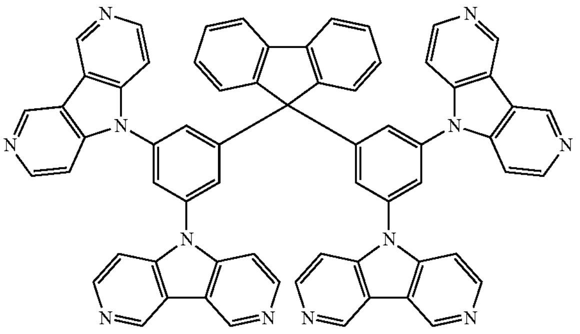
(128)
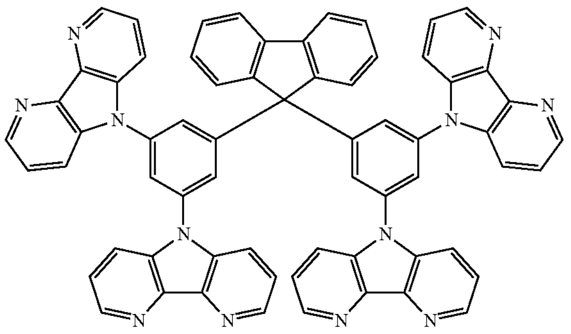
(129)
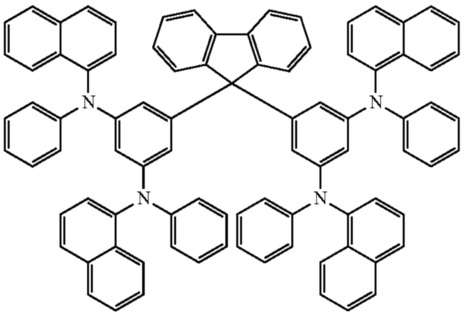
(130)
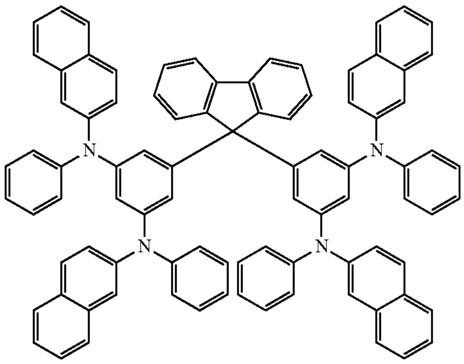
(131)
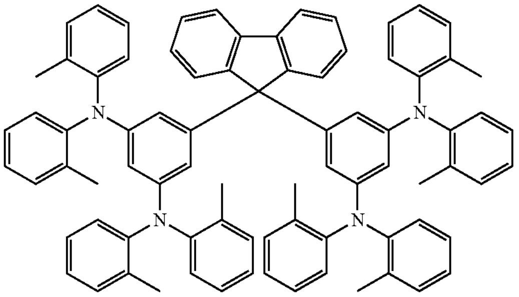
(132)
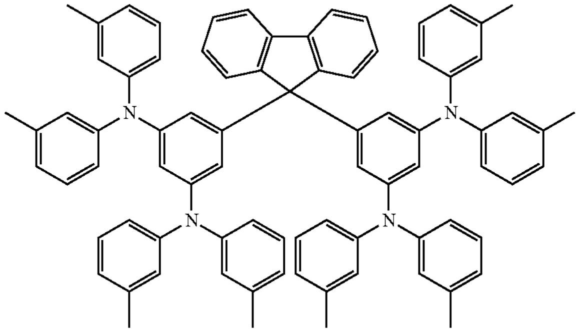
(133)
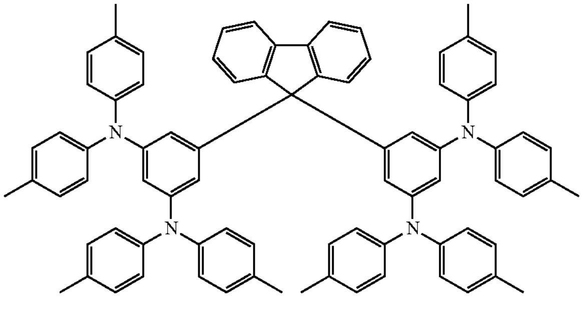
(134)
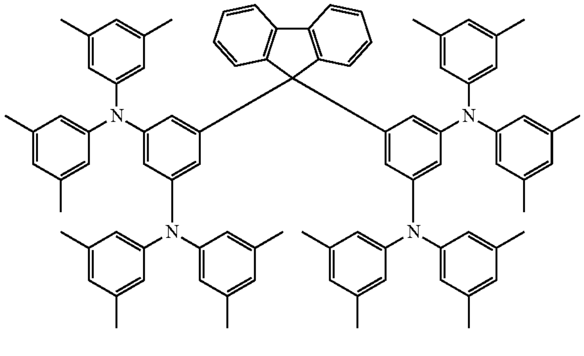

-continued
(135)
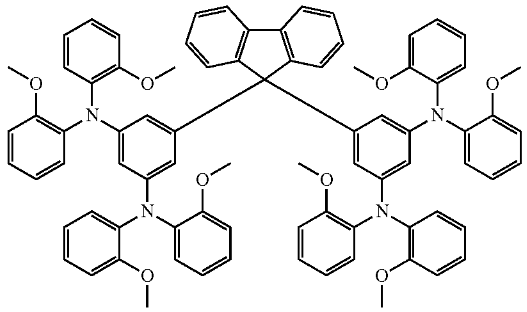
(136)
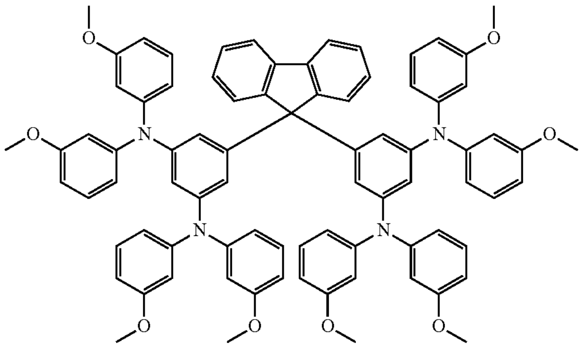
(137)
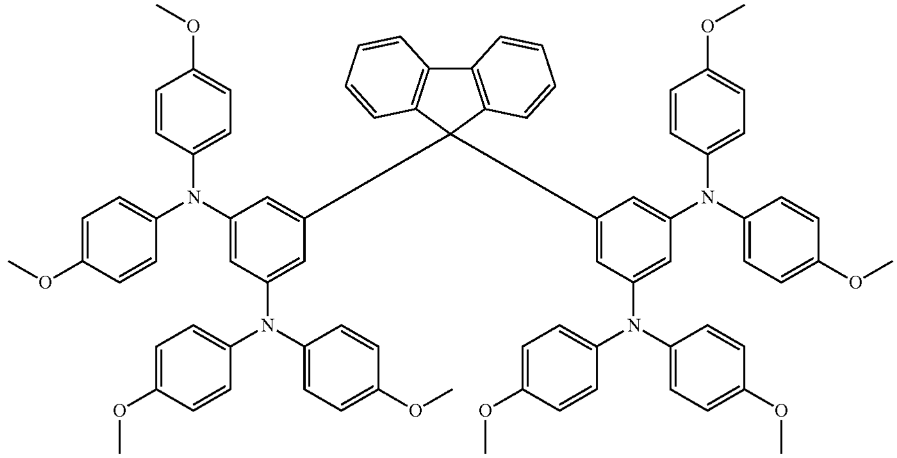
(138)
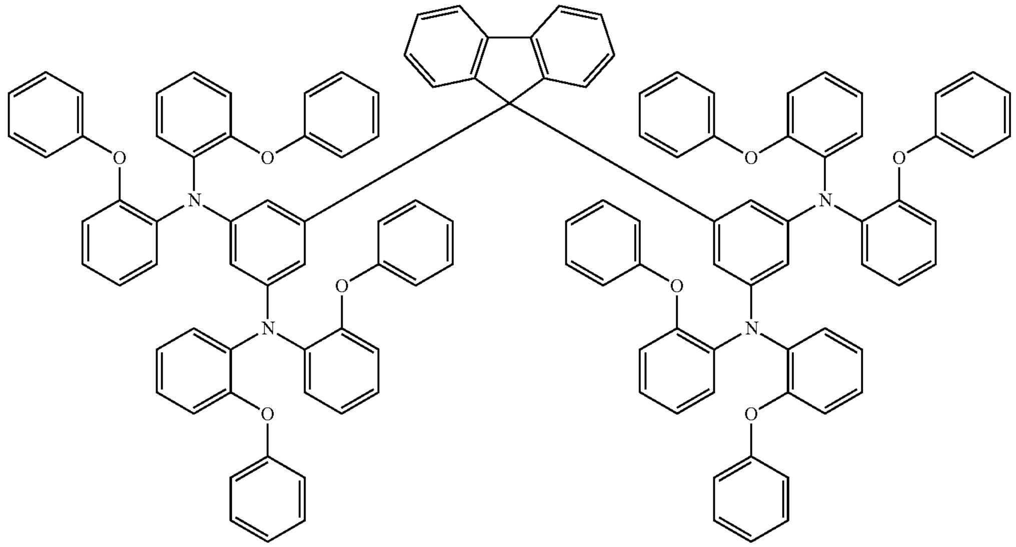

-continued
(139)
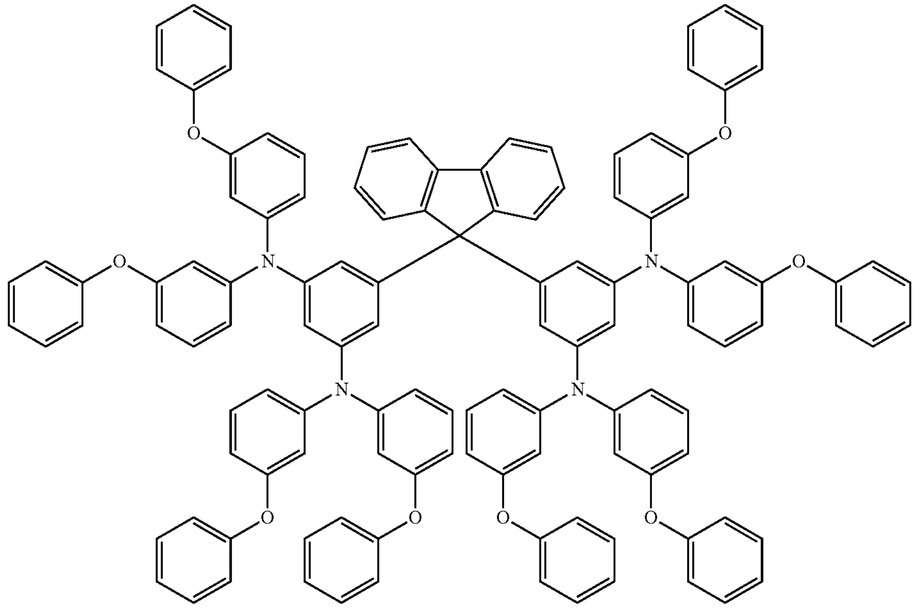
(140)
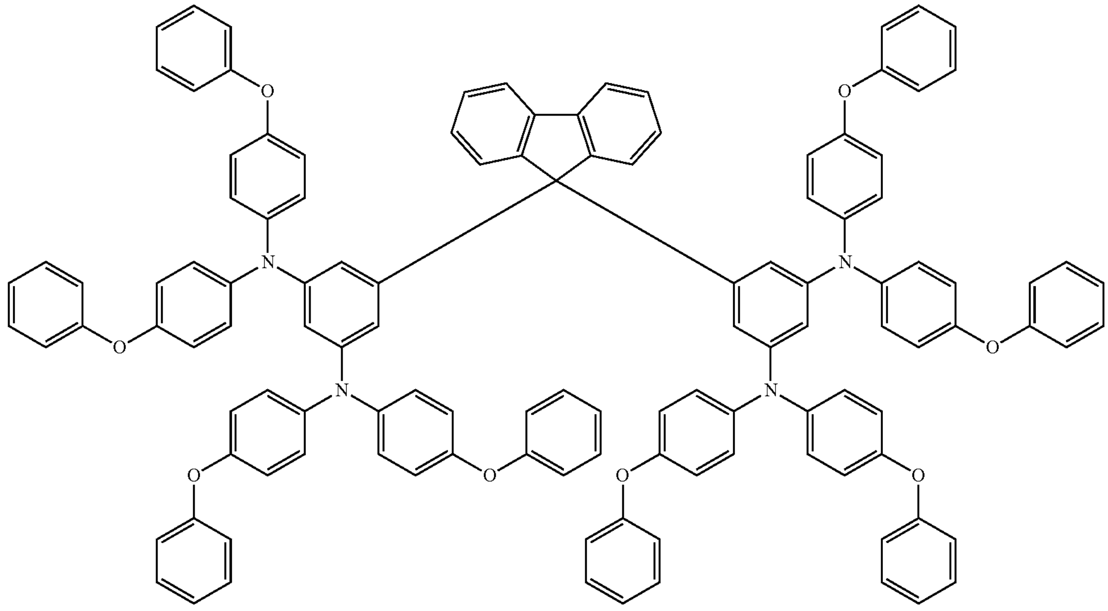

-continued
(141)
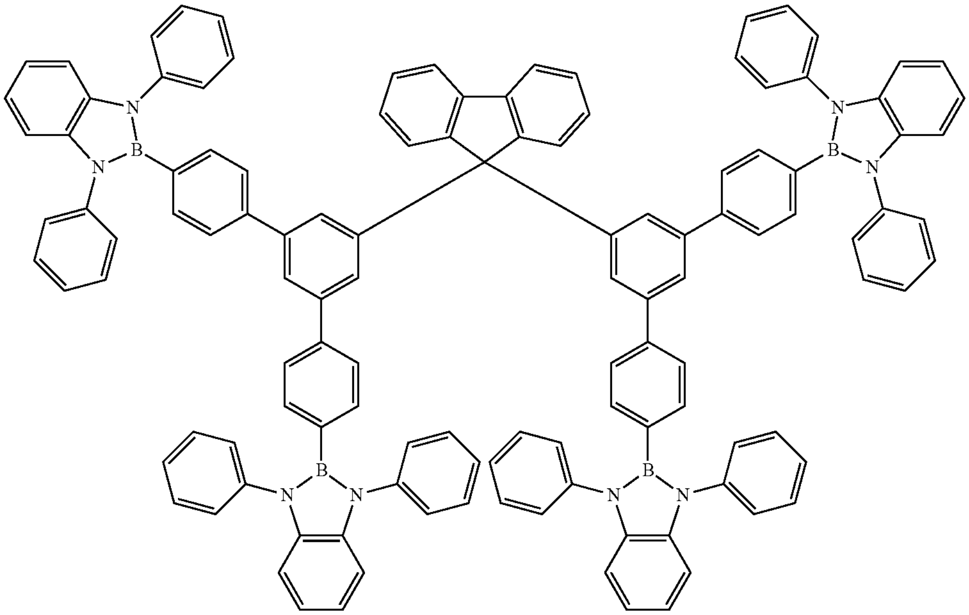
(142)
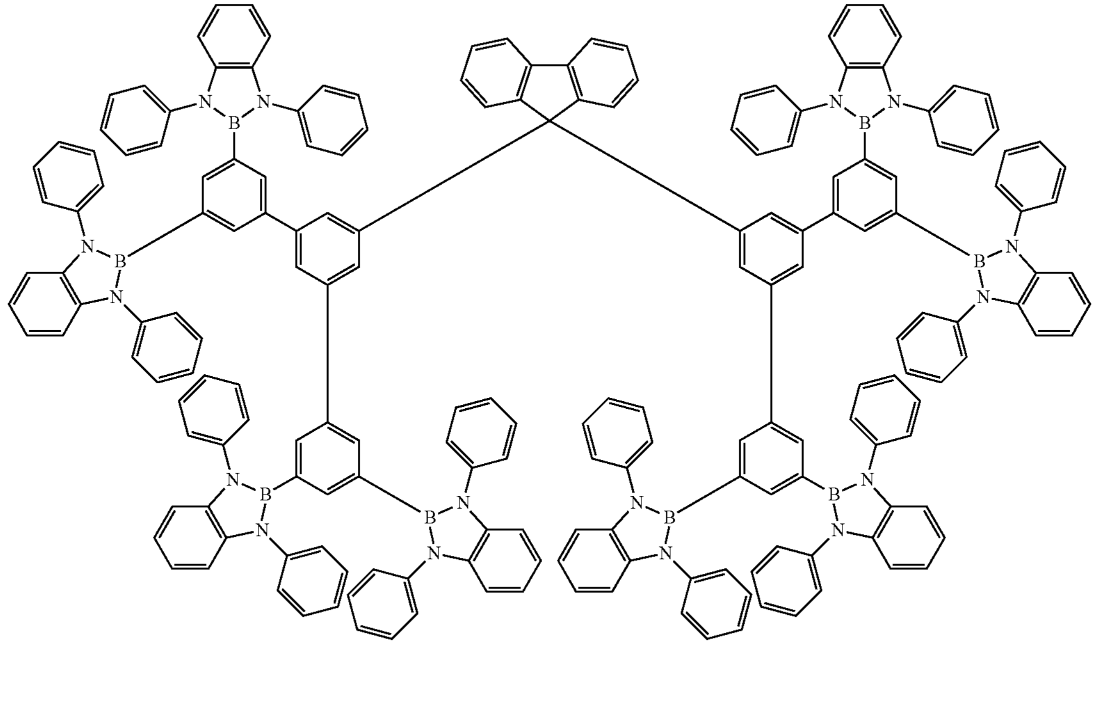

-continued
(143)
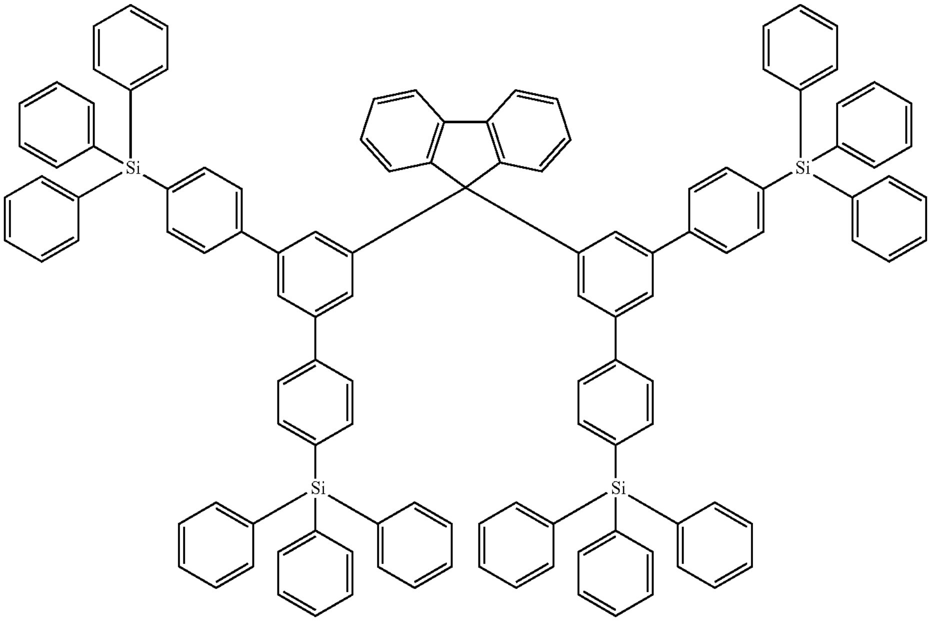
(144)
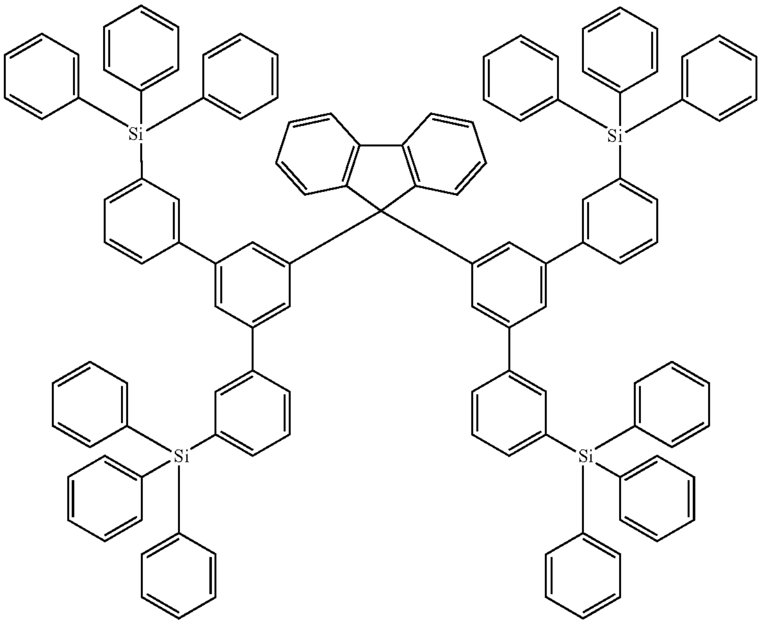

-continued
(145)
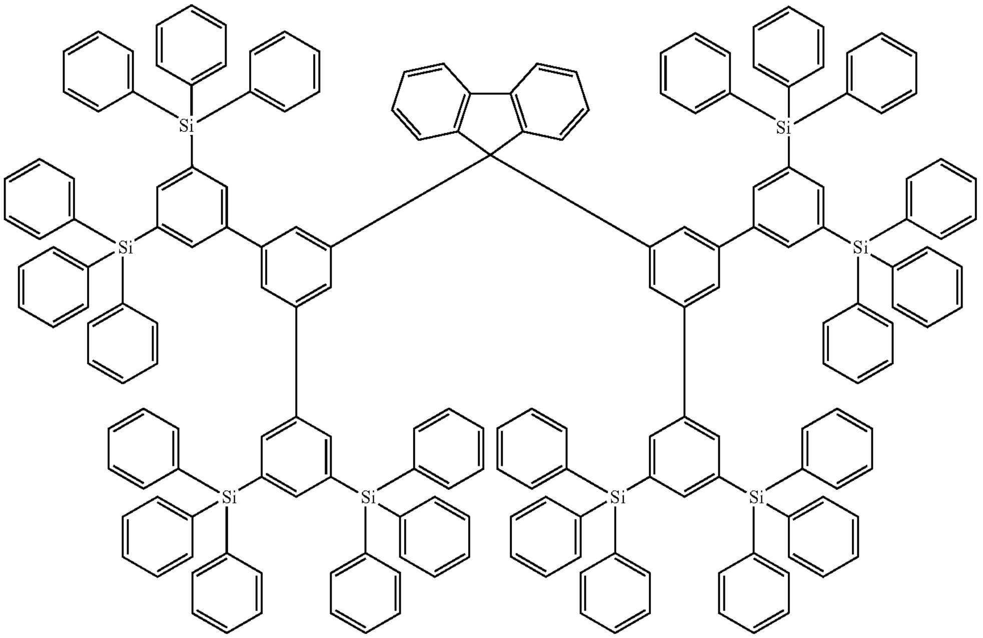
(146)
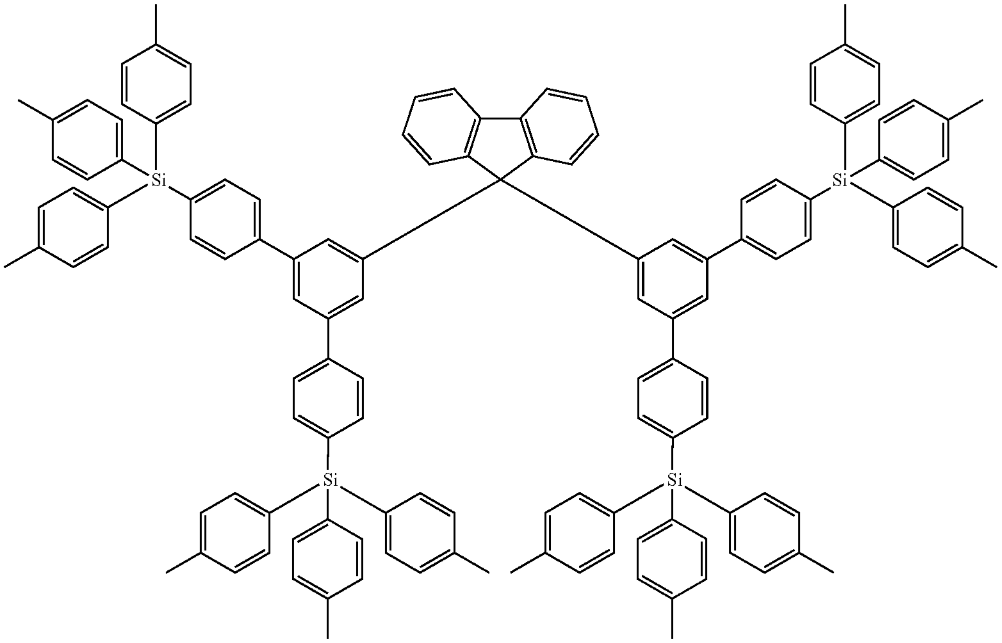

-continued
(147)
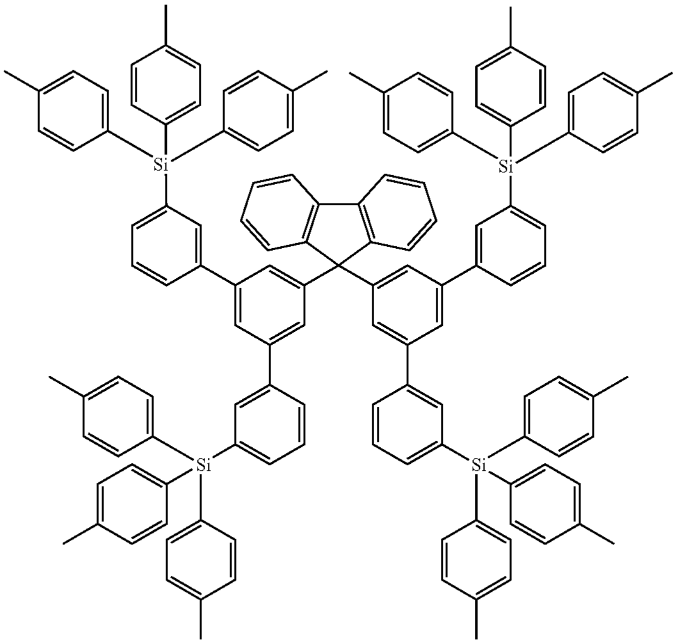
(148)
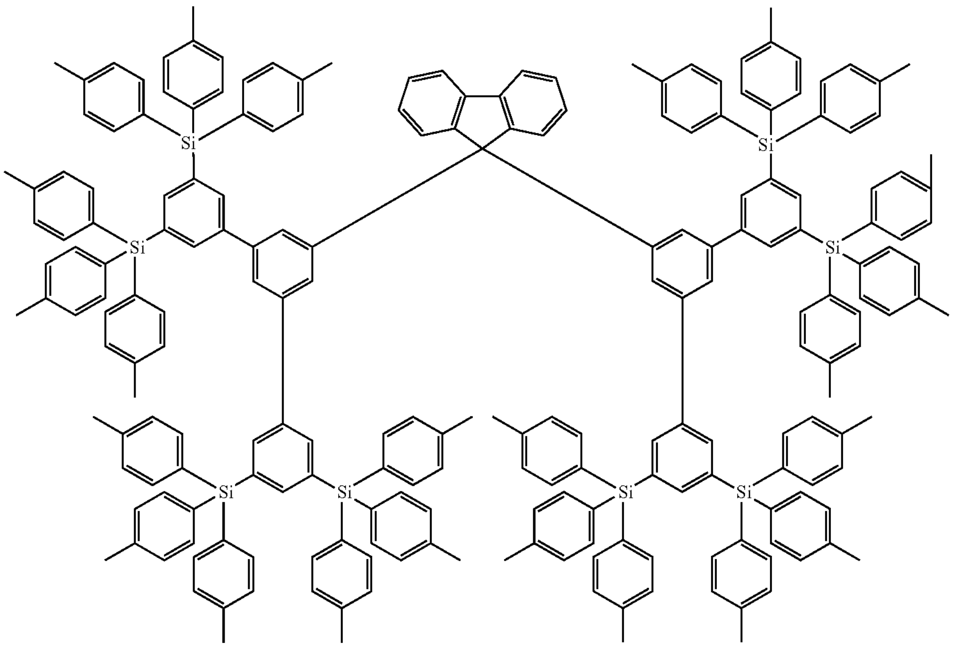

-continued
(149)
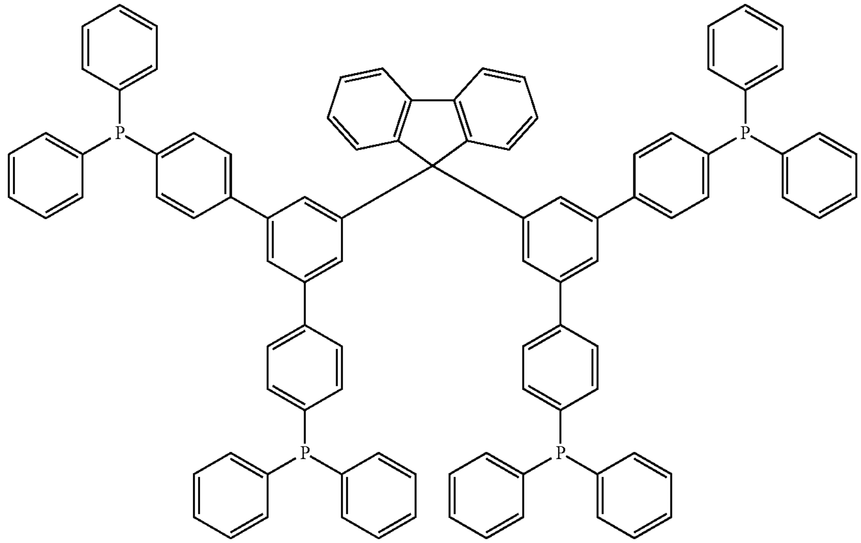
(150)
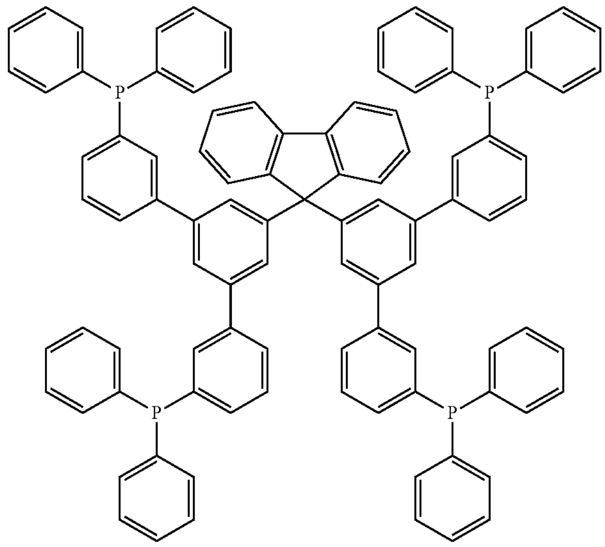

-continued
(151)
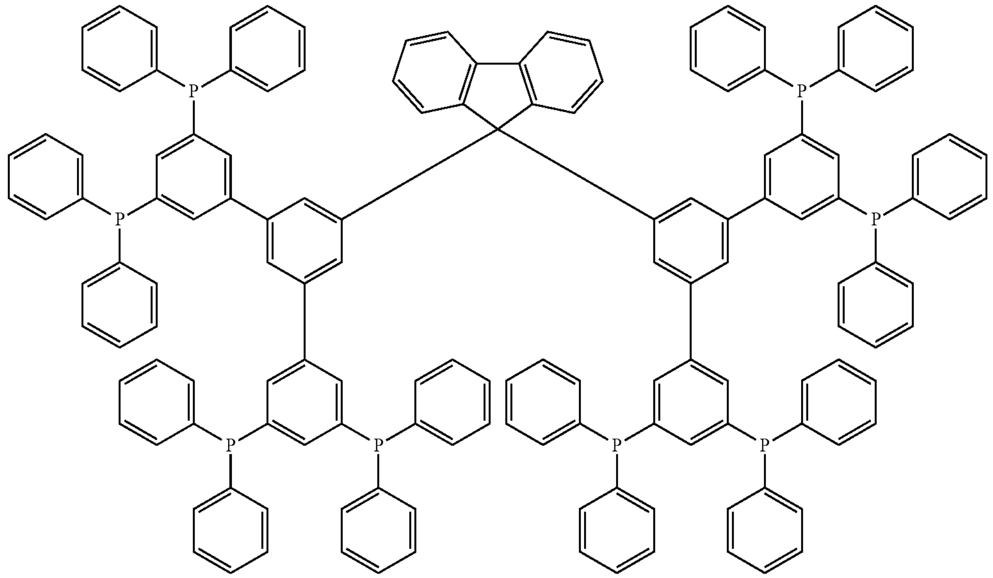
(152)
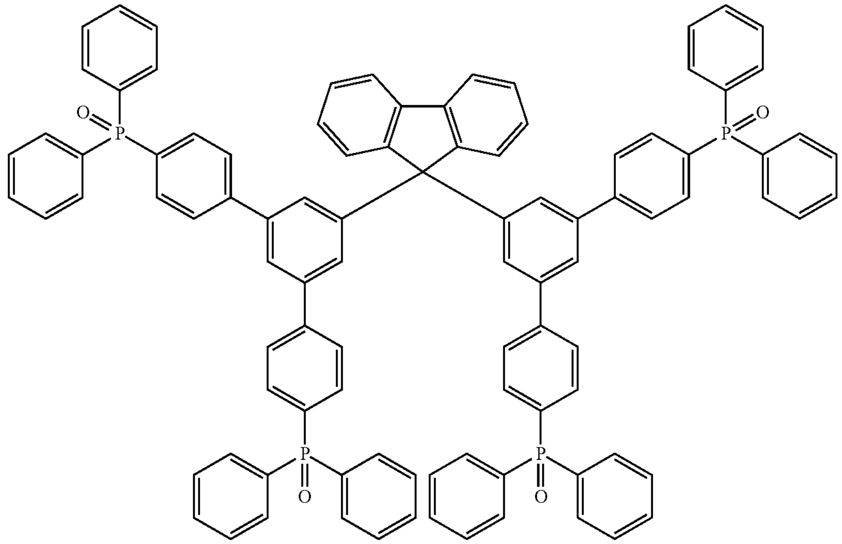

-continued
(153)
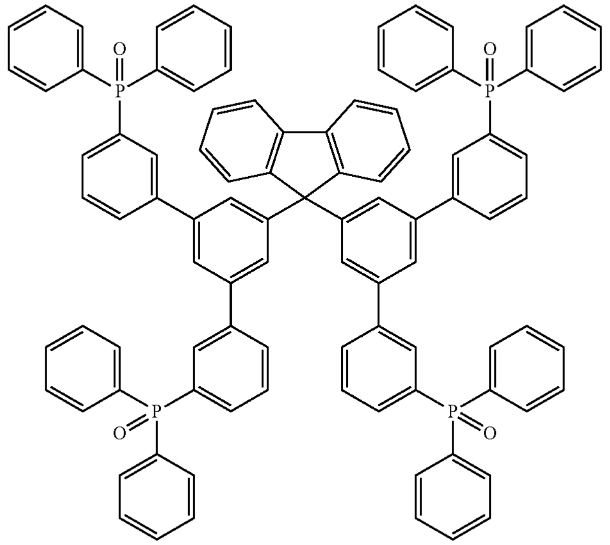
(154)
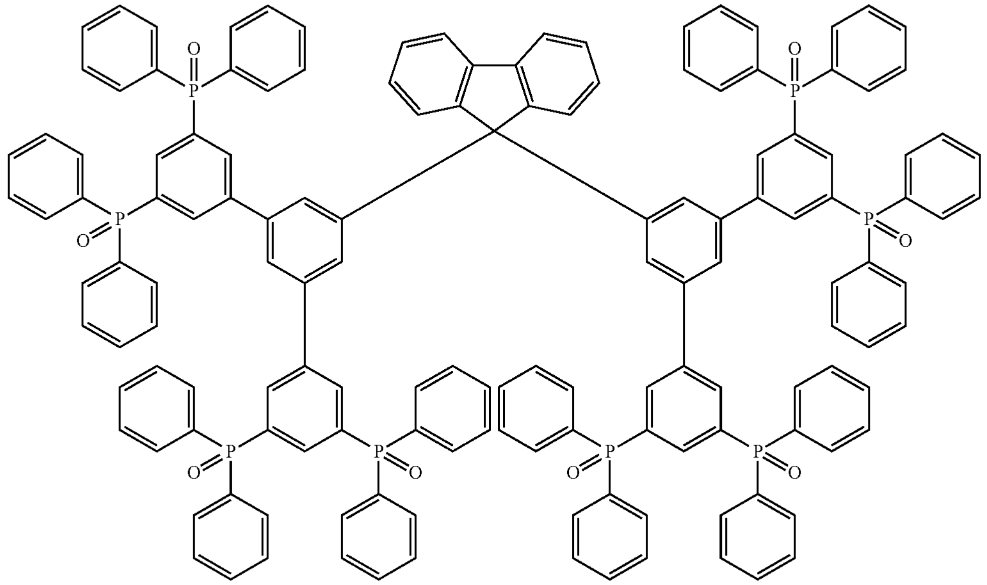
(155)
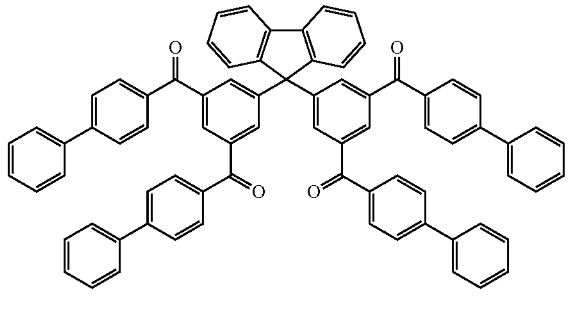
(156)
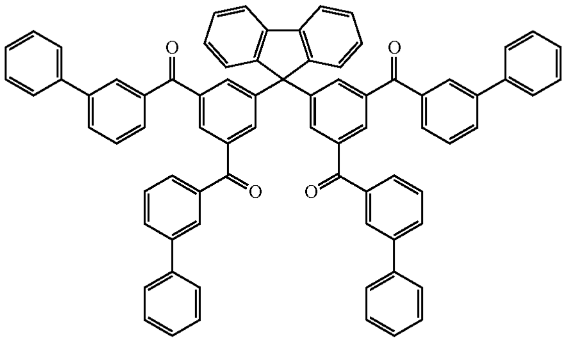

-continued
(157)
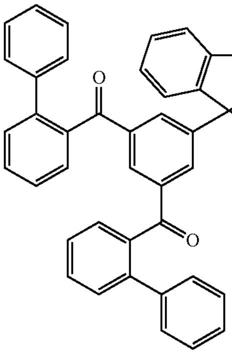
(158)
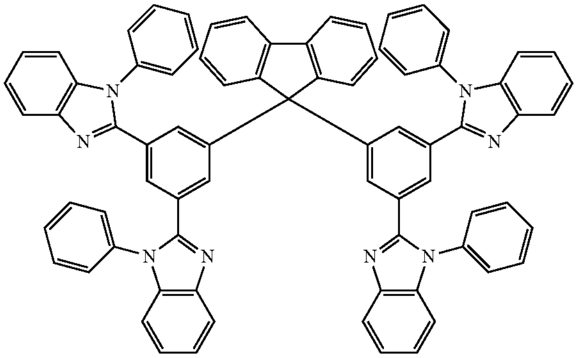
(159)
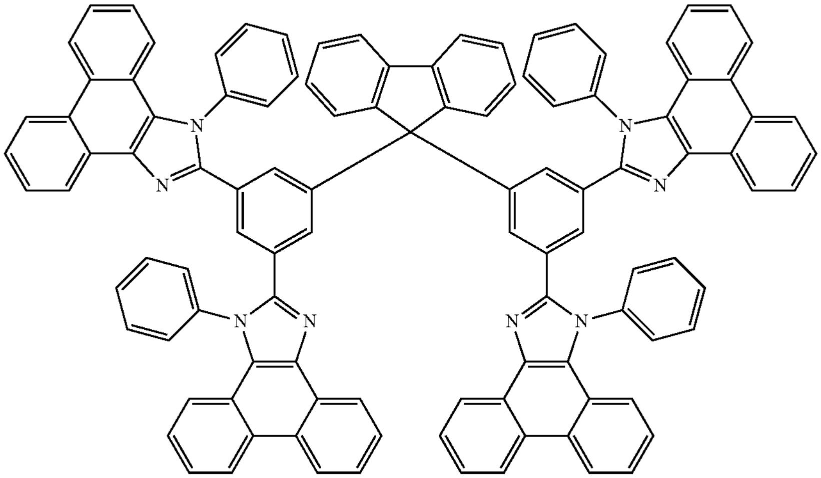
(160)
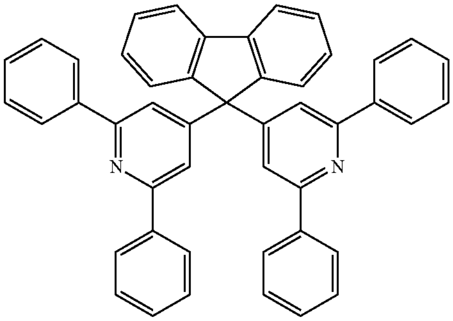
(161)
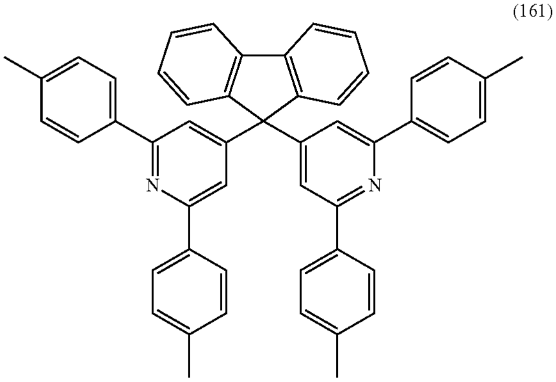
(162)
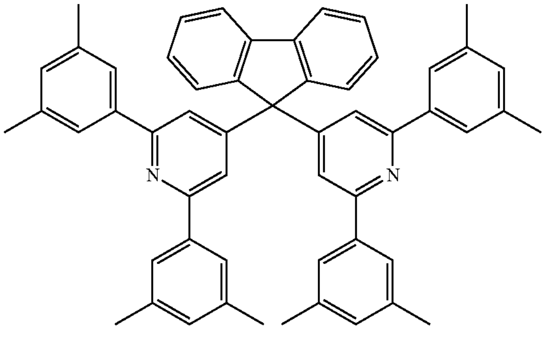
(163)
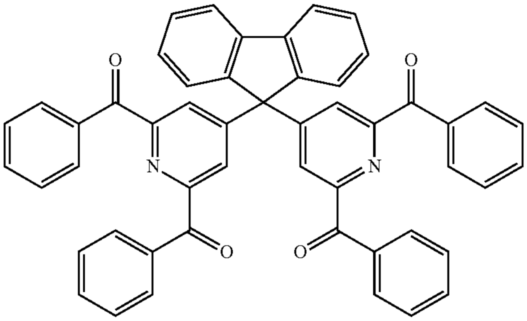

-continued
(164)
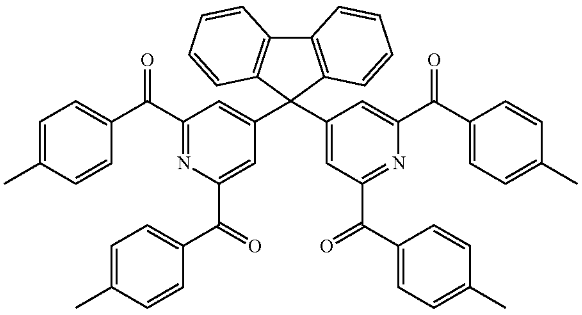
(165)
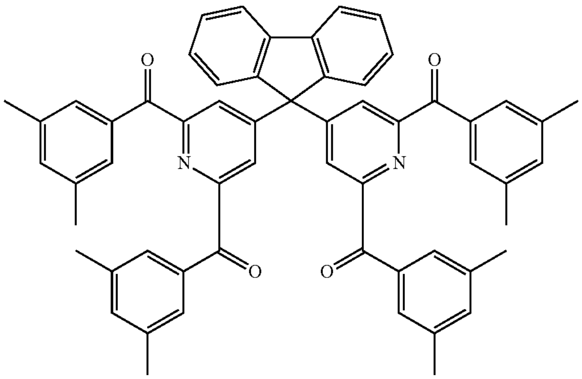
(166)
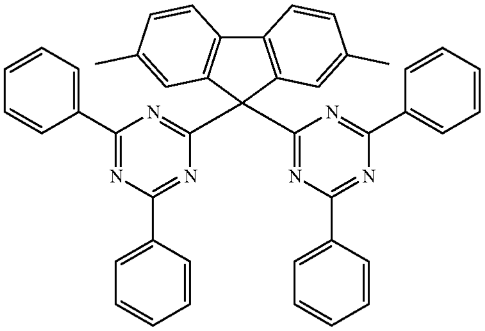
(167)
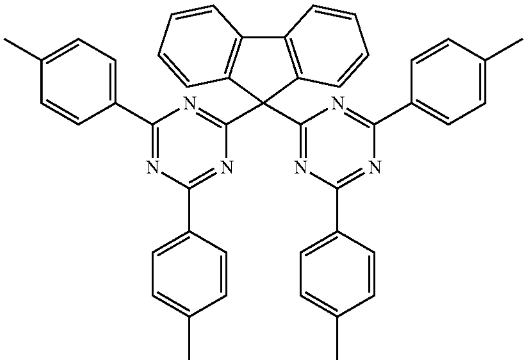
(168)
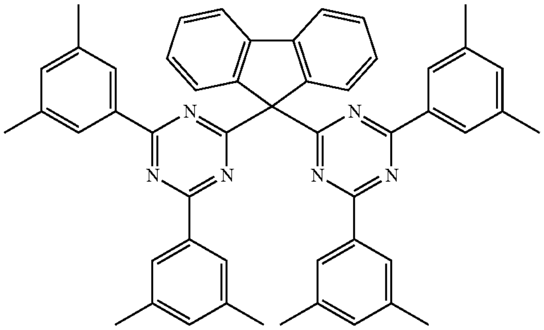
(169)
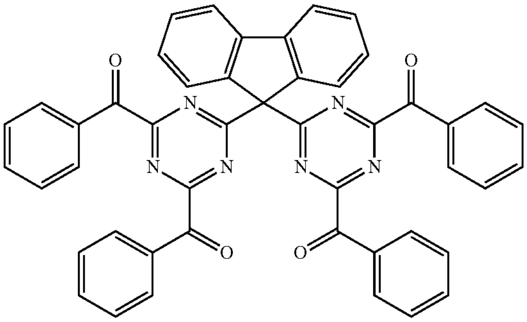
(170)
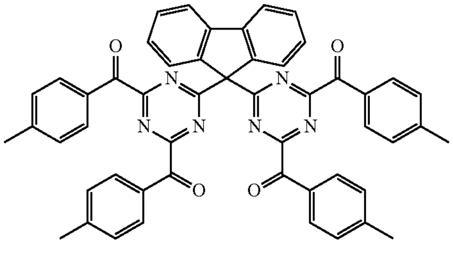
(171)
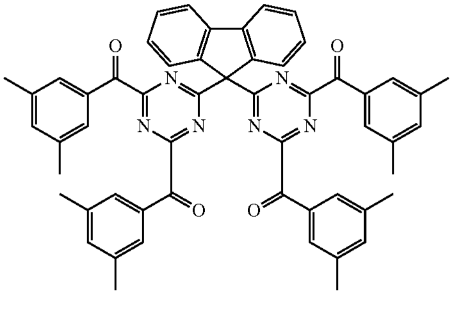

-continued
(172)
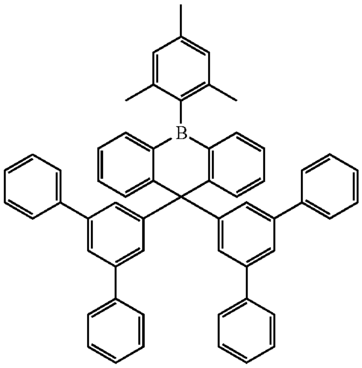
(173)
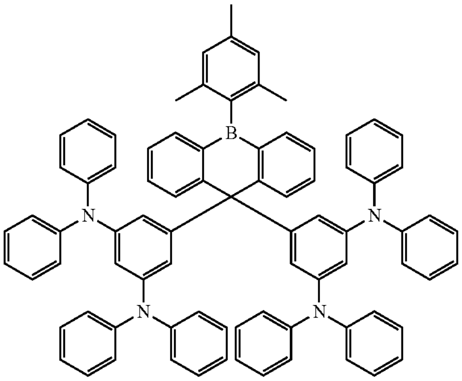
(174)
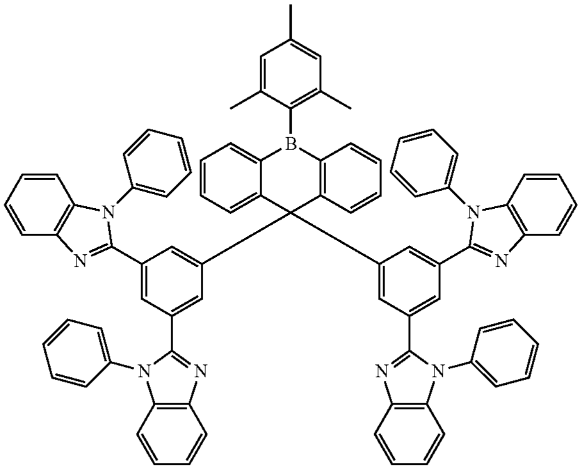
(175)
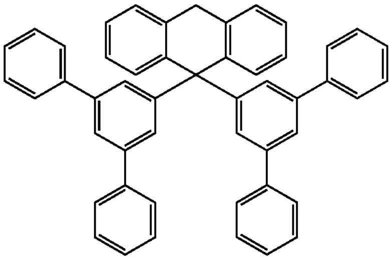
(176)
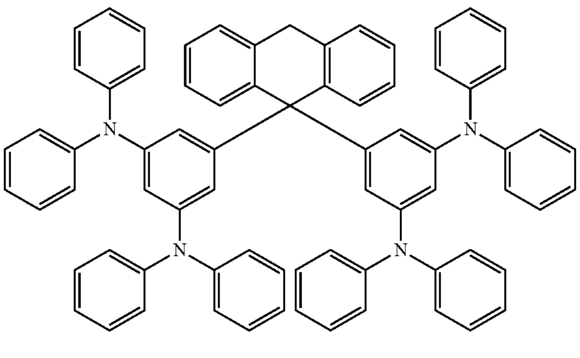
(177)
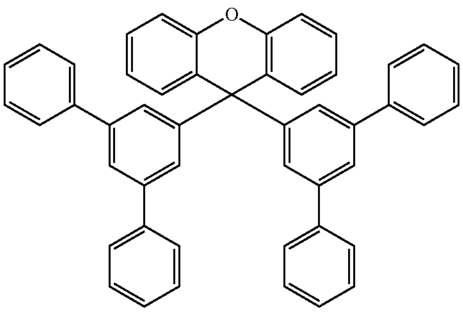

-continued
(178)
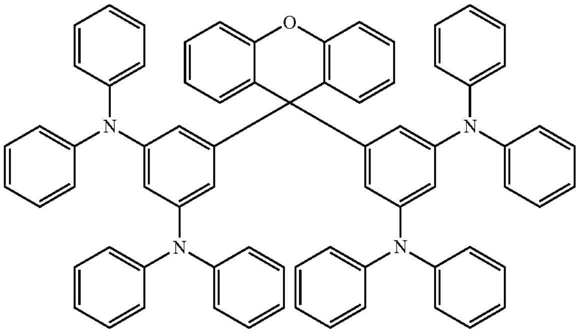
(179)
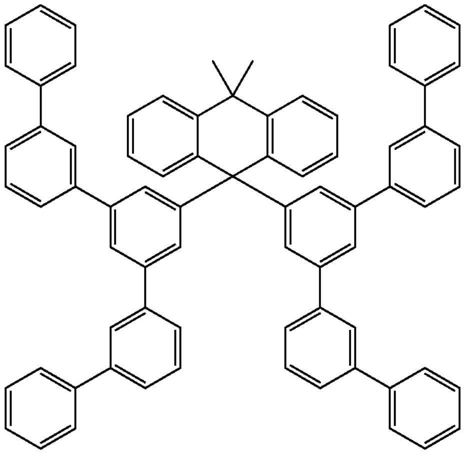
(180)
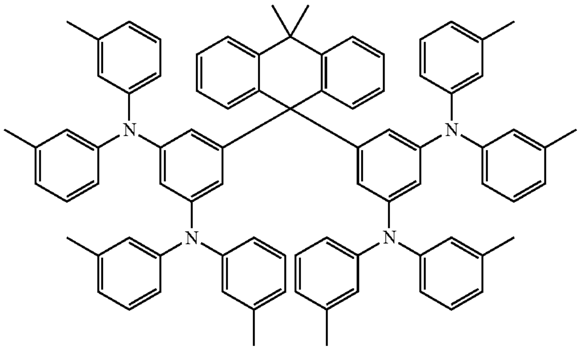
(181)
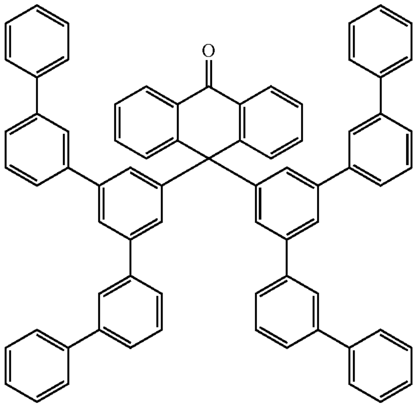
(182)
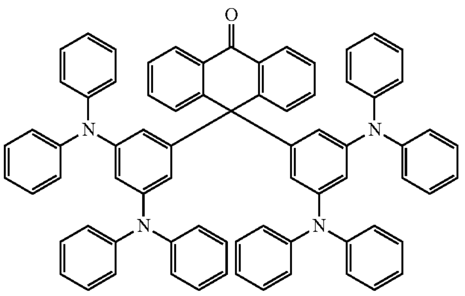
(183)
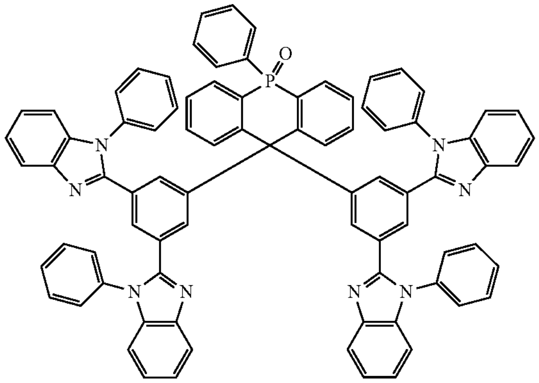

-continued
(184)
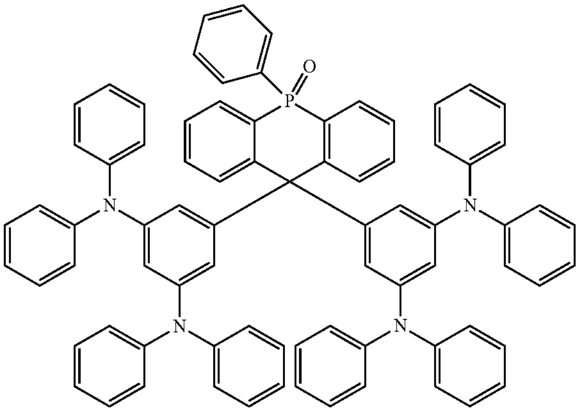
(185)
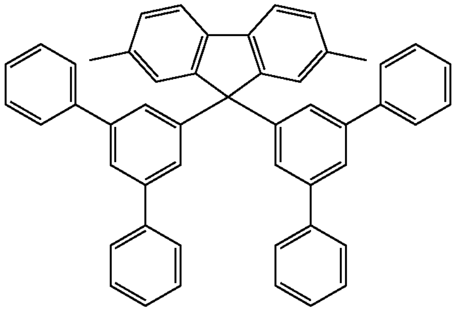
(186)
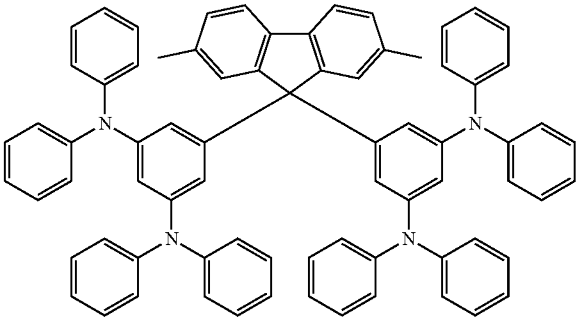
(187)
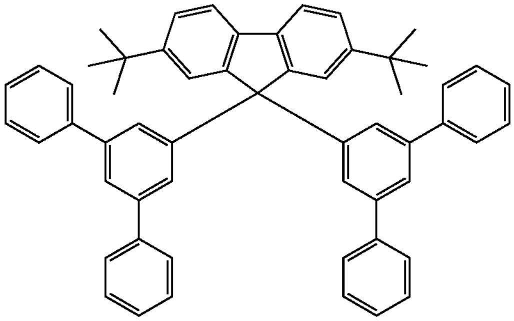
(188)
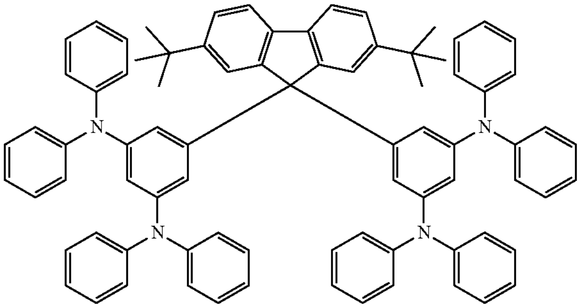
(189)
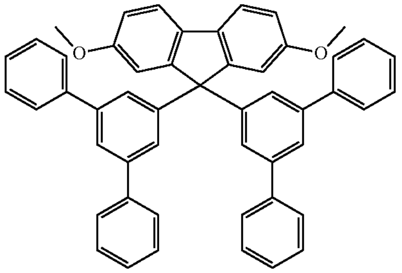
(190)
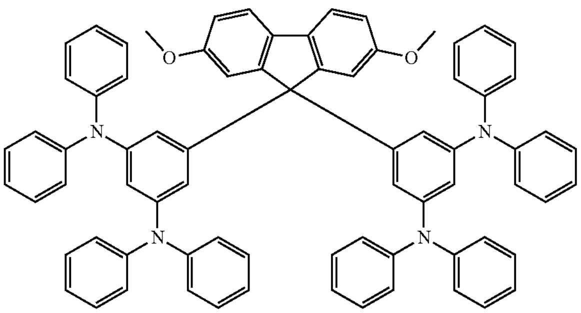
(191)
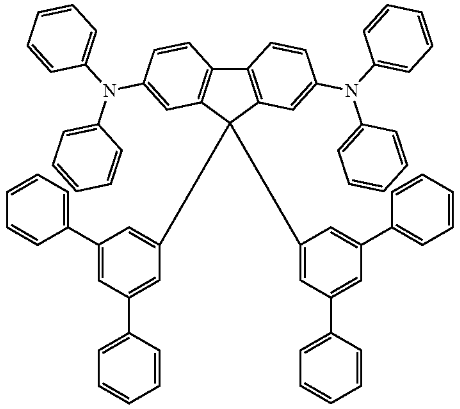

-continued
(192)
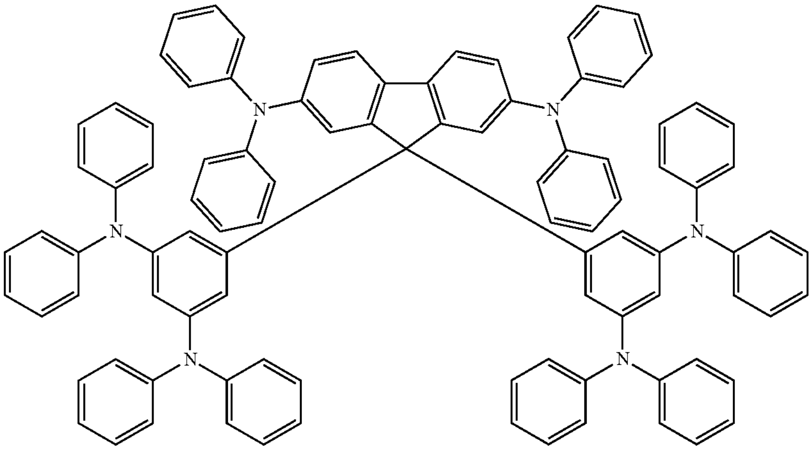
(193)
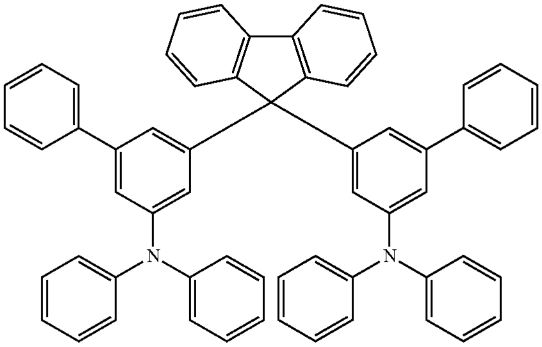
(194)
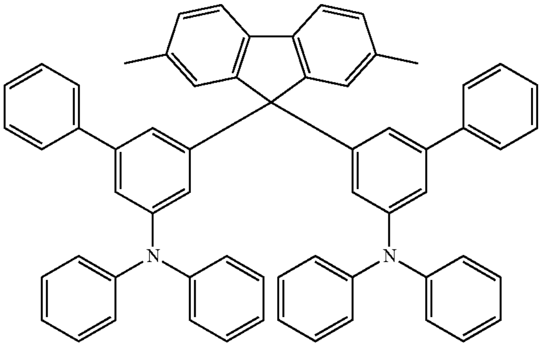
(195)
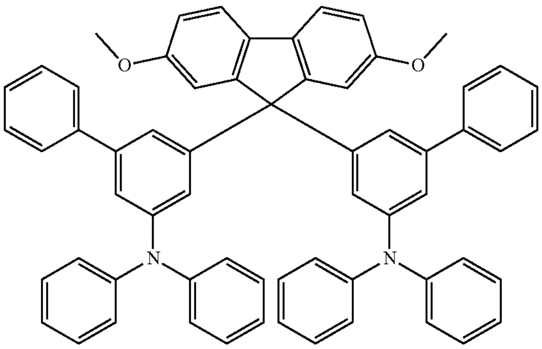
(195)
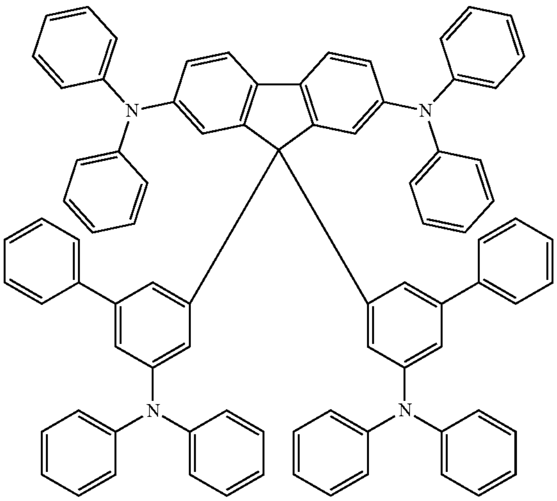

-continued
(197)
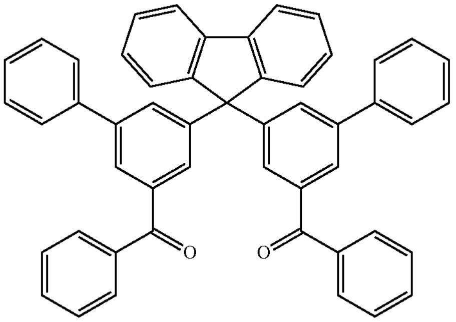
(198)
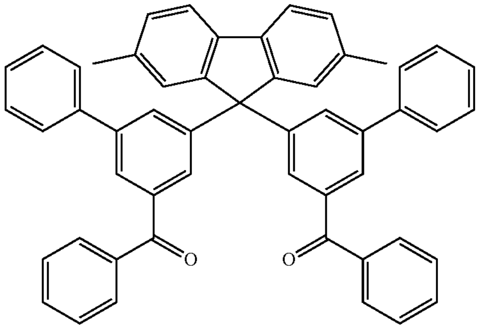
(199)
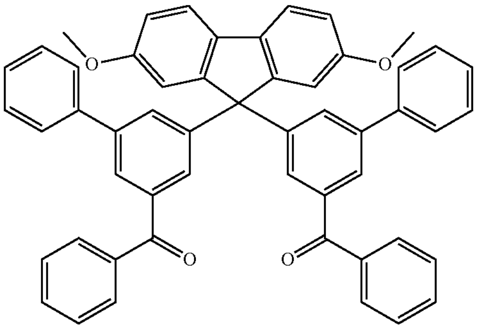
(200)
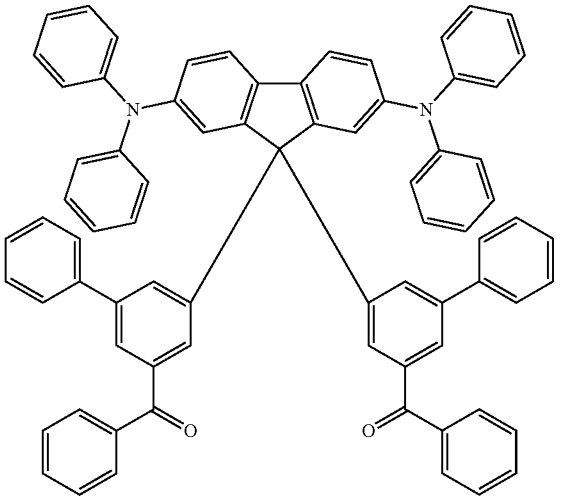
(201)
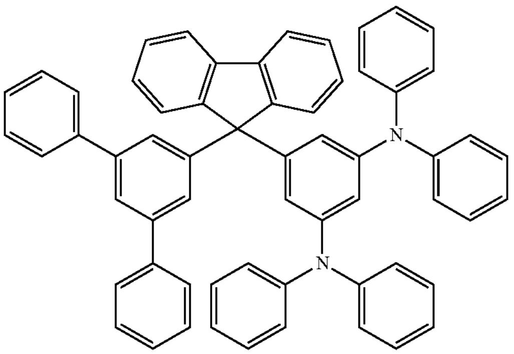
(202)
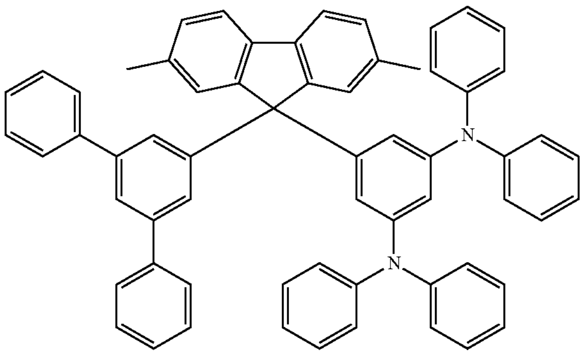

-continued
(203)
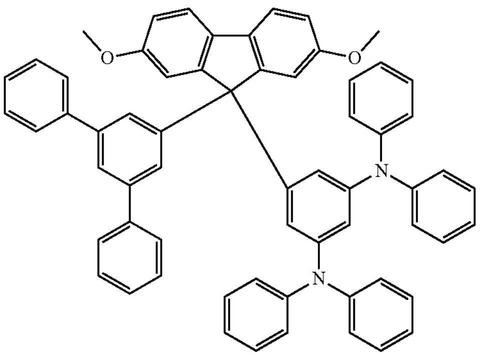
(204)
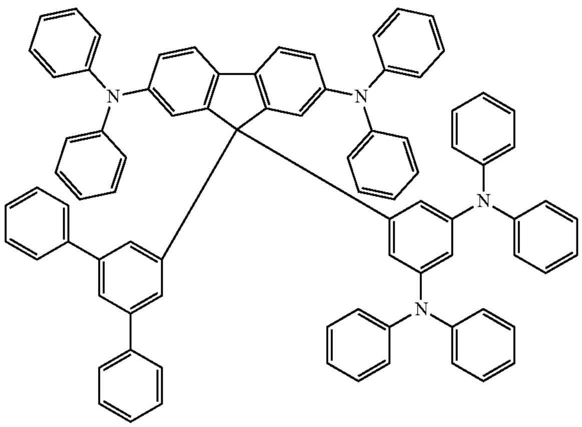
(205)
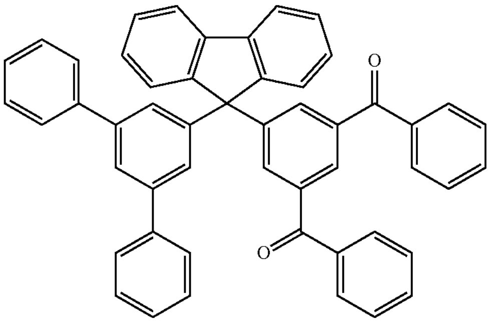
(206)
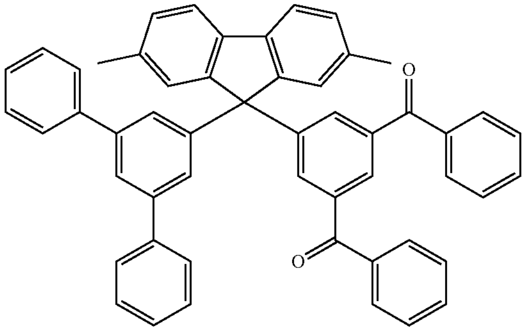
(207)
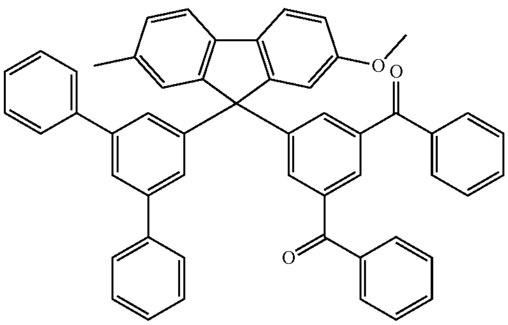
(208)
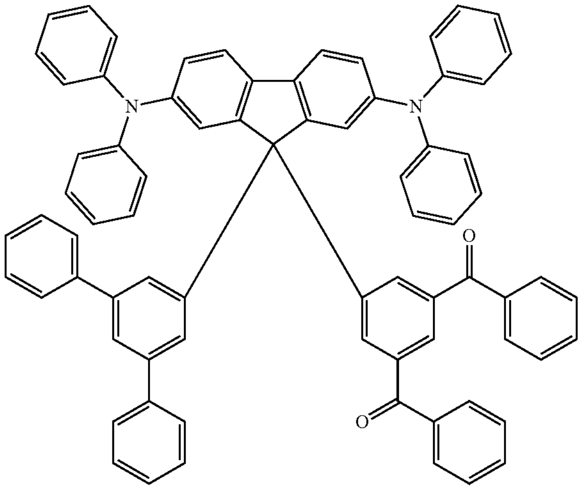

-continued
(209)
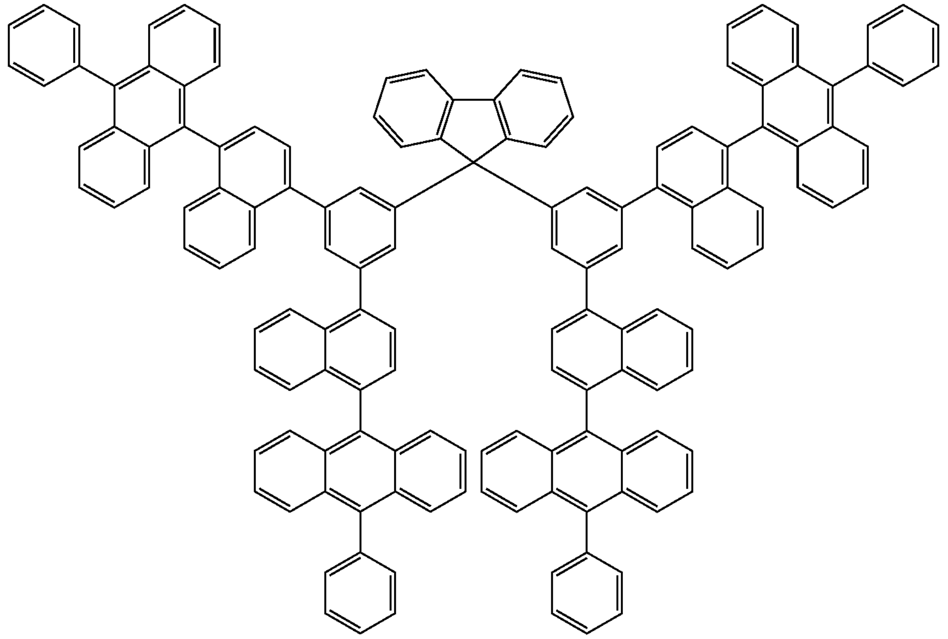
(210)
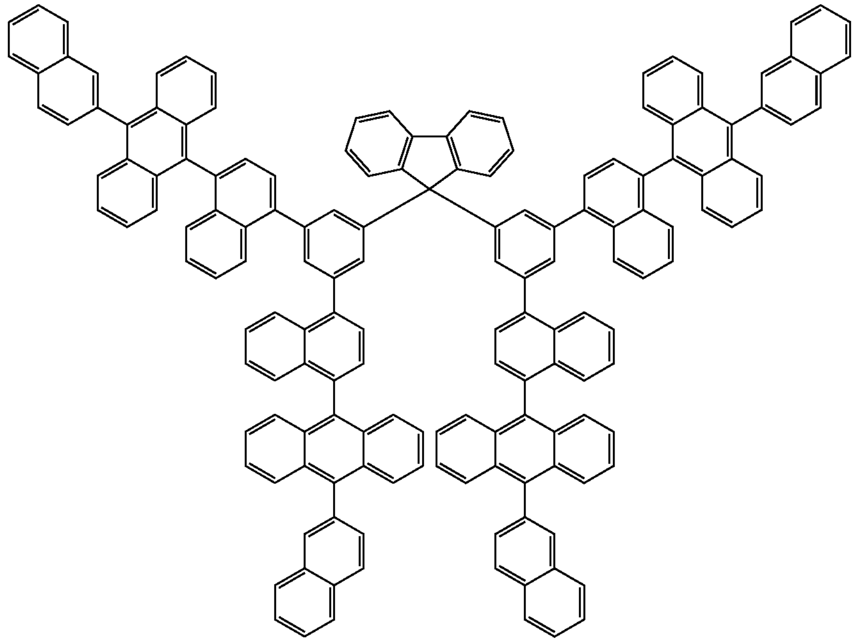

-continued
(211)
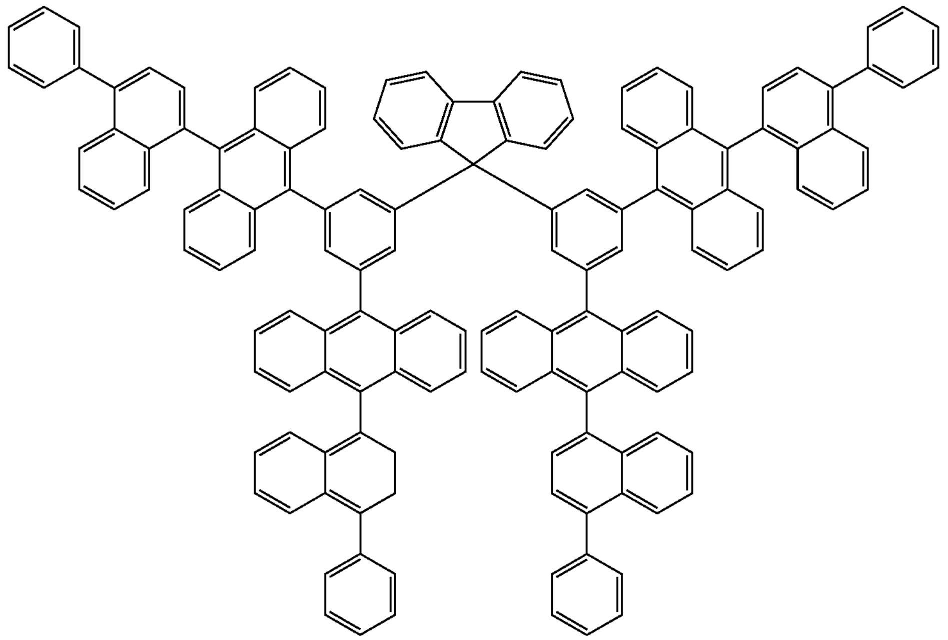
(212)
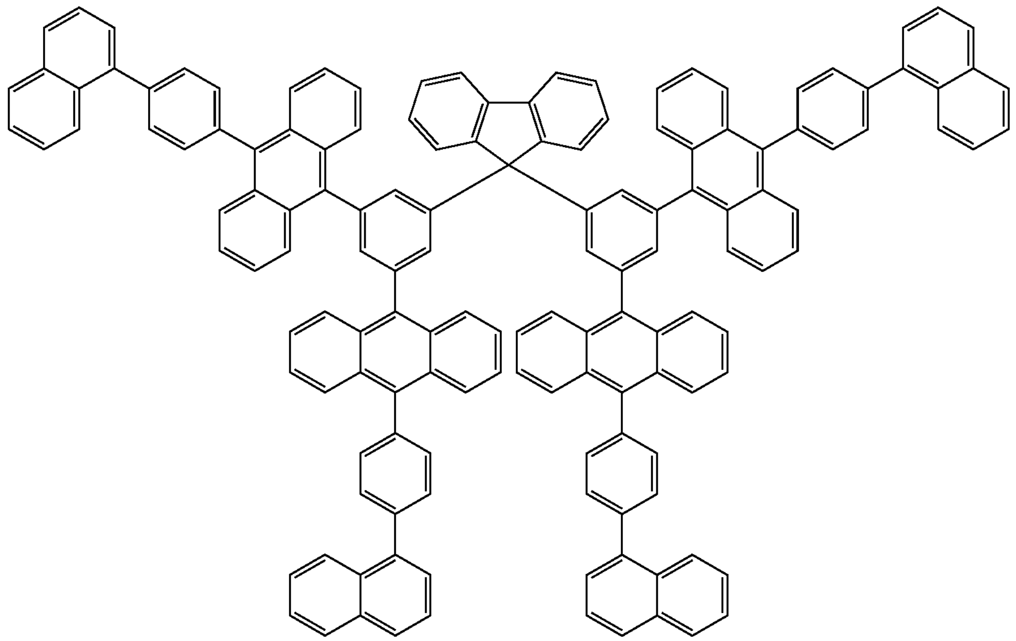

-continued
(213)
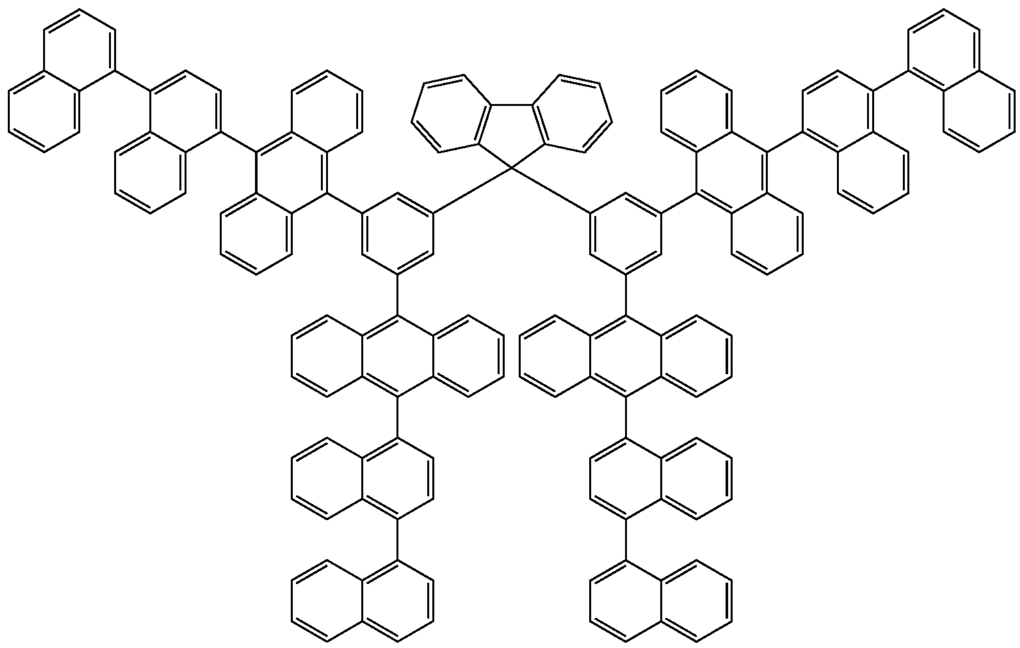
(214)
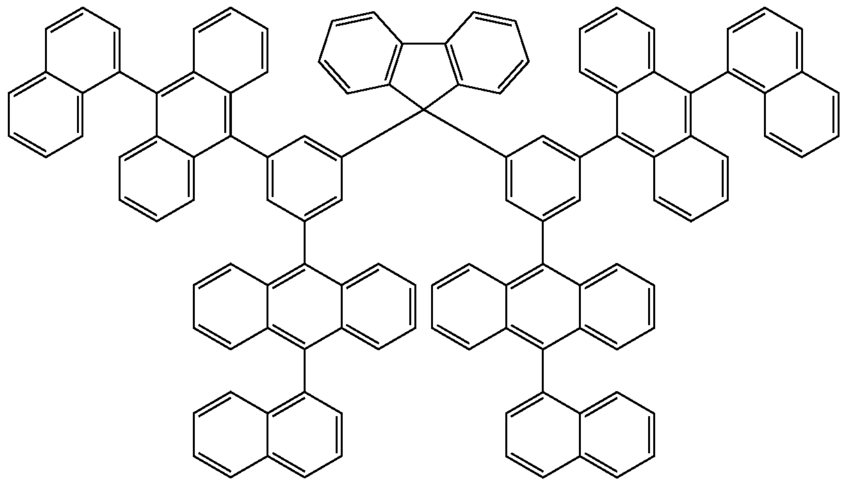

-continued
(215)
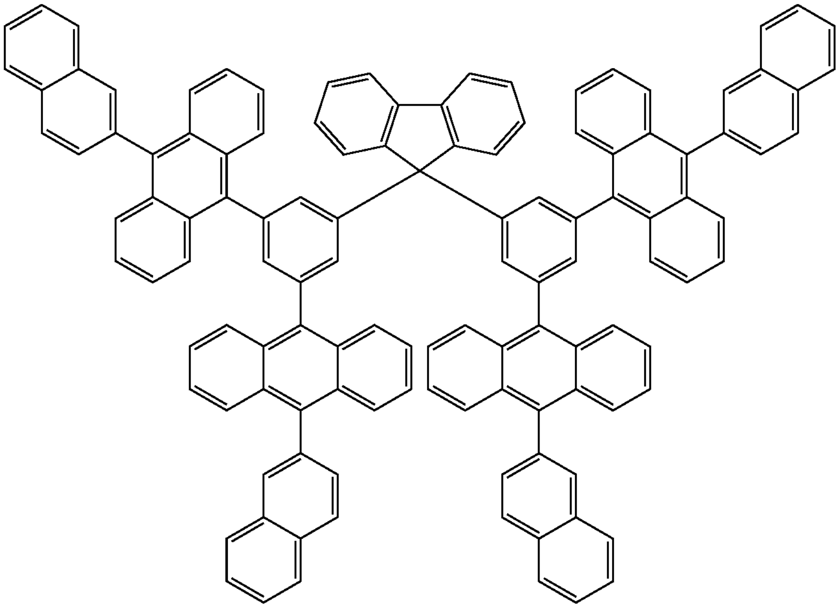
(216)
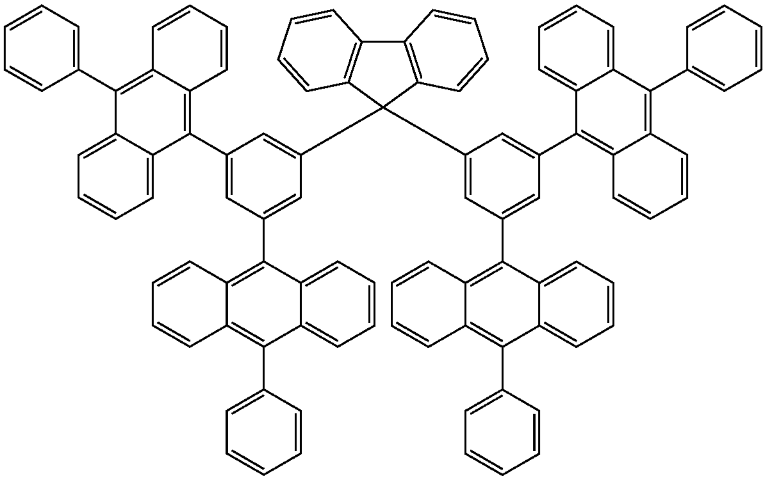

-continued
(217)
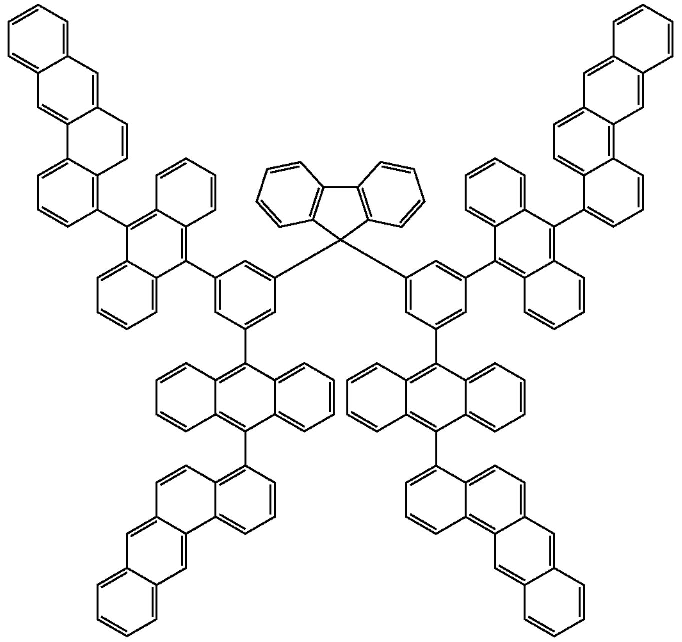
(218)
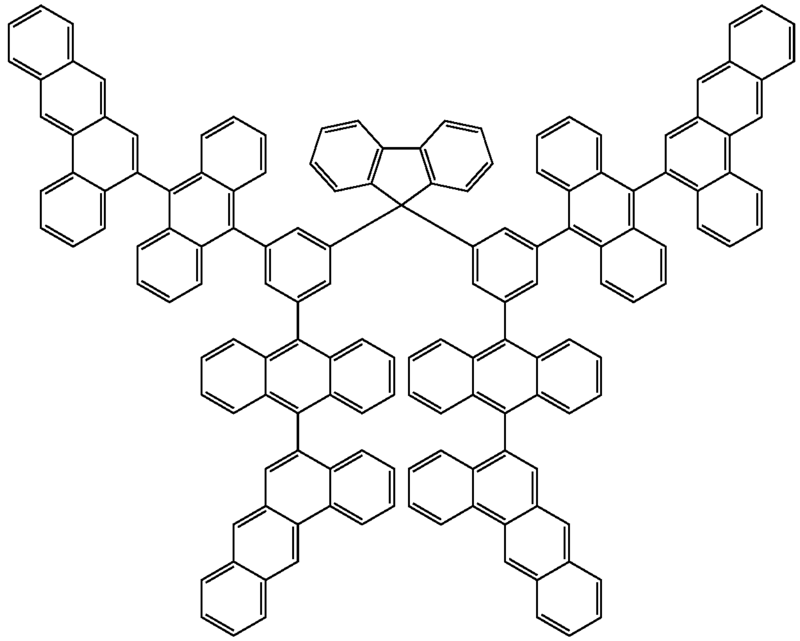

-continued
(219)
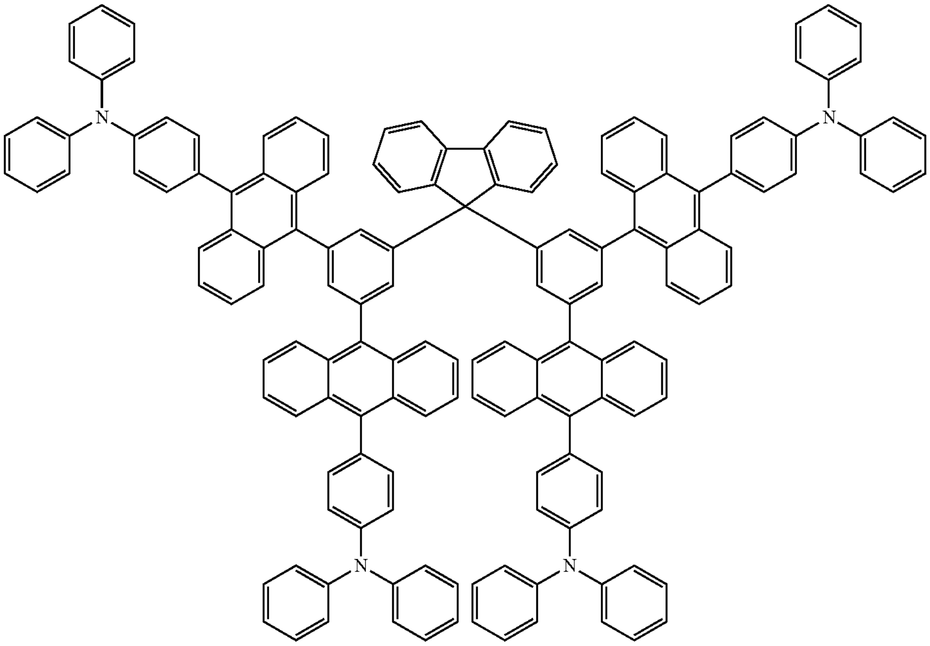
(220)
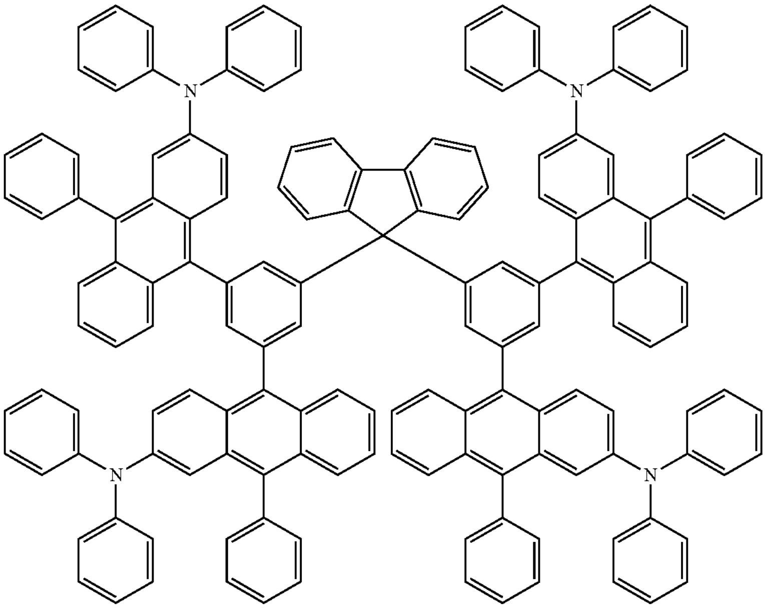

-continued
(221)
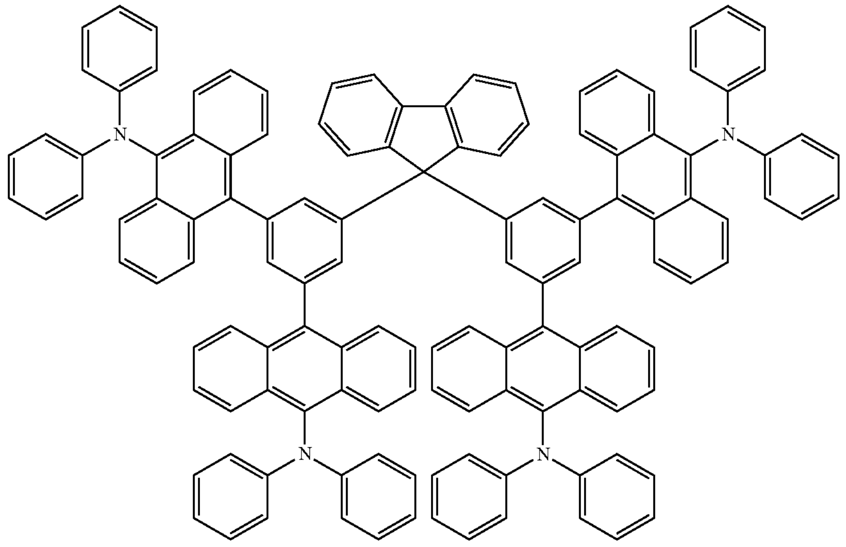
(222)
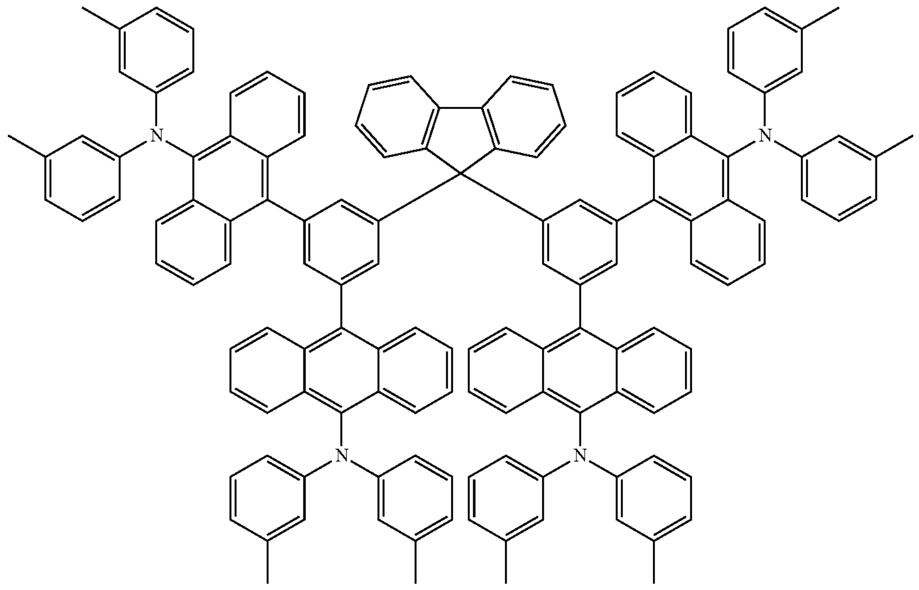

-continued
(223)
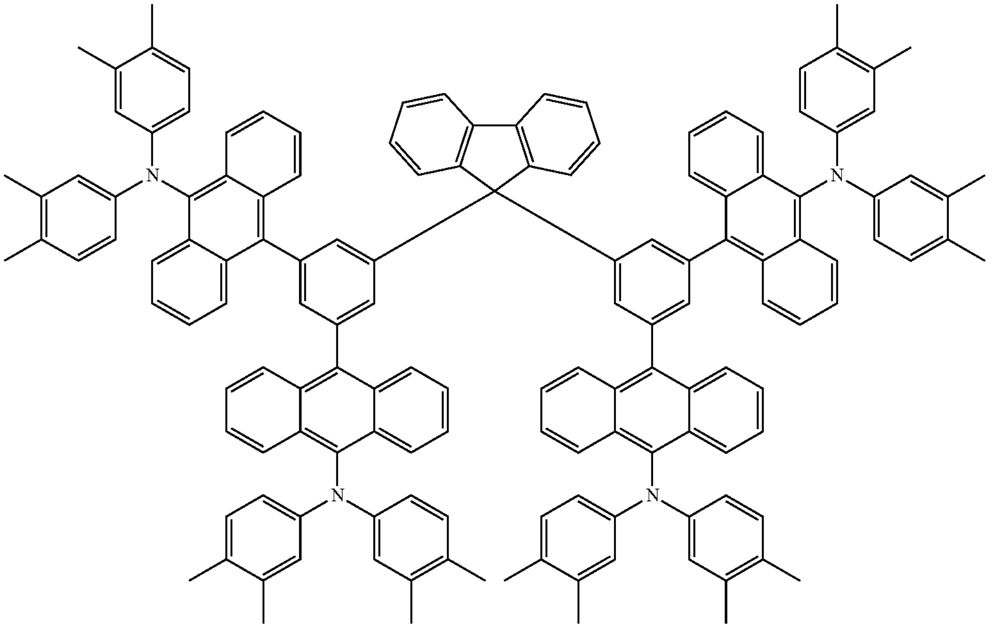
(224)
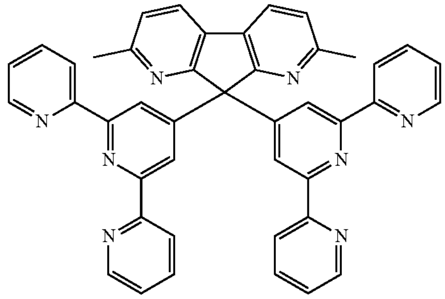
(225)
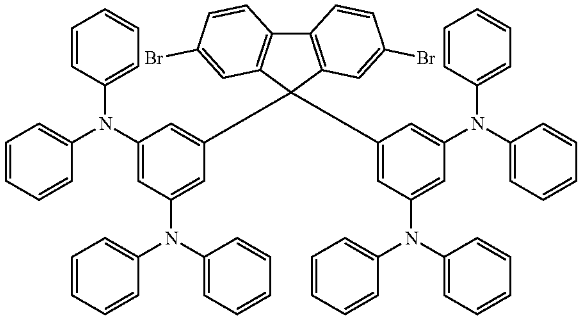
(226)
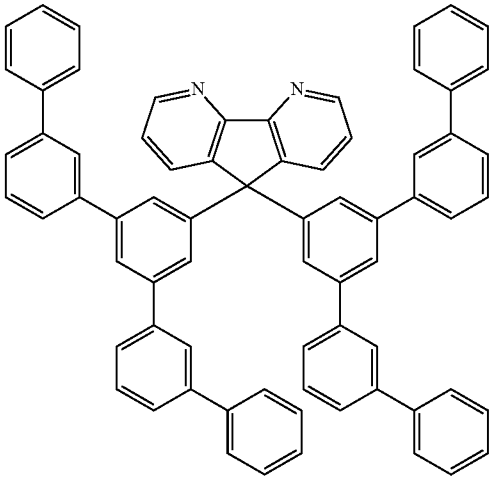
(227)
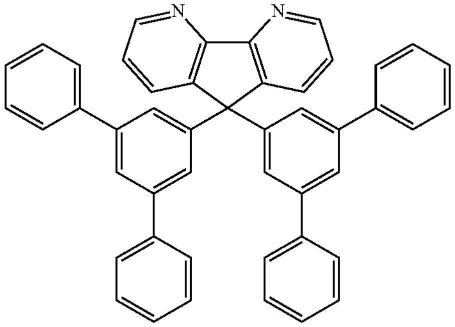

-continued
(228)
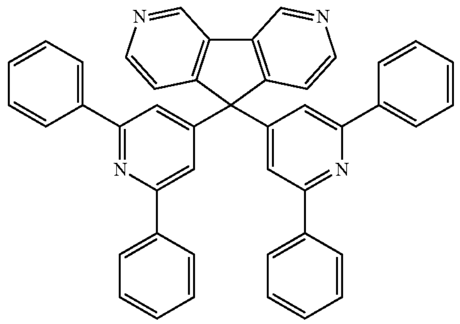
(229)
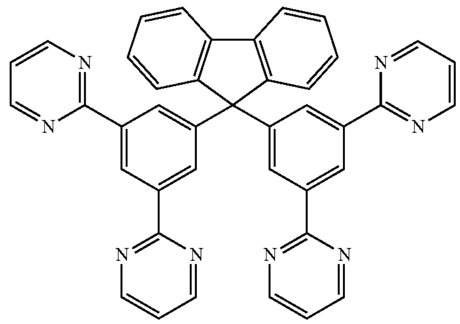
(230)
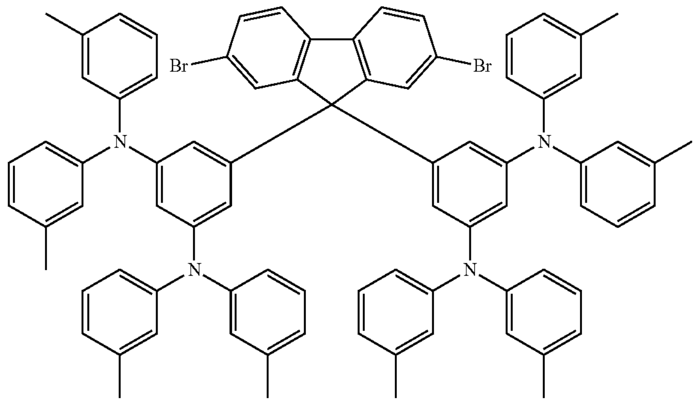
(231)
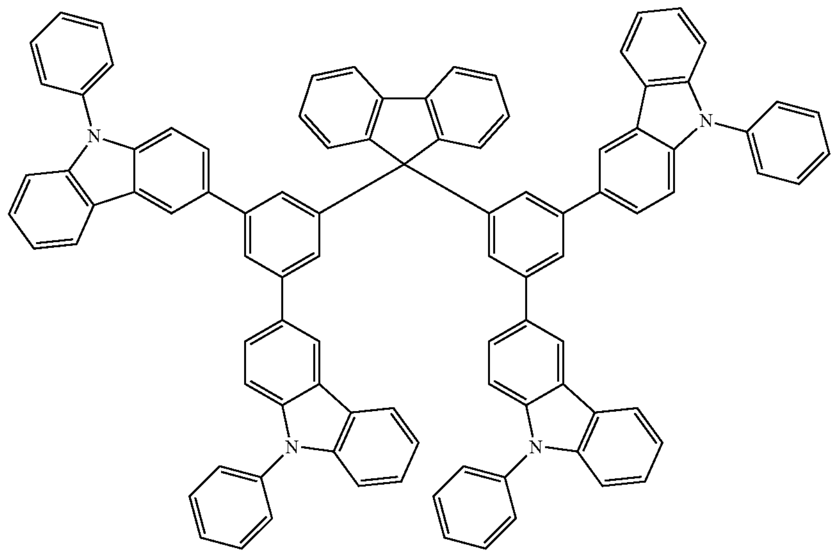
(232)
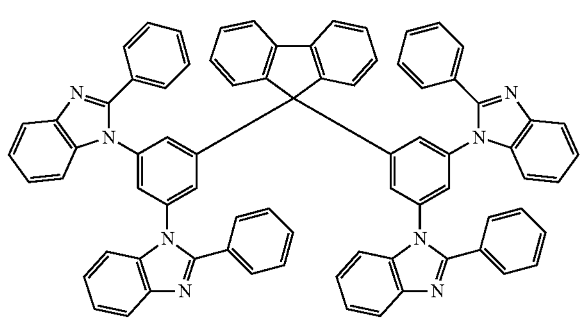
(233)
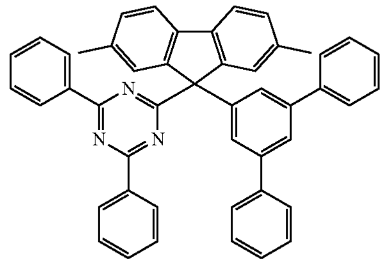

-continued
(234)
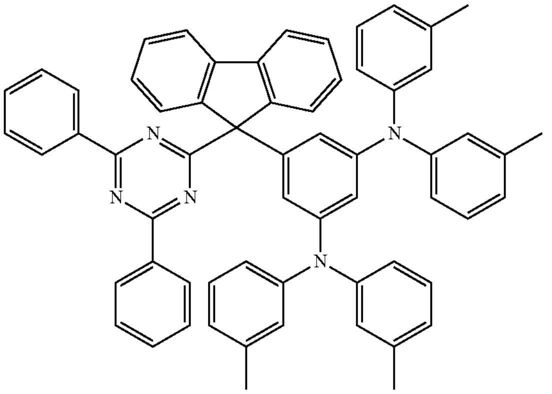
(235)
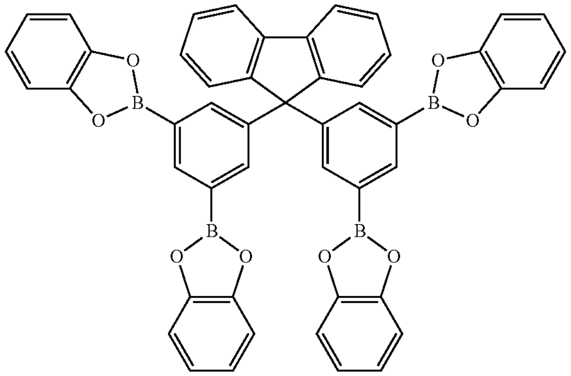
(236)
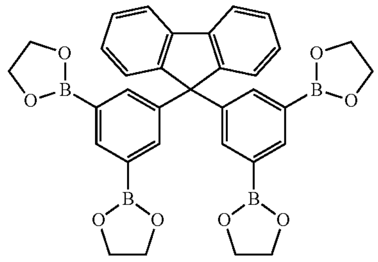
(237)
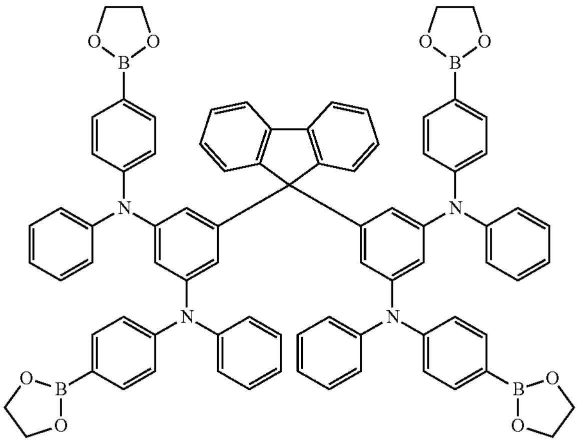
(238)
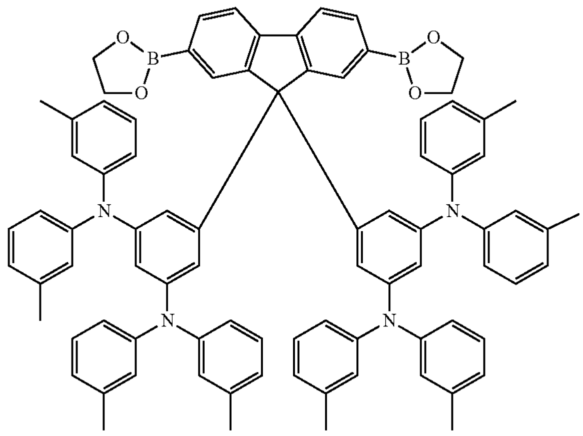
(239)
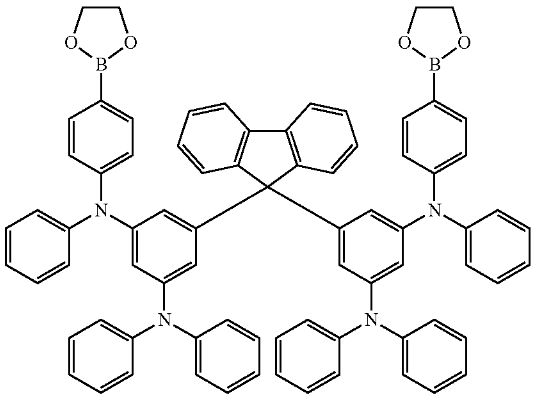

-continued
(240)
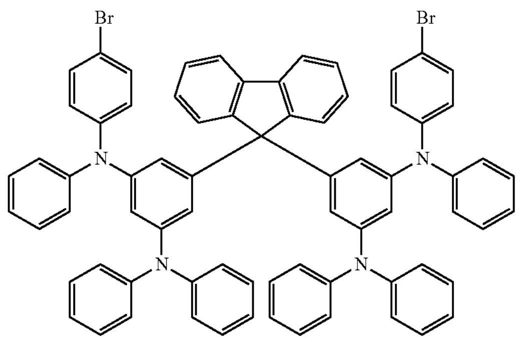
(241)
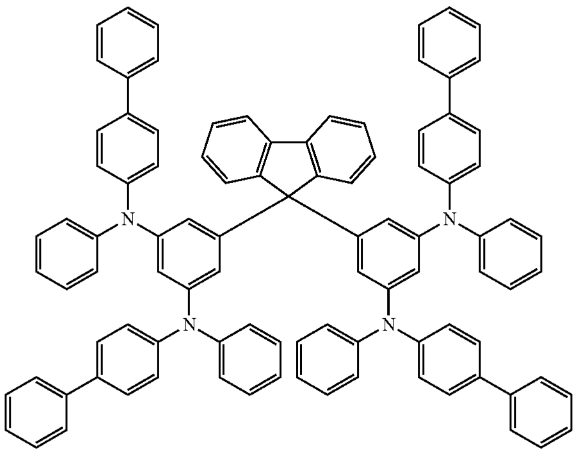
(242)
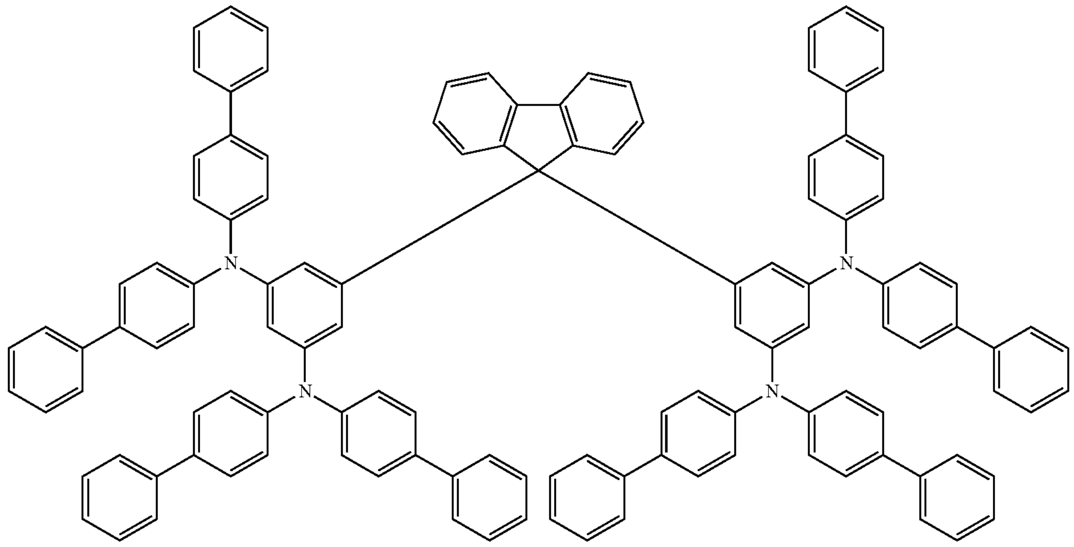
(243)
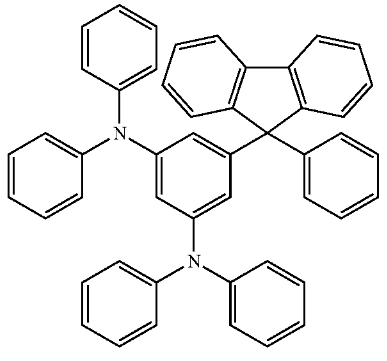
(244)
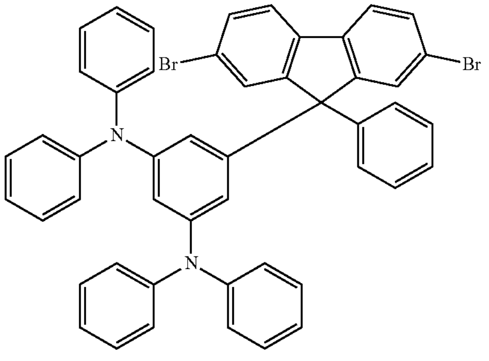

-continued
(245)
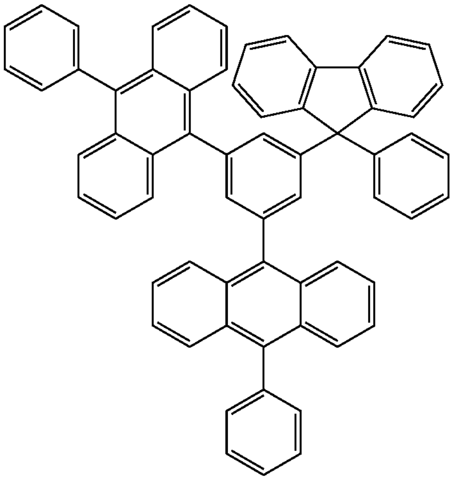
(246)
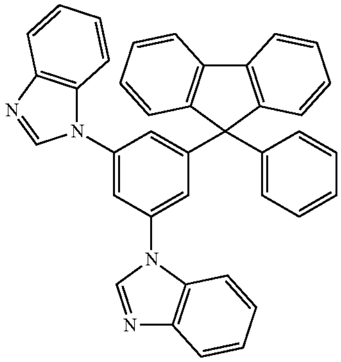
(247)
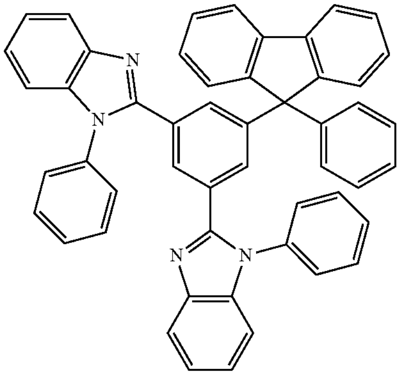
(248)
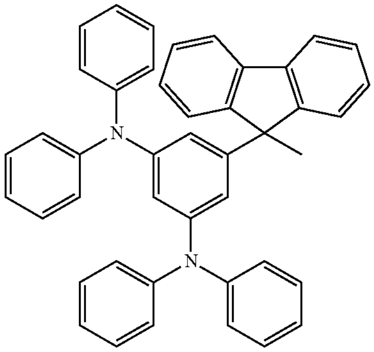
(249)
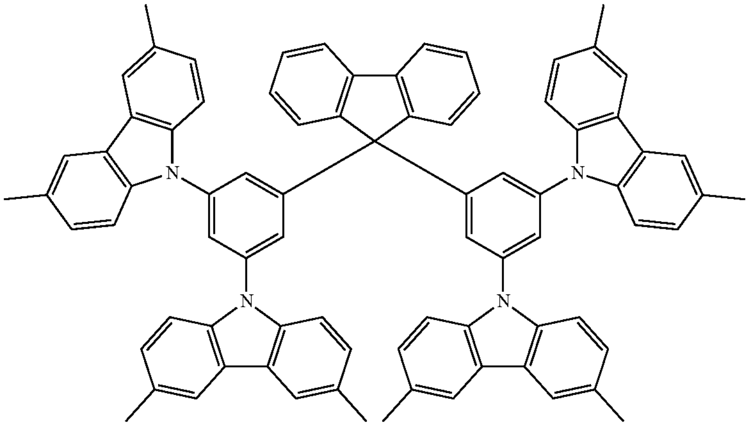

-continued
(250)
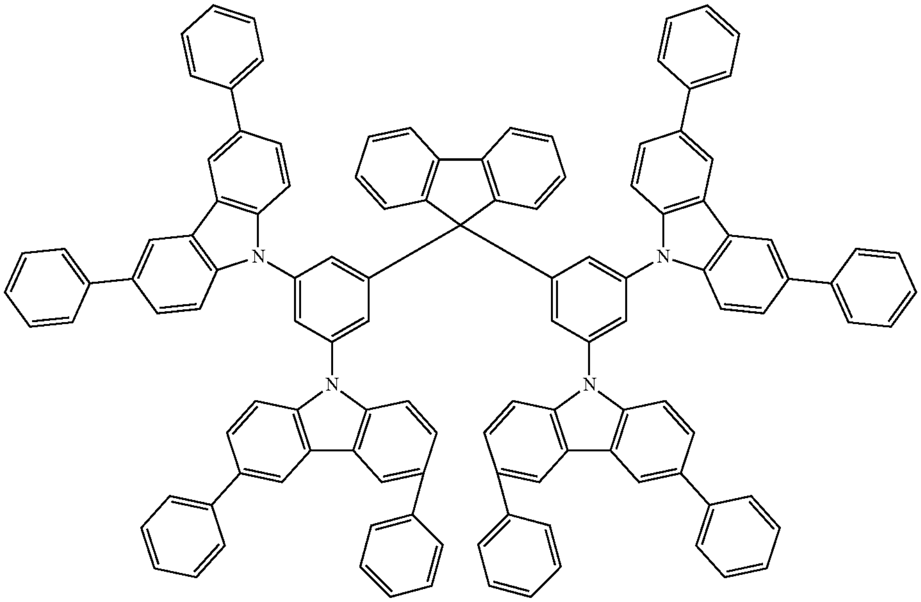
(251)
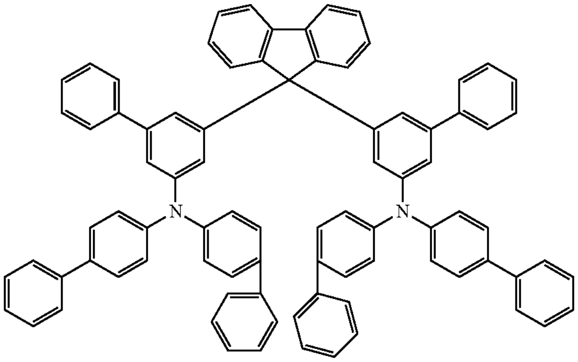
(252)
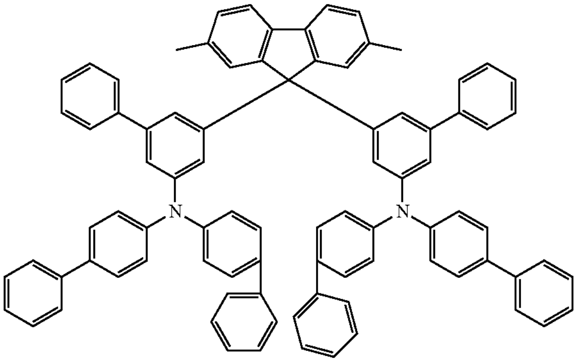
(253)
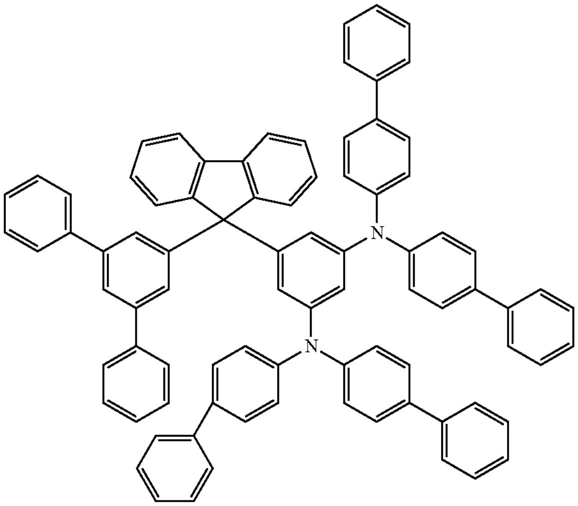
(254)
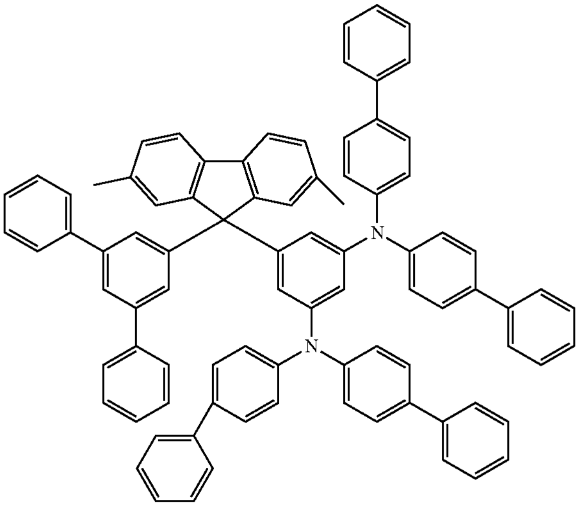

-continued
(255)
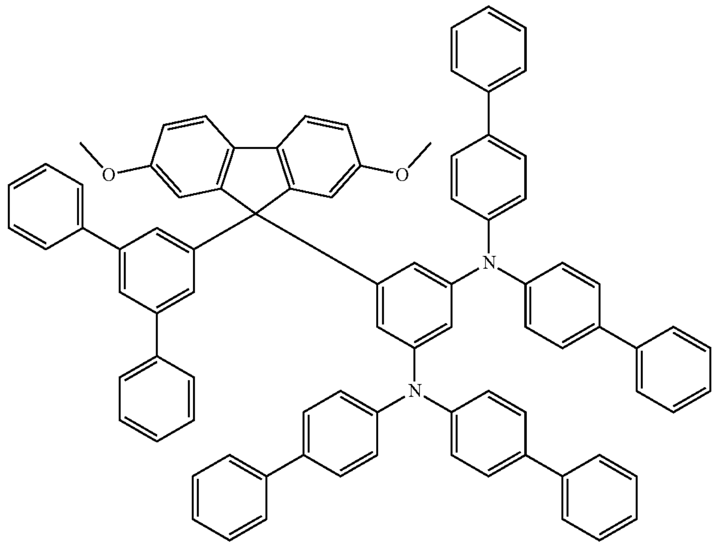
(256)
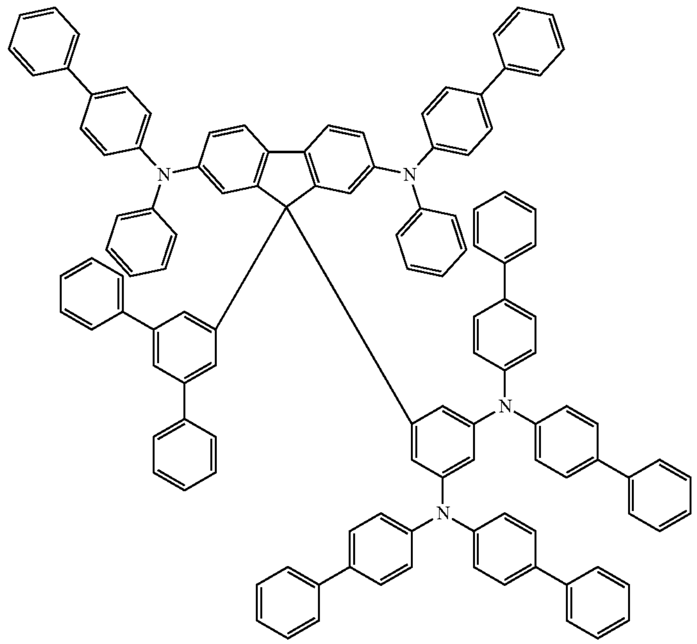

-continued
(257)
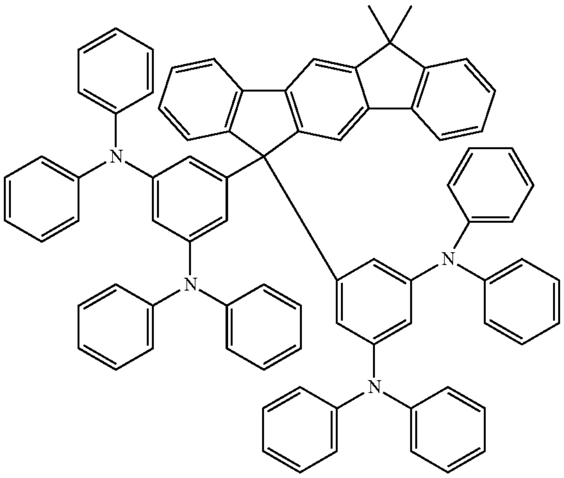
(258)
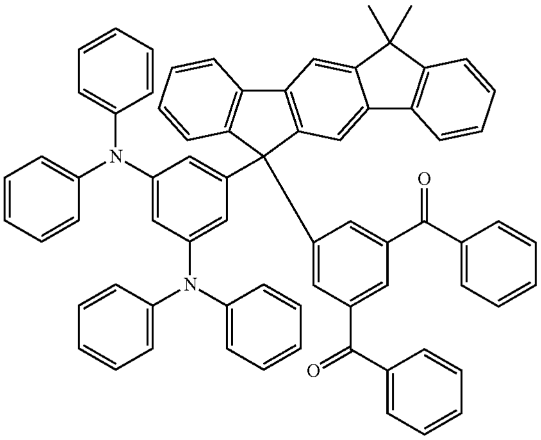
(259)
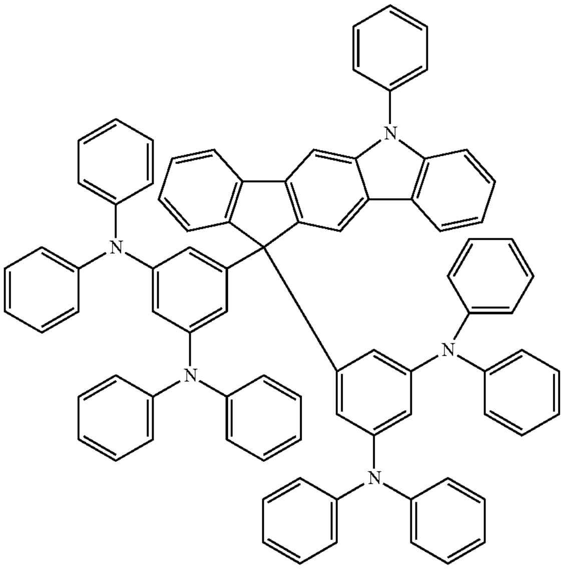
(260)
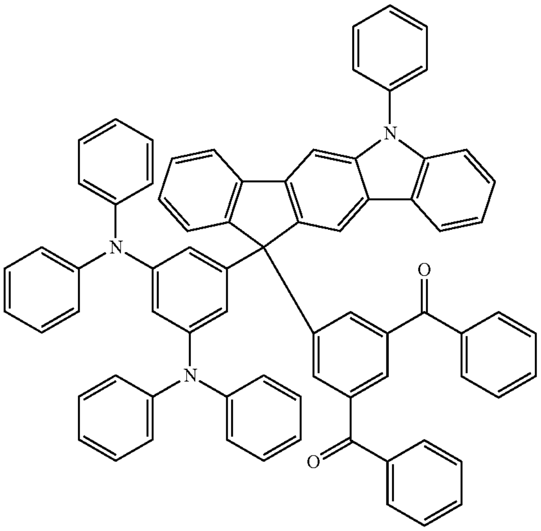
(261)
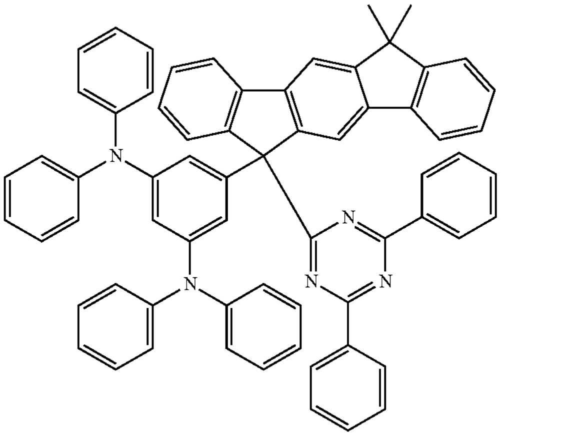
(262)
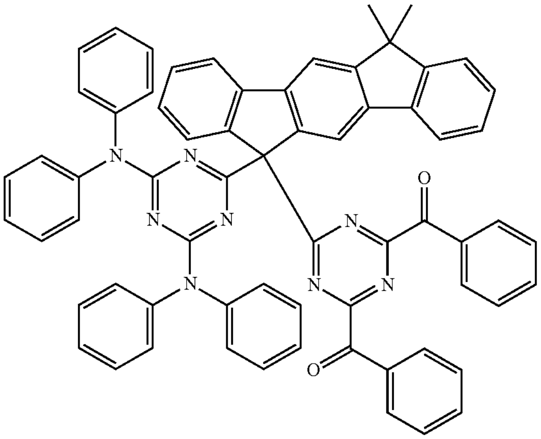

-continued
(263)
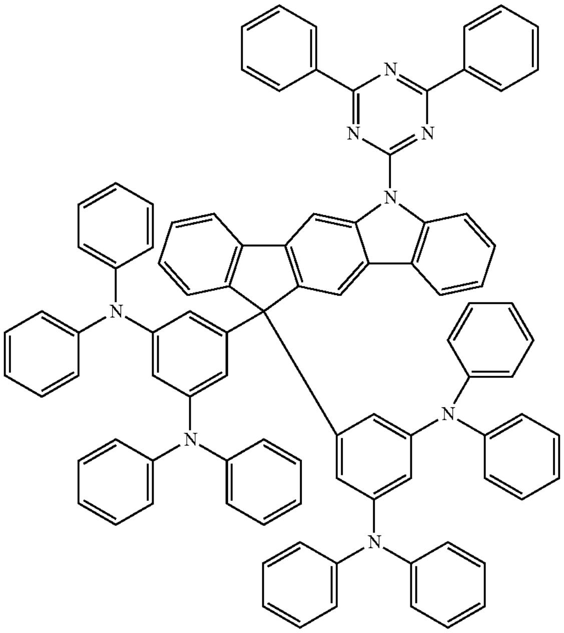
(264)
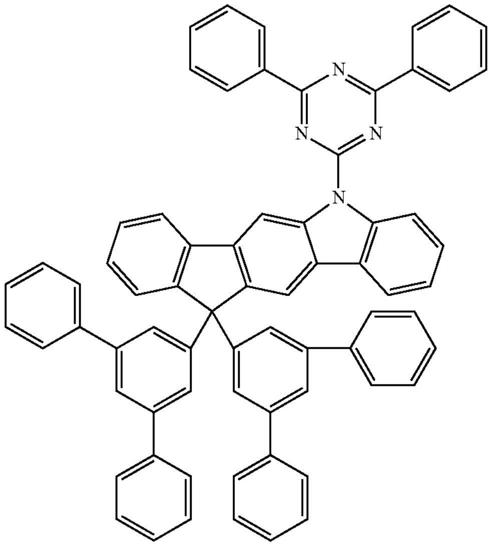
(265)
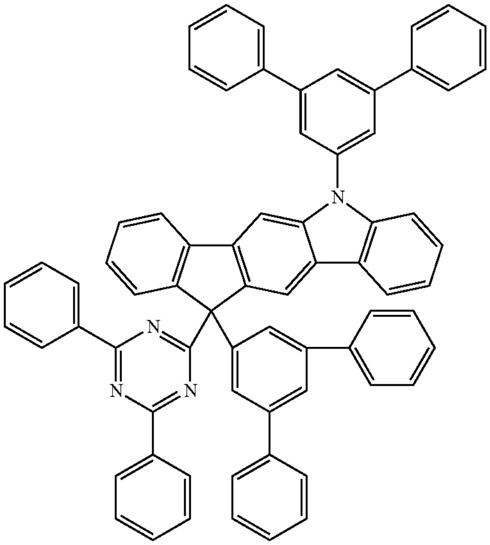
(266)
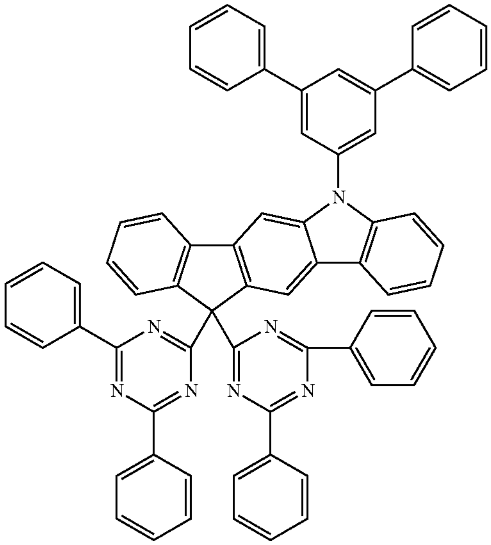

-continued
(267)
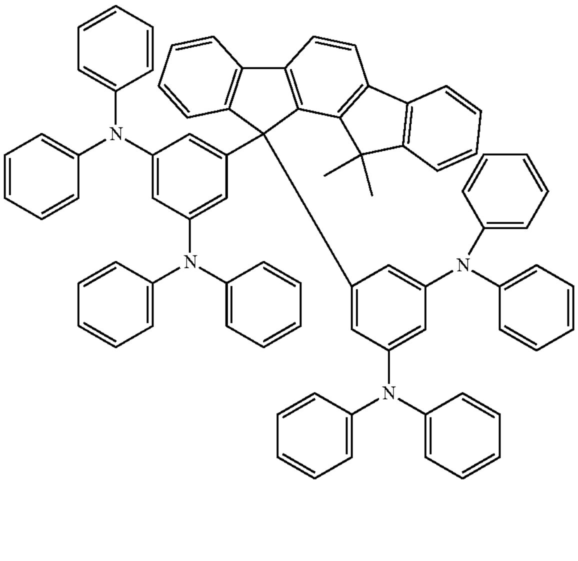
(268)
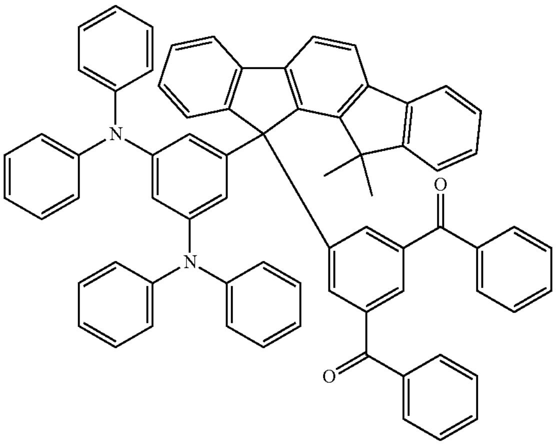
(269)
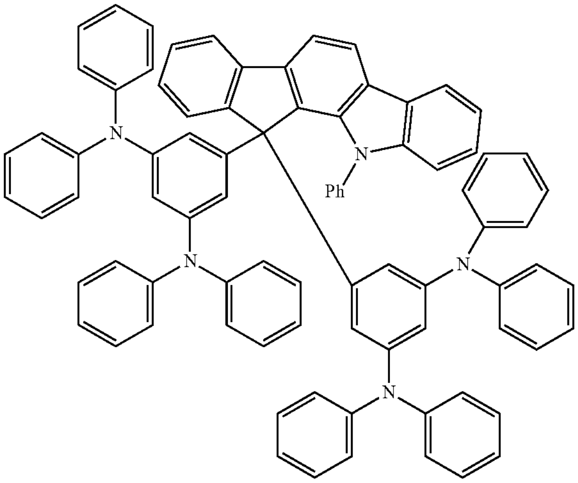
(270)
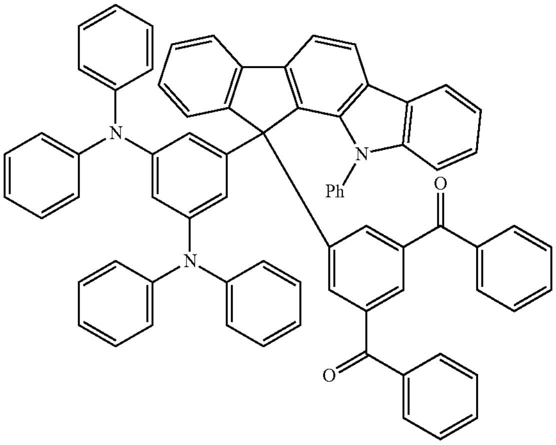
(271)
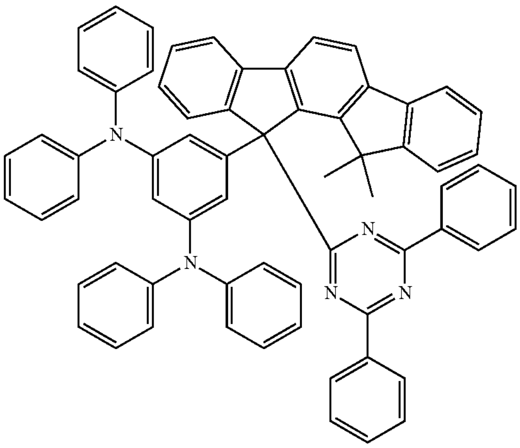
(272)
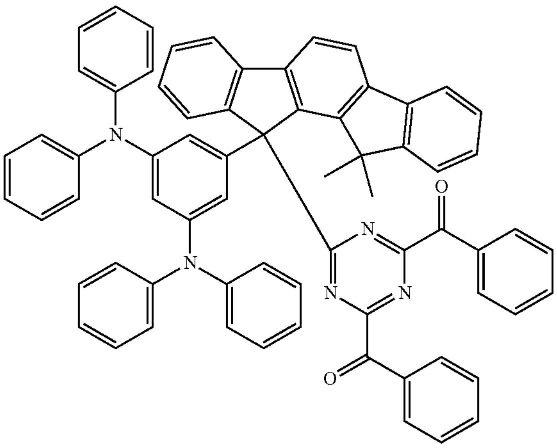

-continued (273)

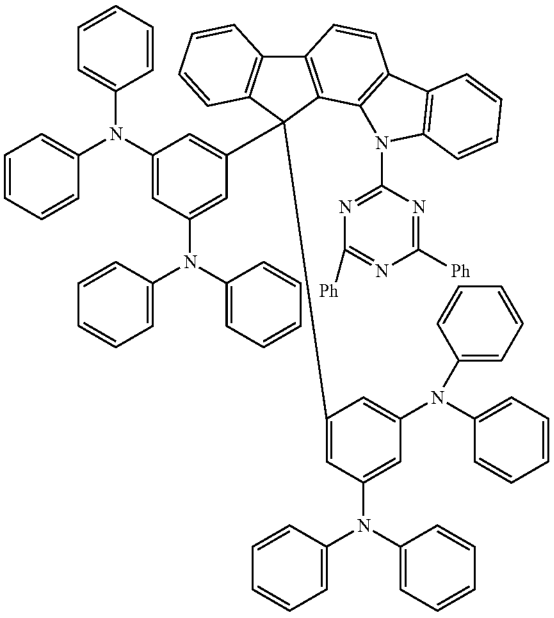

(274)

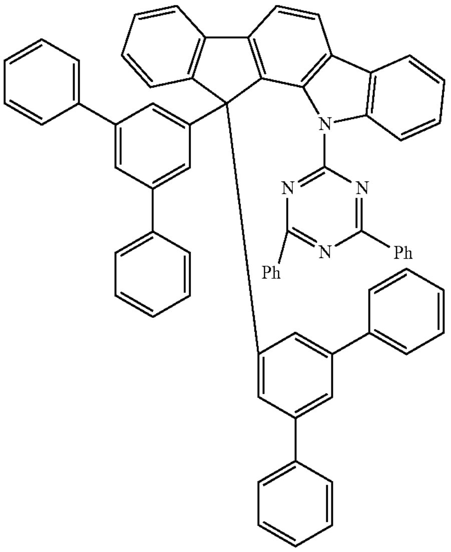

(275)

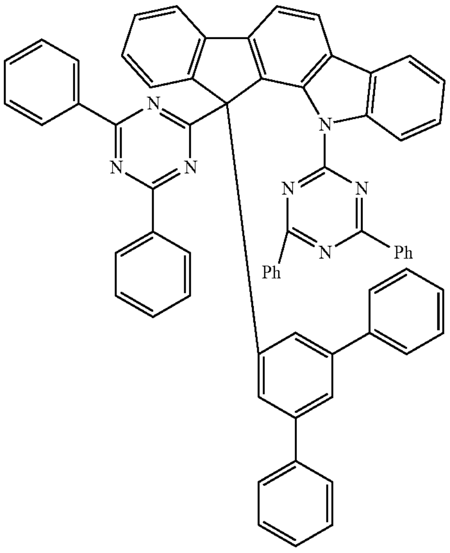

(276)

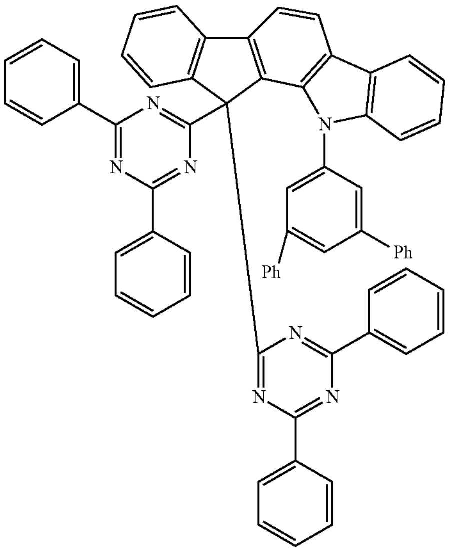

The compounds of the formula (1) according to the invention can be prepared by synthetic steps known in general terms to the person skilled in the art. The starting compound used for symmetrically substituted compounds according to the invention can be, for example, 3,3',5,5'-tetrabromobenzophenone (*Eur. J. Org. Chem.* 2006, 2523-2529). This can be converted, for example in accordance with Scheme 1, by reaction with a substituted or unsubstituted 2-lithiobiphenyl, 2-lithiodiphenyl ether, 2-lithiodiphenyl thioether, 2-(2-lithiophenyl)-2-phenyl-1,3-dioxolane or 2-lithiophenyldiphenylamine into the corresponding triarylmethanols, which are then cyclised under acidic conditions, for example in the presence of acetic acid and a mineral acid, such as hydrogen bromide. The organolithium compounds required for this reaction can be prepared by transmetallation of the corresponding aryl bromides (2-bromobiphenyl, 2-bromodiphenyl ether, 2-bromodiphenyl thioether, 2-(2-bromophenyl)-2-phenyl-1,3-dioxolane, 2-bromophenyldiphenylamine, etc.) using alkyllithium compounds, such as n-butyllithium. It is of course possible to employ the corresponding Grignard compounds analogously.

Scheme 1

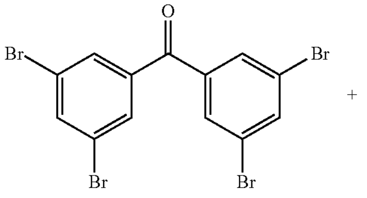

-continued

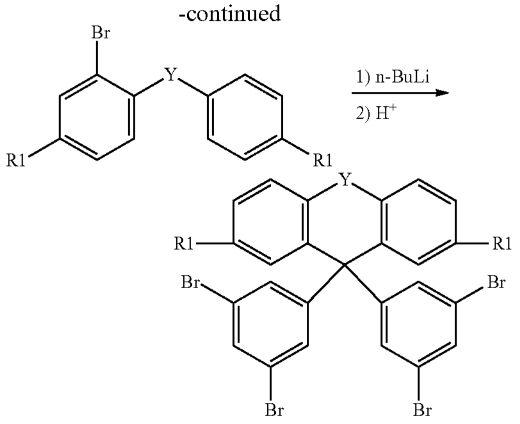

The tetrabromides produced in this way can be converted further by methods known to the person skilled in the art. Palladium-catalysed reaction with boronic acids (Suzuki coupling) or palladium-catalysed reaction with organozinc compounds (Negishi coupling) leads to aromatic or heteroaromatic compounds according to the invention (Scheme 2).

Scheme 2

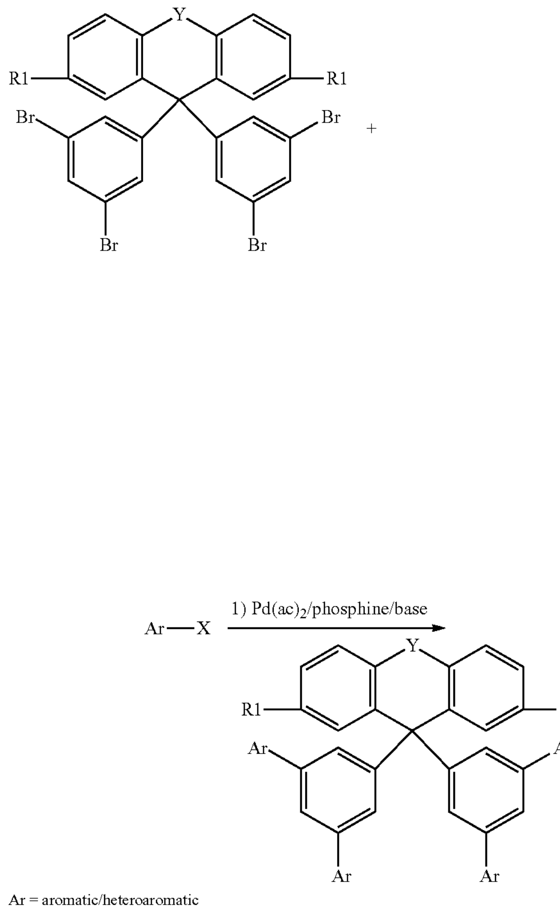

Ar = aromatic/heteroaromatic hydrocarbon
X = $B(OH)_2$, ZnBr, MgBr, etc.

Palladium-catalysed reaction with amines (Hartwig-Buchwald coupling) leads to aromatic or heteroaromatic amines according to the invention (Scheme 3).

Scheme 3

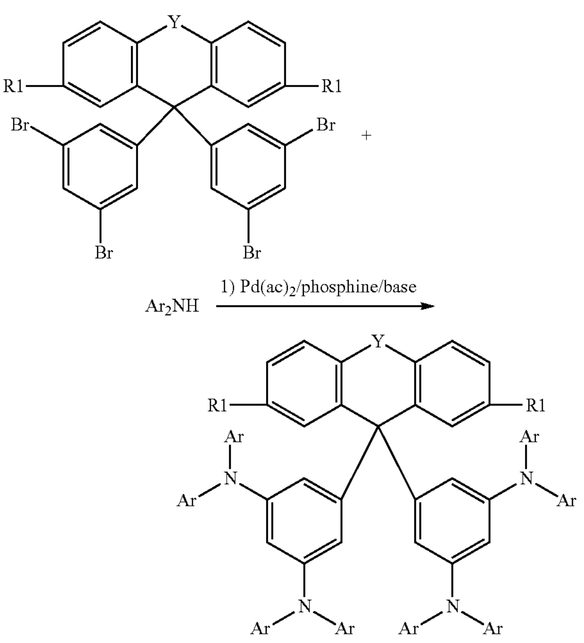

Ar = aromatic/heteroaromatic hydrocarbon

The bromine function can be converted by transmetallation using organolithium compounds or Grignard compounds into an electrophilic group, which is then coupled to a multiplicity of electrophiles, such as, for example, arylboron halides, aldehydes, ketones, nitriles, esters, halogen esters, carbon dioxide, arylphosphine halides, halosulfinic acids, haloarylsulfonic acids, etc., where the compounds obtained in this way may be final products according to the invention or alternatively intermediates, which can be reacted further. This is illustrated by way of example with reference to the example of the preparation of a ketone according to the invention, a phosphine oxide and a benzimidazole (Scheme 4).

Scheme 4

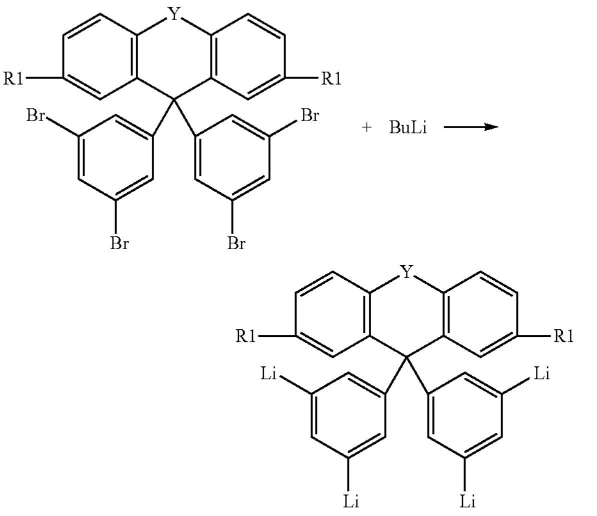

-continued

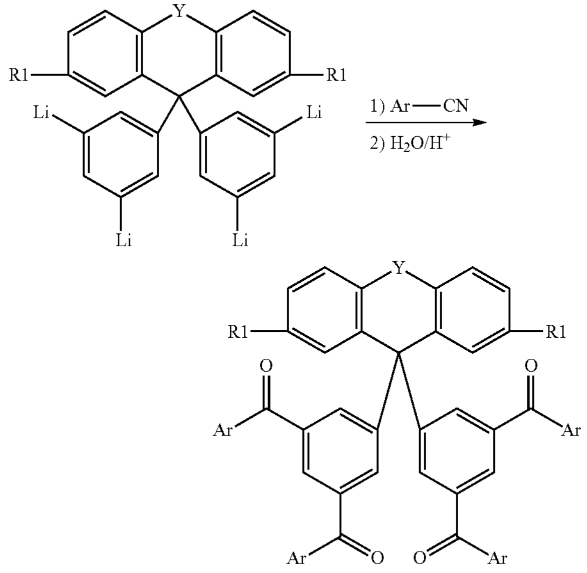

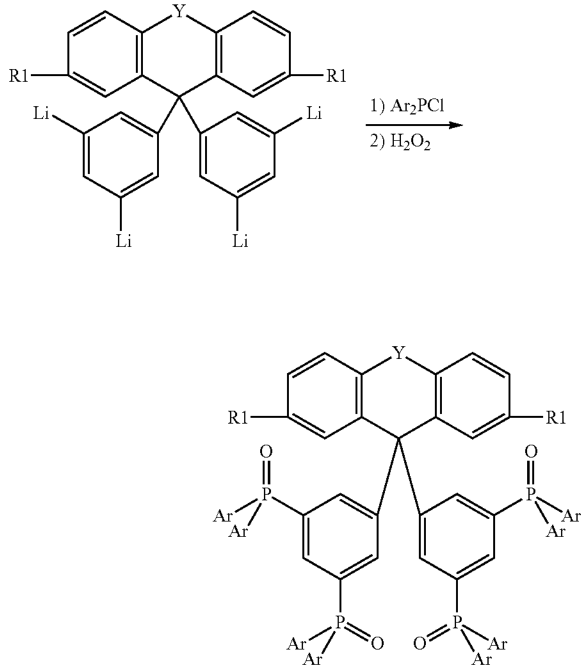

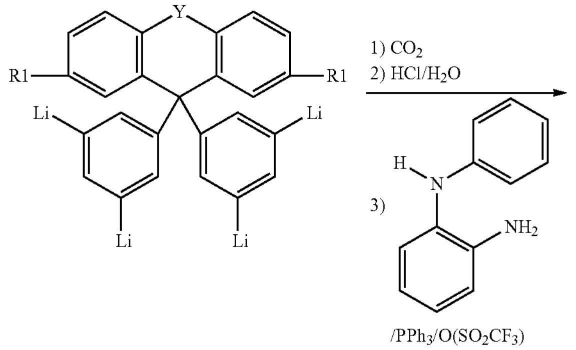

-continued

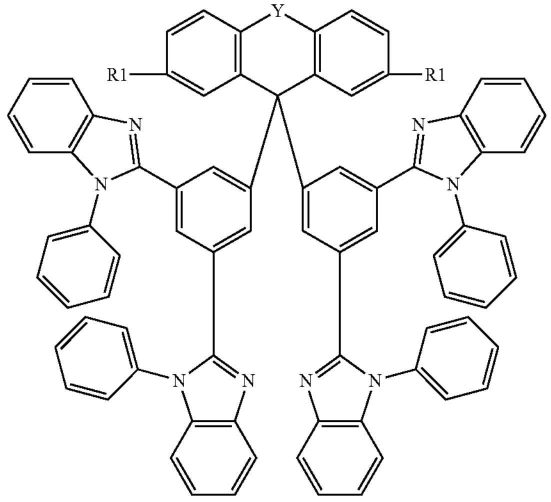

Asymmetrically substituted compounds according to the invention can be obtained by the sequence in accordance with Scheme 5 starting from fluorenone and analogous aryl ketones by addition of an aryl-metal compound, for example 1-lithio-3,5-dibromobenzene, onto the carbonyl function, conversion of the brominated aromatic compound by one of the methods mentioned above with build-up of one functionality and subsequent introduction of the other functionality via acid-catalysed Friedel-Crafts arylation on 1,3-dibromobenzene and conversion of the brominated aromatic compound by one of the methods mentioned above (see, for example, *Org. Lett.* 2001, 3(15), 2285).

Scheme 5

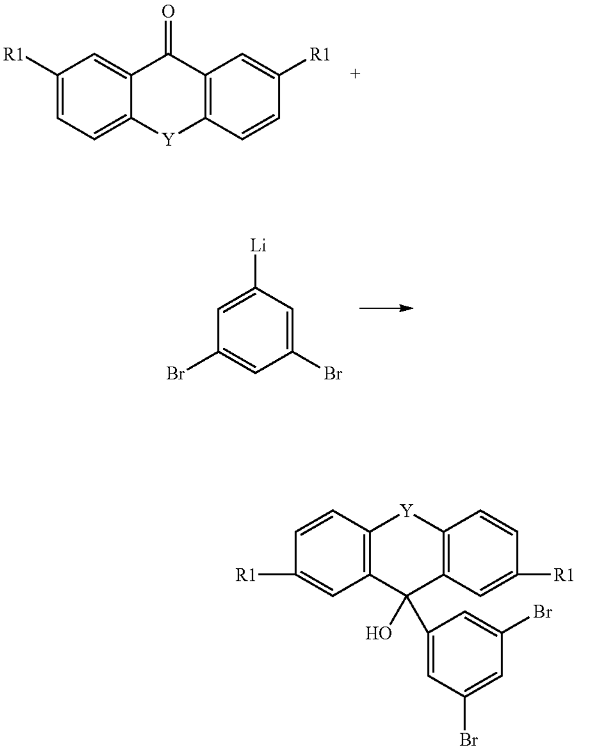

-continued

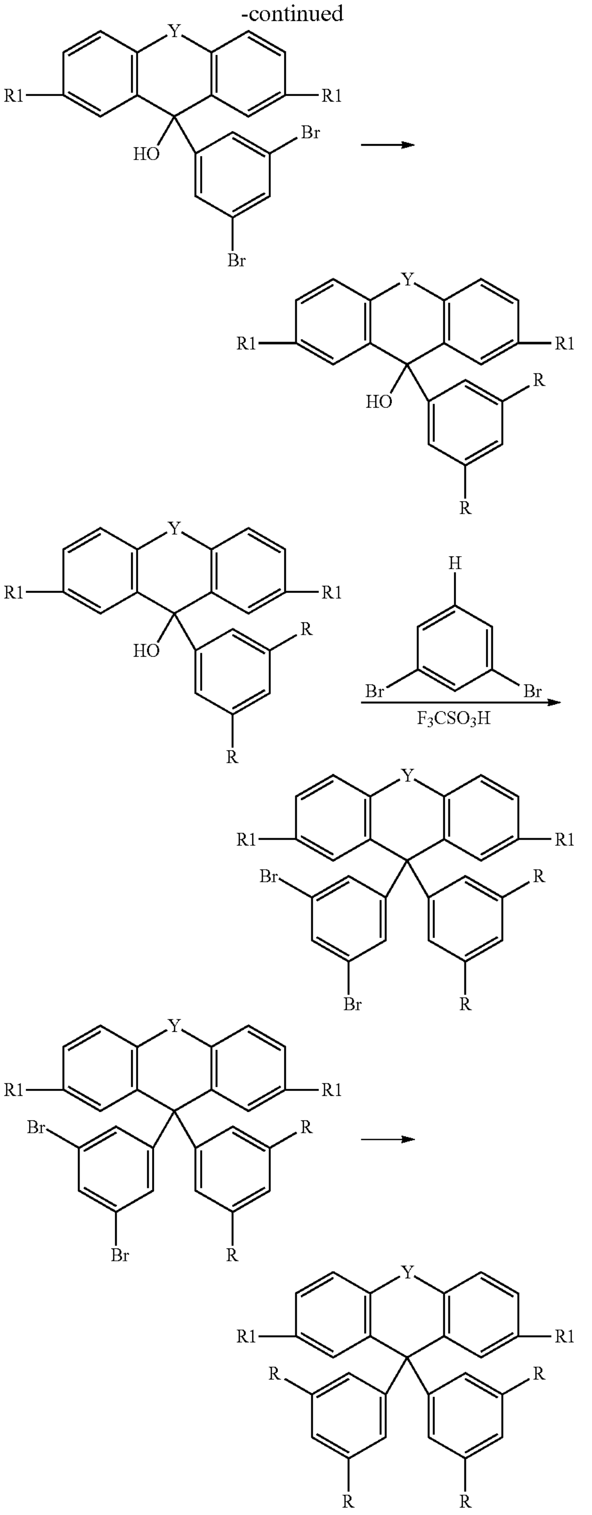

The corresponding indenofluorene derivatives, indenocarbazole derivatives and the other derivatives of the formula (1) can be synthesised correspondingly.

The invention furthermore relates to a process for the preparation of the compounds of the formula (1) comprising the reaction of bis(3,5-dibromo)-benzophenone with a substituted or unsubstituted 2-lithiobiphenyl, 2-lithiodiphenyl ether, 2-lithiodiphenyl thioether, 2-(2-lithiophenyl)-2-phenyl-1,3-dioxolane, 2-lithiophenyldiphenylamine or the corresponding Grignard compound to give the triarylmethanols, followed by cyclisation under acidic conditions and optionally followed by further reaction of the bromine groups.

The compounds according to the invention described above, in particular compounds which are substituted by reactive leaving groups, such as bromine, iodine, triflate, tosylate, boronic acid or boronic acid ester, can be used as monomers for the production of corresponding dimers, trimers, tetramers, pentamers, oligomers, polymers or as core of dendrimers. The oligomerisation or polymerisation here is preferably carried out via the halogen functionality or the boronic acid functionality. This applies, in particular, to compounds of the formula (4) in which the radicals $R^1$ each stand for a reactive leaving group, in particular selected from the groups mentioned above.

The invention therefore furthermore relates to dimers, trimers, tetramers, pentamers, oligomers, polymers or dendrimers containing one or more compounds of the formula (1), where one or more radicals $R^1$ or $R^2$ represent bonds between the compounds of the formula (1) in the dimer, trimer, tetramer or pentamer or bonds from the compound of the formula (1) to the polymer, oligomer or dendrimer or where this bonding takes place via substituents on the groups R. For the purposes of this invention, an oligamer is taken to mean a compound which has at least six units of the formula (1). The polymers, oligomers or dendrimers may be conjugated, partially conjugated or non-conjugated. The trimers, tetramers, pentamers, oligomers or polymers may be linear or branched. In the linearly linked structures, the units of the formula (1) may be linked directly to one another or linked to one another via a divalent group, for example via a substituted or unsubstituted alkylene group, via a heteroatom or via a divalent aromatic or heteroaromatic group. In branched structures, for example, three or more units of the formula (1) may be linked via a trivalent or polyvalent group, for example via a trivalent or polyvalent aromatic or heteroaromatic group, to give a branched trimer, tetramer, pentamer, oligomer or polymer.

For the recurring units of the formula (1) in dimers, trimers, tetramers, pentamers, oligomers and polymers, the same preferences as described above apply. Preferred recurring units here are therefore also the units of the formulae mentioned above.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The polymers, oligomers and dendrimers usually also contain further units, for example emitting (fluorescent or phosphorescent) units, such as, for example, vinyltriarylamines (for example in accordance with WO 07/068325) or phosphorescent metal complexes (for example in accordance with WO 06/003000), and/or charge-transport units. The recurring units according to the invention are particularly suitable here as charge-transport units for holes if one or more groups R stand for $NAr_2$.

The present invention furthermore relates to mixtures comprising at least one compound of the formula (1) or a corresponding dimer, trimer, tetramer, pentamer, oligomer or polymer and at least one further compound. The further compound may be, for example, a fluorescent or phosphorescent dopant if the compound of the formula (1) is used as matrix material. Suitable fluorescent and phosphorescent dopants are mentioned below in connection with the organic electroluminescent devices and are also preferred for the mixtures according to the invention. The further compound may also be a dopant if the compound of the formula (1) is a hole-transport or electron-transport compound. Suitable dopants are mentioned below in connection with the organic electroluminescent devices.

The present invention again furthermore relates to solutions comprising at least one compound of the formula (1) or a corresponding dimer, trimer, tetramer, pentamer, oligomer or polymer and at least one organic solvent. Solutions of this type are necessary for the production of the organic electronic device from solution, for example by spin coating or by printing processes.

The compounds of the formula (1) according to the invention and corresponding dimers, trimers, tetramers, pentamers, oligomers, polymers or dendrimers are suitable for use in electronic devices, in particular in organic electroluminescent devices (OLEDs, PLEDs). Depending on the substitution, the compounds are employed in various functions and layers. The preferred embodiments here conform to the formulae mentioned above.

The invention therefore furthermore relates to the use of compounds of the formula (1) or corresponding dimers, trimers, tetramers, pentamers, oligomers, polymers or dendrimers in electronic devices, in particular in organic electroluminescent devices.

The invention again furthermore relates to organic electronic devices comprising at least one compound of the formula (1) or a corresponding dimer, trimer, tetramer, pentamer, oligomer, polymer or dendrimer, in particular organic electroluminescent devices comprising anode, cathode and at least one emitting layer, characterised in that at least one organic layer, which may be an emitting layer or another layer, comprises at least one compound of the formula (1) or a corresponding dimer, trimer, tetramer, pentamer, oligomer, polymer or dendrimer.

Apart from the cathode, anode and emitting layer, the organic electroluminescent device may also comprise further layers. These are, for example, selected from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. Furthermore, the layers, in particular the charge-transport layers, may also be doped. The doping of the layers may be advantageous for improved charge transport. However, it should be pointed out here that each of these layers does not necessarily have to be present, and the choice of the layers is always dependent on the compounds used and in particular also on whether the device is a fluorescent or phosphorescent electroluminescent device.

In a further preferred embodiment of the invention, the organic electroluminescent device comprises a plurality of emitting layers, where at least one organic layer comprises at least one compound of the formula (1). These emission layers particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where at least one of these layers comprises at least one compound of the formula (1) and where the three layers exhibit blue, green and orange or red emission (for the basic structure, see, for example, WO 05/011013). Emitters which have broad-band emission bands and thus exhibit white emission are likewise suitable for white emission.

In a preferred embodiment of the invention, the compounds of the formula (1) are employed as matrix material for fluorescent or phosphorescent compounds in an emitting layer. In the case of a matrix material for phosphorescent compounds, one or more groups R and/or $R^1$ preferably stand for C(═O)Ar, $N(Ar)_2$, S(═O)Ar, $S(═O)_2Ar$ or $P(═O)Ar_2$. The same preferences apply to the groups R and $R^1$ in structures of the formulae (2), (3) and (4). In the case of a matrix material for fluorescent compounds, one or more groups R and/or $R^1$ preferably stand for an aromatic or heteroaromatic ring system, in particular for an aromatic ring system containing anthracene. The same preferences apply to the groups R and $R^1$ in structures of the formulae mentioned above.

In a system comprising matrix and dopant, a matrix material is taken to mean the component which is present in the system in the higher proportion. In a system comprising one matrix and a plurality of dopants, the matrix is taken to mean the component whose proportion in the mixture is the highest.

In a preferred embodiment of the invention, the matrix employed is a mixture, where at least one component of this mixture is a compound of the formula (1). It is preferred for one component of this mixture to be a hole-transport compound and for the other to be an electron-transport compound. Preferred hole-transport compounds are aromatic amines and carbazole derivatives. Preferred electron-transport compounds are aromatic ketones.

If the compound of the formula (1) is employed as matrix material for an emitting compound in an emitting layer, it can be employed in combination with one or more phosphorescent materials (triplet emitters). For the purposes of this invention, phosphorescence is taken to mean luminescence from an excited state with relatively high spin multiplicity, i.e. a spin state >1, in particular from an excited triplet state. For the purposes of this invention, all, in particular luminescent, iridium, platinum, osmium, gold and copper compounds are referred to as phosphorescent materials. The mixture comprising the compound of the formula (1) and the emitting compound then comprises between 99 and 1% by weight, preferably between 98 and 10% by weight, particularly preferably between 97 and 60% by weight, in particular between 95 and 85% by weight, of the compound of the formula (1), based on the mixture as a whole comprising emitter and matrix material. Correspondingly, the mixture comprises between 1 and 99% by weight, preferably between 2 and 90% by weight, particularly preferably between 3 and 40% by weight, in particular between 5 and 15% by weight, of the emitter, based on the mixture as a whole comprising emitter and matrix material.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614 and WO 05/033244. The compounds according to the invention mentioned above are furthermore suitable as emitters. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

If the compound of the formula (1) is employed as matrix material for fluorescent compounds, the proportion of matrix material in the emitting layer is between 50.0 and 99.9% by weight, preferably between 80.0 and 99.5% by weight, particularly preferably between 90.0 and 99.0% by weight. Correspondingly, the proportion of dopant is between 0.1 and 50.0% by weight, preferably between 0.1 and 20.0% by weight, particularly preferably between 0.5 and 15% by weight, very particularly preferably between 1.0 and 10.0% by weight.

Preferred dopants are selected from the class of the monostyrylamines, distyrylamines, tristyrylamines, tetrastyrylamines, styrylphosphines, styryl ethers and arylarnines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. Preferably, at least one of these aromatic or heteroaromatic ring systems is a condensed ring system, preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which a diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are selected from indenofluorenamines or indenofluorenediamines, for example in accordance with WO 06/122630, benzoindenofluorenamines or benzoindenofluorenediamines, for example in accordance with WO 08/006449, and dibenzoindenofluorenamines or dibenzoindenofluorenediamines, for example in accordance with WO 07/140847. Examples of dopants from the class of the styrylamines are substituted or unsubstituted tristilbenamines or the dopants which are described in WO 06/000388, WO 06/058737, WO 06/000389, WO 07/065549 and WO 07/115610.

In a further embodiment of the invention, the compounds of the formula (1) are employed as hole-transport material or as hole-injection material or as electron-blocking material or as exciton-blocking material. The compounds are then preferably substituted by at least one group $N(Ar)_2$, preferably by at least two groups $N(Ar)_2$, and/or contain further groups which improve hole transport. It is particularly preferred here for all groups R to stand for $N(Ar)_2$. The groups $N(Ar)_2$ are preferably selected from the formulae (5) and (6) described above. This applies, in particular, to the radicals R on the structures of the formulae mentioned above. Further preferred groups which improve hole transport are, for example, the groups $N(R^1)$, S or O, in particular $N(R^1)$, as bridge Y or electron-rich heteroaromatic groups, in particular thiophene, pyrrole or furan as group R or $R^1$. The compound is preferably employed in a hole-transport or hole-injection or electron-blocking or exciton-blocking layer. For the purposes of this invention, a hole-injection layer is a layer which is directly adjacent to the anode. For the purposes of this invention, a hole-transport layer is a layer which is between a hole-injection layer and an emission layer. For the purposes of this invention, an electron-blocking or exciton-blocking layer is a layer which is directly adjacent to an emitting layer on the anode side. If the compounds of the formula (1) are used as hole-transport or hole-injection material, it may be preferred for them to be doped with electron-acceptor compounds, for example with $F_4$-TCNQ, or with compounds as described in EP 1476881 or EP 1596445.

In still a further embodiment of the invention, the compounds of the formula (1) are employed as electron-transport material or as hole-blocking material in an electron-transport layer or hole-blocking layer. It is preferred here for the group Y to stand for C═O, P(═O), SO or $SO_2$ and/or for at least one of the substituents R and/or $R^1$ to stand for a heteroaryl group which represents an electron-deficient heterocycle, such as, for example, imidazole, pyrazole, thiazole, benzimidazole, benzothiazole, triazole, oxadiazole, benzothiadiazole, phenanthroline, etc., or for C(═O)Ar, P(═O)$Ar_2$, S(═O)Ar or $S(O)_2$Ar. It may furthermore be preferred for the compound to be doped with electron-donor compounds. For the purposes of this invention, a hole-blocking layer is a layer which is between an emitting layer and an electron-transport layer and is directly adjacent to the emitting layer. If the compound of the formula (1) is employed as electron-transport material, it may be preferred to employ this as a mixture with a further compound. Preferred mixture components are alkali metal compounds, preferably lithium compounds, particularly preferably Liq (lithium quinolinate) or Liq derivatives.

Recurring units of the formula (1) can likewise be employed either as polymer backbone, as hole-transporting unit and/or as electron-transporting unit in polymers. The preferred substitution patterns here correspond to those described above.

Preference is furthermore given to an organic electroluminescent device, characterised in that one or more layers are applied by a sublimation process, in which the materials are vapour-deposited in vacuum sublimation units at a pressure below $10^{-5}$ mbar, preferably below $10^{-6}$ mbar. However, it should be noted that the pressure may also be even lower, for example below $10^{-7}$ mbar.

Preference is likewise given to an organic electroluminescent device, characterised in that one or more layers are applied by the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved by suitable substitution of the compounds. It is possible here not only to apply solutions of individual materials, but also solutions which comprise a plurality of compounds, for example matrix material and dopant.

The compounds according to the invention have the following surprising advantages over the prior art when used in organic electroluminescent devices:

1. The compounds according to the invention have high thermal stability and can be sublimed without decomposition.
2. The compounds according to the invention, in particular those which contain diarylamino substituents as groups R, result in a considerable improvement in the efficiency compared with materials in accordance with the prior art when used in an electron/exciton-blocking layer in a phosphorescent electroluminescent device.
3. The compounds according to the invention, in particular those which are substituted by diarylamino groups and/or which contain a single bond or S, O or N($R^1$) as group Y and/or which are substituted by electron-rich heteroaromatic groups, are very highly suitable for use as hole-injection and hole-transport material and result in a reduction in the operating voltage.
4. The OLEDs produced with the compounds according to the invention generally have a very long lifetime.
5. The OLEDs produced with the compounds according to the invention generally have very high quantum efficiency.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention in other electronic devices, for example in organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photo receptors.

The present invention likewise relates to the use of the compounds according to the invention in the corresponding devices and to these devices themselves.

The invention is described in greater detail by the following examples without wishing to restrict it thereby. The person skilled in the art, without being inventive, will be able to prepare further compounds according to the invention and use them in organic electronic devices.

EXAMPLES

The following syntheses are carried out—unless indicated otherwise—under a protective-gas atmosphere in dried solvents. The solvents and reagents can be purchased from ALDRICH or ABCR. The precursor 3,3',5,5'-tetrabromobenzophenone is prepared as described in *Eur. J. Org. Chem.* 2006, 2523-2529.

Example 1

Synthesis of 9,9-bis(3,5-dibromophenyl)fluorene

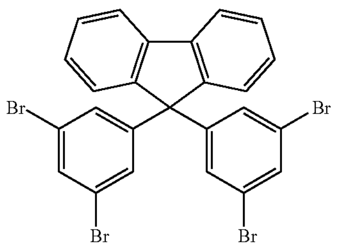 [SMILES: Brc1cc(Br)cc(C2(c3cc(Br)cc(Br)c3)c3ccccc3-c3ccccc32)c1]

The corresponding Grignard compound is prepared from 144.5 g (620 mmol) of 2-bromobiphenyl and 15.3 g (580 mmol) of magnesium in a mixture of 500 ml of tetrahydrofuran and 250 ml of dimethoxyethane. A suspension of 224.0 g (450 mmol) of bis(3,5-dibromophenyl) ketone in 1000 ml of tetrahydrofuran is then added at room temperature, and the mixture is stirred for a further twelve hours. The solvent is removed in vacuo, 1000 ml of glacial acetic acid and 5 ml of hydrogen bromide are added to the residue, and the mixture is stirred for one hour. The suspension is heated under reflux for half an hour and stirred at room temperature for twelve hours. The solid is filtered off with suction, washed three times with 300 ml of ethanol and recrystallised twice from toluene. Yield: 183.2 g (289 mmol), 64.3%, purity about 99.8% (HPLC).

The following compounds according to the invention are obtained analogously to Example 1 from corresponding bromides (Examples 2 and 3):

| Ex. | Bromide | Product | Yield |
|---|---|---|---|
| 2 | 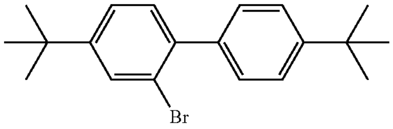 [SMILES: CC(C)(C)c1ccc(-c2ccc(C(C)(C)C)cc2Br)cc1] | 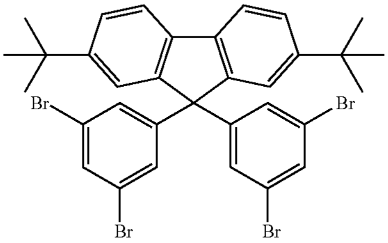 [SMILES: CC(C)(C)c1ccc2c(c1)C(c1cc(Br)cc(Br)c1)(c1cc(Br)cc(Br)c1)c1cc(C(C)(C)C)ccc1-2] | 74.8% |
| 3 | 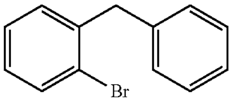 [SMILES: Brc1ccccc1Cc1ccccc1] | 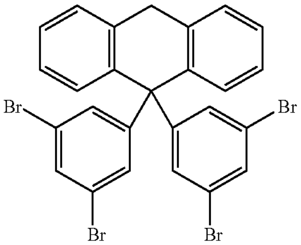 [SMILES: Brc1cc(Br)cc(C2(c3cc(Br)cc(Br)c3)c3ccccc3Cc3ccccc32)c1] | 58.7% |

Example 4

Synthesis of 9,9-bis(3,5-diphenylphenyl)fluorene

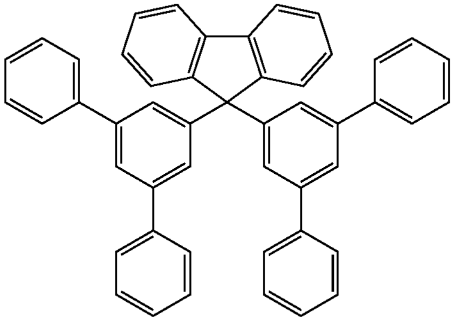 [SMILES: c1ccc(-c2cc(-c3ccccc3)cc(C3(c4cc(-c5ccccc5)cc(-c5ccccc5)c4)c4ccccc4-c4ccccc43)c2)cc1]

1.0 g (3.3 mmol) of tri-o-tolylphosphine and 0.5 g (2.2 mmol) of palladium-(II) acetate are added to a well-stirred suspension of 30.4 g (48 mmol) of 9,9-bis(3,5-dibromophenyl)fluorene, 35.4 g (290 mmol) of phenylboronic acid and 121.0 g (570 mmol) of tripotassium phosphate in a mixture of 300 ml of toluene, 300 ml of 1,4-dioxane and 300 ml of water, and the mixture is subsequently heated under reflux for three hours. After cooling, the organic phase is separated off, washed three times with 150 ml of water each time and filtered through silica gel. The solvent is removed in vacuo, and the residue is taken up in 200 ml of ethanol, filtered off with suction and washed three times with 100 ml of ethanol. The solid is recrystallised three times from chlorobenzene and, after drying, sublimed twice in vacuo ($p=1\times10^{-5}$ mbar, T=320° C.). Yield: 11.1 g (18 mmol), 37.1%, purity about 99.9% (HPLC).

The following compounds according to the invention are obtained analogously to Example 4 from the corresponding boronic acids (Examples 5-7):

| Ex. | Boronic acid | Fluorene | Product | Yield |
|---|---|---|---|---|
| 5 | 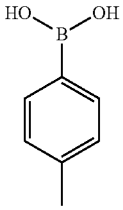 | 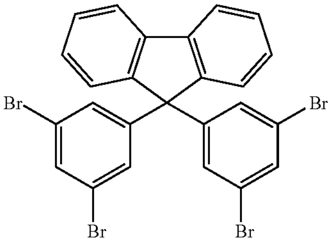 [SMILES: Brc1cc(Br)cc(C2(c3cc(Br)cc(Br)c3)c3ccccc3-c3ccccc32)c1] | 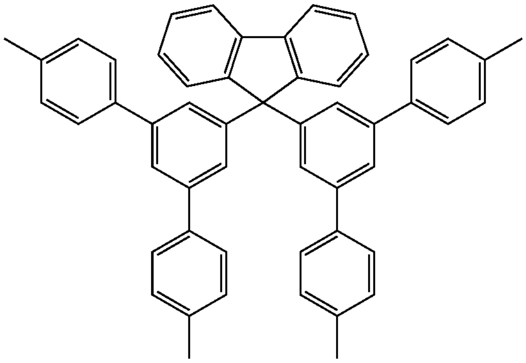 | 48.2% |

-continued

| Ex. | Boronic acid | Fluorene | Product | Yield |
|---|---|---|---|---|
| 6 | 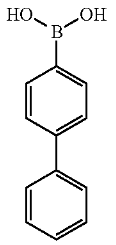 | 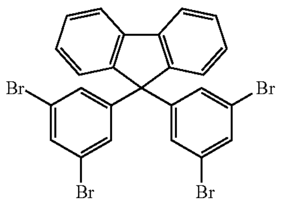 [SMILES: Brc1cc(Br)cc(C2(c3cc(Br)cc(Br)c3)c3ccccc3-c3ccccc32)c1] | 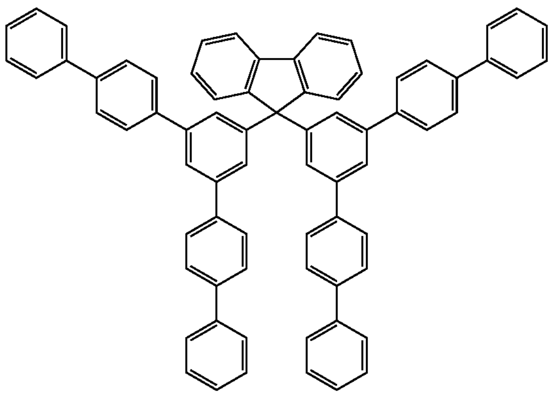 [SMILES: c1ccc(-c2ccc(-c3cc(-c4ccc(-c5ccccc5)cc4)cc(C4(c5cc(-c6ccc(-c7ccccc7)cc6)cc(-c6ccc(-c7ccccc7)cc6)c5)c5ccccc5-c5ccccc54)c3)cc2)cc1] | 34.6% |
| 7 | 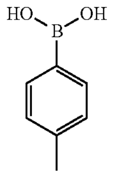 | 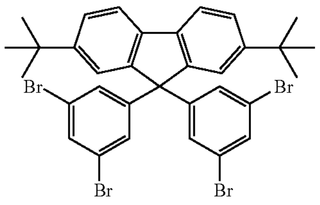 [SMILES: CC(C)(C)c1ccc2c(c1)C(c1cc(Br)cc(Br)c1)(c1cc(Br)cc(Br)c1)c1cc(C(C)(C)C)ccc1-2] | 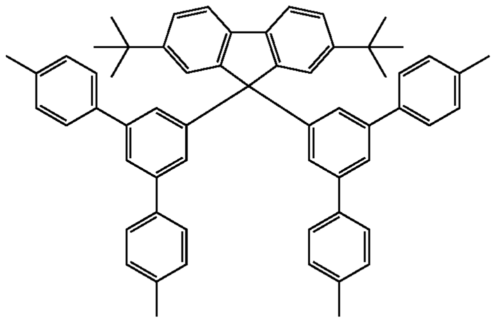 | 42.9% |

Example 8

Synthesis of 9,9-bis(3,5-diphenylaminophenyl)fluorene

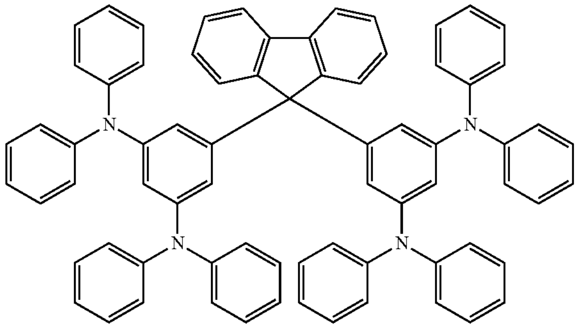 [SMILES: c1ccc(N(c2ccccc2)c2cc(N(c3ccccc3)c3ccccc3)cc(C3(c4cc(N(c5ccccc5)c5ccccc5)cc(N(c5ccccc5)c5ccccc5)c4)c4ccccc4-c4ccccc43)c2)cc1]

101 mg (0.50 mmol) of tri-tert-butylphosphine and 56 mg (0.25 mmol) of palladium(II) acetate are added to a well-stirred suspension of 25.4 g (40 mmol) of 9,9-bis(3,5-dibromophenyl)fluorene, 33.8 g (200 mmol) of diphenylamine and 21.1 g (220 mmol) of [lacuna] in 500 ml of toluene, and the mixture is heated under reflux for five hours. After cooling, the solution is filtered through silica gel and subsequently evaporated to dryness in vacuo. The residue is stirred at 60° C. for one hour in 600 ml of a 1:1 mixture of ethanol and water, filtered off with suction, washed five times with 250 ml of ethanol and dried in vacuo. The beige solid is recrystallised five times from dimethylformamide and three times from chlorobenzene, dried in vacuo and subsequently sublimed twice ($p=1\times10^{-5}$ mbar, T=350° C.), Yield: 10.2 g (10 mmol), 25.0%, purity 99.9% (HPLC), $T_g$=99.8° C.

The following compounds according to the invention are obtained analogously to Example 8 from the corresponding amines and the corresponding fluorenes (Examples 9-13):

| Ex. | Amine | Fluorene | Product | Yield |
|---|---|---|---|---|
| 9 | 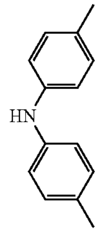 | 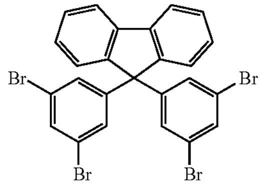 [SMILES: Brc1cc(Br)cc(C2(c3cc(Br)cc(Br)c3)c3ccccc3-c3ccccc32)c1] | 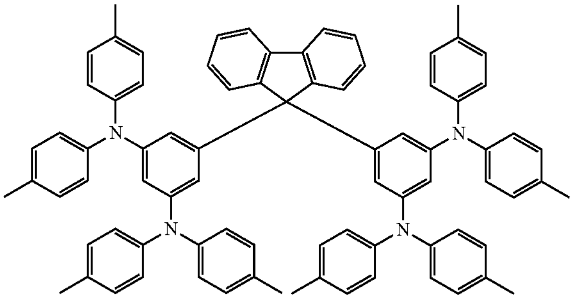 | 59.8% |
| 10 | 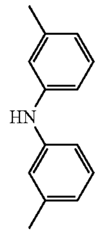 | 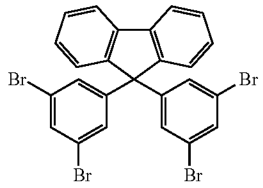 [SMILES: Brc1cc(Br)cc(C2(c3cc(Br)cc(Br)c3)c3ccccc3-c3ccccc32)c1] | 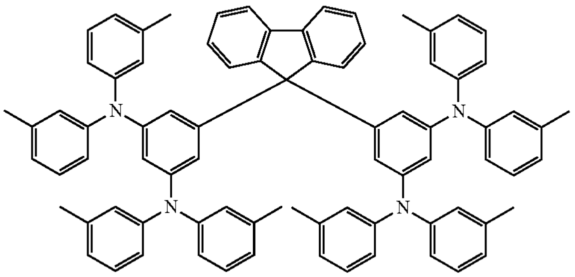 | 48.3% |
| 11 | 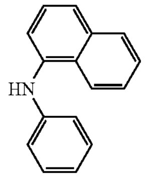 [SMILES: c1ccc(Nc2cccc3ccccc23)cc1] | 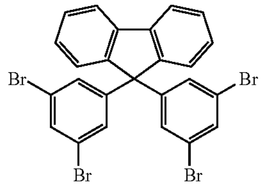 [SMILES: Brc1cc(Br)cc(C2(c3cc(Br)cc(Br)c3)c3ccccc3-c3ccccc32)c1] | 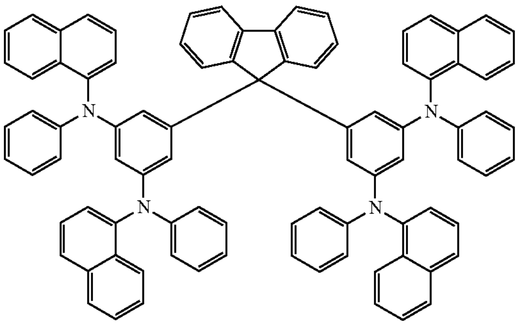 [SMILES: c1ccc(N(c2cc(N(c3ccccc3)c3cccc4ccccc34)cc(C3(c4cc(N(c5ccccc5)c5cccc6ccccc56)cc(N(c5ccccc5)c5cccc6ccccc56)c4)c4ccccc4-c4ccccc43)c2)c2cccc3ccccc23)cc1] | 53.0% |
| 12 | 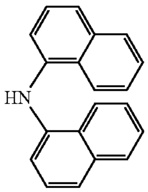 [SMILES: c1ccc2c(Nc3cccc4ccccc34)cccc2c1] | 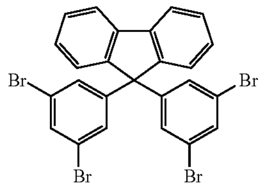 [SMILES: Brc1cc(Br)cc(C2(c3cc(Br)cc(Br)c3)c3ccccc3-c3ccccc32)c1] | 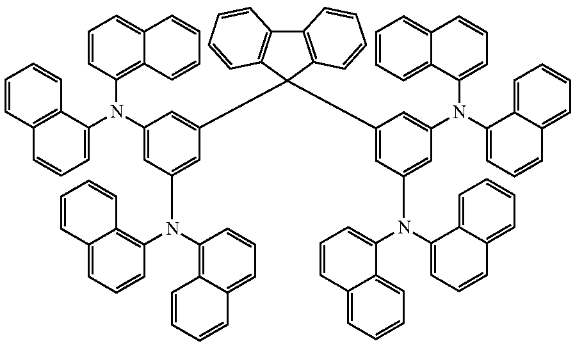 [SMILES: c1ccc2c(c1)-c1ccccc1C2(c1cc(N(c2cccc3ccccc23)c2cccc3ccccc23)cc(N(c2cccc3ccccc23)c2cccc3ccccc23)c1)c1cc(N(c2cccc3ccccc23)c2cccc3ccccc23)cc(N(c2cccc3ccccc23)c2cccc3ccccc23)c1] | 38.1% |
| 13 | 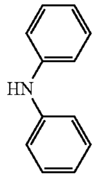 [SMILES: c1ccc(Nc2ccccc2)cc1] | 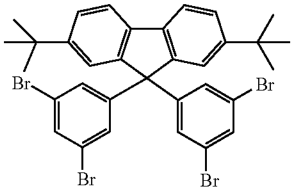 [SMILES: CC(C)(C)c1ccc2c(c1)C(c1cc(Br)cc(Br)c1)(c1cc(Br)cc(Br)c1)c1cc(C(C)(C)C)ccc1-2] | 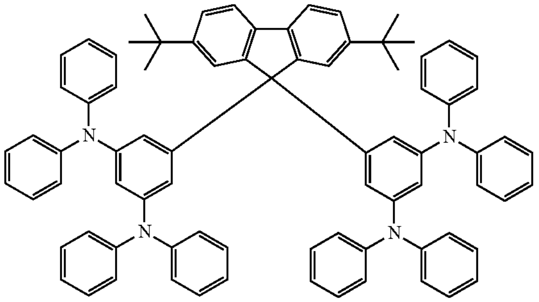 [SMILES: CC(C)(C)c1ccc2c(c1)C(c1cc(N(c3ccccc3)c3ccccc3)cc(N(c3ccccc3)c3ccccc3)c1)(c1cc(N(c3ccccc3)c3ccccc3)cc(N(c3ccccc3)c3ccccc3)c1)c1cc(C(C)(C)C)ccc1-2] | 62.7% |

Example 14

Synthesis of 9,9-bis(3,5-dicarbazol-N-yl)fluorene

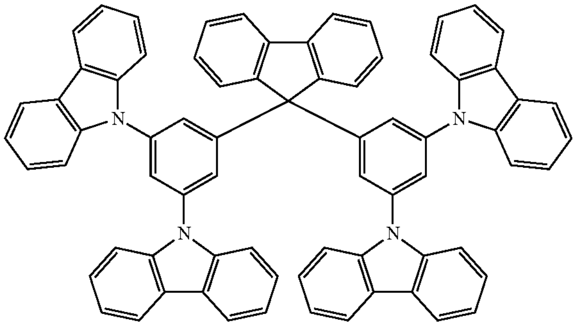 [SMILES: c1ccc2c(c1)-c1ccccc1C2(c1cc(-n2c3ccccc3c3ccccc32)cc(-n2c3ccccc3c3ccccc32)c1)c1cc(-n2c3ccccc3c3ccccc32)cc(-n2c3ccccc3c3ccccc32)c1]

A suspension of 50.7 g (80 mmol) of 9,9-bis(3,5-dibromophenyl)fluorene, 78.6 g (470 mmol) of carbazole and 201.7 g (950 mmol) of tripotassium phosphate is stirred vigorously in 1000 ml of p-xylene with 500 g of glass beads. 1.62 g (8.0 mmol) of tri-tert-butylphosphine and 894 mg (4.0 mmol) of palladium(II) acetate are added to the suspension, which is then heated under reflux for five days. After cooling, 1000 ml of water are added, and the mixture is stirred for twelve hours and then filtered. The organic phase is separated off, washed three times with 200 ml of water and subsequently evaporated in vacuo to give a viscous oil. On stirring with 300 ml of ethanol, a crystalline solid forms, which is filtered off with suction and washed three times with 250 ml of ethanol. A solution of the solid in 350 ml of dimethylformamide is added dropwise to 1500 ml of boiling ethanol. After cooling, the solid is filtered off with suction, recrystallised three times from chlorobenzene, dried in vacuo and then sublimed twice in vacuo ($p=1\times10^{-5}$ mbar, T=370° C.). Yield: 33.2 g (34 mmol), 42.4%, purity 99.8% (HPLC).

The following compounds according to the invention are obtained analogously to Example 14 from the corresponding carbazole derivatives (Examples 15-16):

| Ex. | Starting material | Product | Yield |
|---|---|---|---|
| 15 | 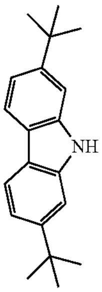 [SMILES: CC(C)(C)c1ccc2c(c1)[nH]c1cc(C(C)(C)C)ccc12] | 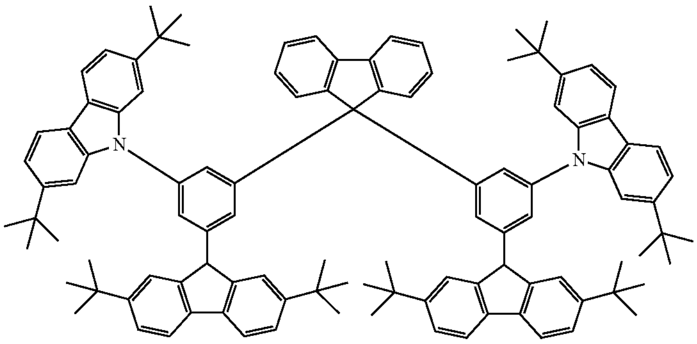 [SMILES: CC(C)(C)c1ccc2c(c1)C(c1cc(-n3c4cc(C(C)(C)C)ccc4c4ccc(C(C)(C)C)cc43)cc(C3(c4cc(C5c6cc(C(C)(C)C)ccc6-c6ccc(C(C)(C)C)cc65)cc(-n5c6cc(C(C)(C)C)ccc6c6ccc(C(C)(C)C)cc65)c4)c4ccccc4-c4ccccc43)c1)c1cc(C(C)(C)C)ccc1-2] | 51.3% |
| 16 | 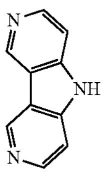 | 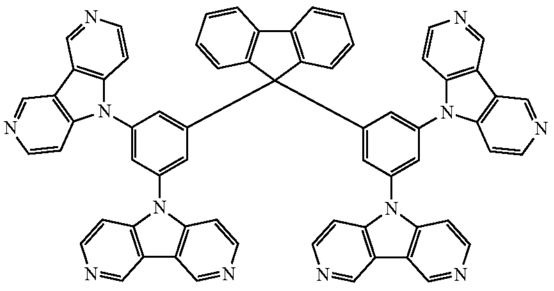 [SMILES: c1ccc2c(c1)-c1ccccc1C2(c1cc(-n2c3ccncc3c3cnccc32)cc(-n2c3ccncc3c3cnccc32)c1)c1cc(-n2c3ccncc3c3cnccc32)cc(-n2c3ccncc3c3cnccc32)c1] | 21.4% |

Example 17

Synthesis of 9,9-bis((3,5-bisbenzoyl)phenyl)fluorene

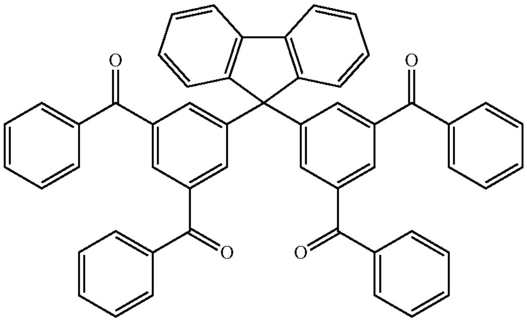 [SMILES: O=C(c1ccccc1)c1cc(C(=O)c2ccccc2)cc(C2(c3cc(C(=O)c4ccccc4)cc(C(=O)c4ccccc4)c3)c3ccccc3-c3ccccc32)c1]

67.5 ml of n-butyllithium (2.5 M in hexane) are added dropwise to a solution, cooled to −78° C., of 25.4 g (40 mmol) of 9,9-bis(3,5-dibromophenyl)-fluorene in 1000 ml of THF, and the mixture is subsequently stirred at −78° C. for 30 min. A mixture of 18.6 g (180 mmol) of benzonitrile and 50 ml of THF is then added rapidly, the mixture is stirred at −78° C. for a further 1 h and then allowed to warm to room temperature, 100 ml of 5 N hydrochloric acid are added, and the mixture is boiled under reflux for 5 h. After cooling, the THF is removed in vacuo in a rotary evaporator, and the residue is taken up in 500 ml of dichloromethane, washed with water and sat. sodium hydrogencarbonate solution until neutral, dried over magnesium sulfate and then filtered off over a short column with silica gel. The solvent is evaporated to about 50 ml in vacuo in a rotary evaporator, 300 ml of methanol are added, and the precipitated solid is filtered off with suction and washed once with 100 ml of methanol. After drying, the beige solid is recrystallised five times from dimethylformamide, dried in vacuo and subsequently sublimed twice ($p=1\times10^{-5}$ mbar, T=360° C.). Yield: 14.3 g (19 mmol), 48.6%, purity 99.9% (HPLC).

The following compounds according to the invention are obtained analogously to Example 17 from the corresponding nitriles (Examples 18 and 19):

| Ex. | Amine | Product | Yield |
| --- | --- | --- | --- |
| 18 | 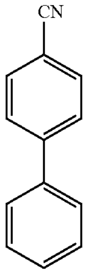 [SMILES: N#Cc1ccc(-c2ccccc2)cc1] | 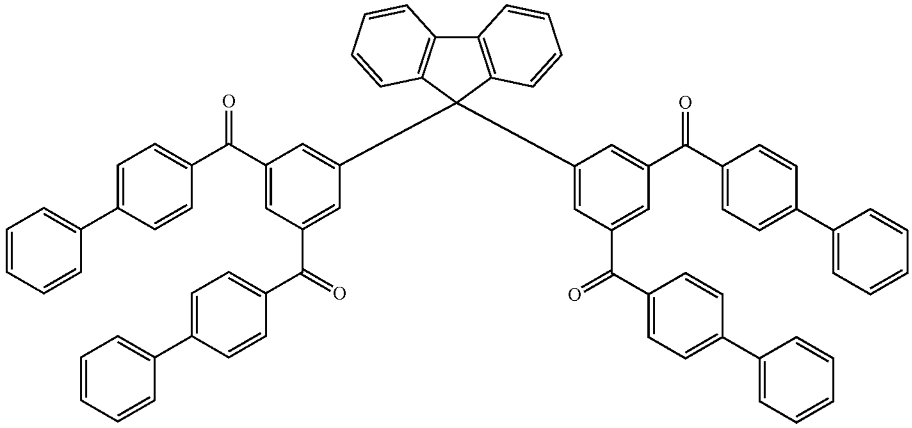 [SMILES: O=C(c1ccc(-c2ccccc2)cc1)c1cc(C(=O)c2ccc(-c3ccccc3)cc2)cc(C2(c3cc(C(=O)c4ccc(-c5ccccc5)cc4)cc(C(=O)c4ccc(-c5ccccc5)cc4)c3)c3ccccc3-c3ccccc32)c1] | 51.8% |
| 19 | 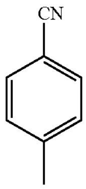 | 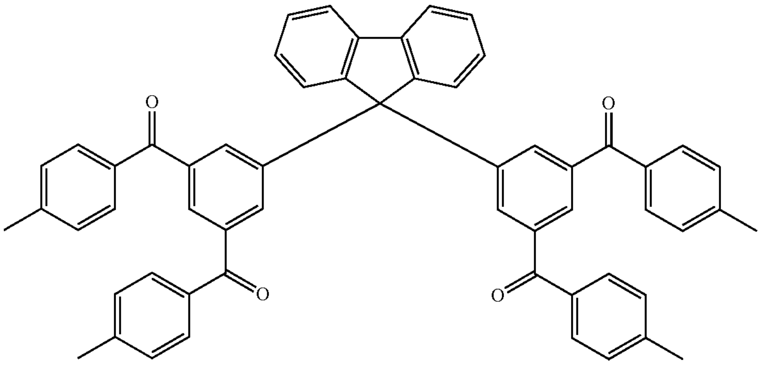 | 37.0% |

Example 20

Synthesis of 9,9-bis((3,5-bisdiphenylphosphinyl)phenyl)-fluorene

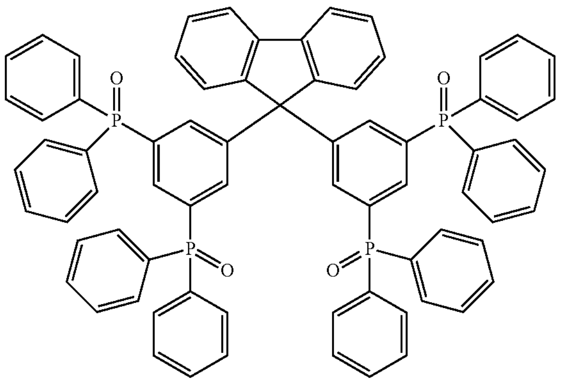 [SMILES: O=P(c1ccccc1)(c1ccccc1)c1cc(C2(c3cc(P(=O)(c4ccccc4)c4ccccc4)cc(P(=O)(c4ccccc4)c4ccccc4)c3)c3ccccc3-c3ccccc32)cc(P(=O)(c2ccccc2)c2ccccc2)c1]

67.5 ml of n-butyllithium (2.5 M in hexane) are added dropwise to a solution, cooled to −78° C., of 25.4 g (40 mmol) of 9,9-bis(3,5-dibromophenyl)-fluorene in 1000 ml of THF, and the mixture is subsequently stirred at −78° C. for 30 min. A mixture of 39.7 g (180 mmol) of chlorodiphenylphosphine and 50 ml of THF is then added rapidly, the mixture is stirred at −78° C. for a further 1 h and then allowed to warm to room temperature, the THF is removed completely in vacuo in a rotary evaporator, the residue is taken up in 500 ml of ethyl acetate, 150 ml of 10% hydrogen peroxide are added dropwise with vigorous stirring, the mixture is stirred for a further 16 h, the aqueous phase is separated off, the solvent is evaporated to about 50 ml in vacuo in a rotary evaporator, 300 ml of methanol are added, and the precipitated solid is filtered off with suction and washed once with 100 ml of methanol. After drying, the beige solid is recrystallised five times from chlorobenzene, dried in vacuo and subsequently sublimed twice ($p=1\times10^{-5}$ mbar, T=390° C.). Yield: 12.0 g (11 mmol), 26.8%, purity 99.9% (HPLC).

The following compound according to the invention is obtained analogously to Example 20 from the corresponding chlorophosphine (Example 21):

| Ex. | Amine | Product | Yield |
|---|---|---|---|
| 21 | 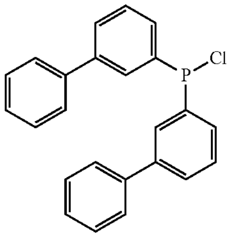 [SMILES: ClP(c1cccc(-c2ccccc2)c1)c1cccc(-c2ccccc2)c1] | 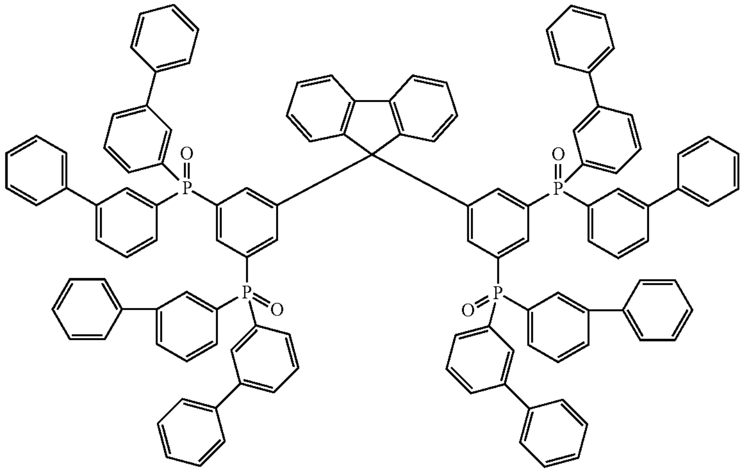 [SMILES: O=P(c1cccc(-c2ccccc2)c1)(c1cccc(-c2ccccc2)c1)c1cc(C2(c3cc(P(=O)(c4cccc(-c5ccccc5)c4)c4cccc(-c5ccccc5)c4)cc(P(=O)(c4cccc(-c5ccccc5)c4)c4cccc(-c5ccccc5)c4)c3)c3ccccc3-c3ccccc32)cc(P(=O)(c2cccc(-c3ccccc3)c2)c2cccc(-c3ccccc3)c2)c1] | 27.6% |

Example 22

Synthesis of 9,9-bis((3,5-bis-N-phenylbenzimidazol-2-yl)-phenyl)fluorene

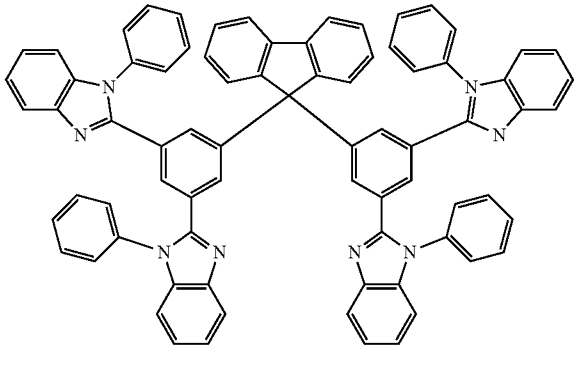

a) 9,9-Bis(3,5-dicyanophenyl)fluorene

A suspension of 63.4 g (100 mmol) of 9,9-bis(3,5-dibromophenyl)fluorene, 58.7 g (500 mmol) of zinc cyanide, 3.3 g (50 mmol) of zinc and 11.6 g (10 mmol) of tetrakis(triphenylphosphino)palladium(0) in 1000 ml of dimethylacetamide is stirred at 140° C. for 60 h. After cooling, 1000 ml of conc. ammonia solution are added, the mixture is stirred for a further 1 h and filtered with suction, and the solid is washed with 500 ml of water and three times with 100 ml of ethanol and dried in vacuo. Yield: 39.8 g (95 mmol), 95.1%, purity 98% according to 1H-NMR.

b) 9,9-Bis(3,5-dicarboxyphenyl)fluorene

A suspension of 39.8 g (95 mmol) of 9,9-bis(3,5-dicyanophenyl)fluorene is heated under reflux in a solution of 40 g of sodium hydroxide in a mixture of 300 ml of ethanol and 100 ml of water until a clear solution forms (about 10 h). After cooling, the pH is adjusted to 1 by addition of 5 N hydrochloric acid. The precipitated solid is filtered off with suction, washed with water until the mother liquor runs off with pH=4-5, sucked dry and then dried azeotropically with toluene. Yield: 44.5 g (90 mmol), 94.8%, purity 98% according to $^{1}$H-NMR.

c) 9,9-Bis((3,5-bis-N-phenylbenzimidazol-2-yl)phenyl)fluorene 44.5 g (90 mmol) of 9,9-bis(3,5-dicarboxyphenyl)fluorene are suspended in 150 ml of thionyl chloride, and one drop of DMF is added to the suspension, which is subsequently warmed at 60° C. until the evolution of gas is complete. The excess thionyl chloride is then removed in vacuo, the residue is dissolved in 500 ml of dichloromethane, and a solution of 66.3 g (360 mmol) of N-phenyl-o-phenylenediamine in a mixture of 200 ml of dichloromethane and 150 ml of triethylamine is subsequently added dropwise. When the exothermic reaction has subsided, the mixture is stirred at room temperature for a further 16 h. The reaction mixture is washed with 500 ml of 1 N NaOH and then twice with 500 ml of water, dried over magnesium sulfate and then chromatographed on aluminium oxide (basic, activity grade 1) with dichloromethane. Finally, the product is recrystallised three times from chlorobenzene, dried in vacuo and then sublimed twice (p=1×10$^{-5}$ mbar, T=410° C.). Yield: 33.8 g (31 mmol), 31.0%, purity 99.9% (HPLC).

Example 23

Synthesis of 9,9-bis(4,6-diphenyltriazin-2-yl)fluorene

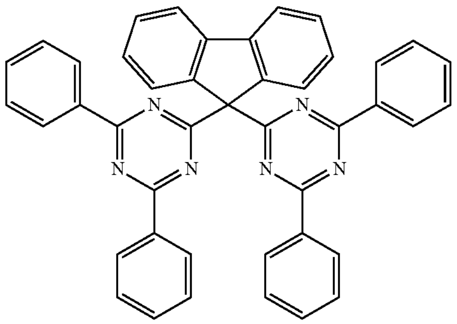 [SMILES: c1ccc(-c2nc(-c3ccccc3)nc(C3(c4nc(-c5ccccc5)nc(-c5ccccc5)n4)c4ccccc4-c4ccccc43)n2)cc1]

7.2 g (300 mmol) of sodium hydride are added to a solution of 16.6 g (100 mmol) of fluorene in 500 ml of THF. After addition of 0.5 ml of diisopropylamine, the mixture is stirred at room temperature for 1 h, a solution of 58.9 g (220 mmol) of 2-chloro-4,6-diphenyl-1,3,5-triazine is subsequently added dropwise, and the mixture is then stirred at 50° C. for 16 h. After cooling, the mixture is quenched by addition of 5 ml of water, the THF is stripped off in vacuo, the residue is dissolved in dichloromethane, and the organic phase is washed with water and then dried over magnesium sulfate. After removal of the dichloromethane, the residue is recrystallised four times from DMF, dried in vacuo and then sublimed twice (p=1×10$^{-5}$ mbar, T=340° C.). Yield: 17.0 g (27 mmol), 27.0%, purity 99.9% (HPLC).

Example 24

Synthesis of 10-phenyl-12,12-bis[1,1';3,1"]terphenyl-5'-yl-10,12-dihydro-10-azaindeno[2,1-b]fluorene

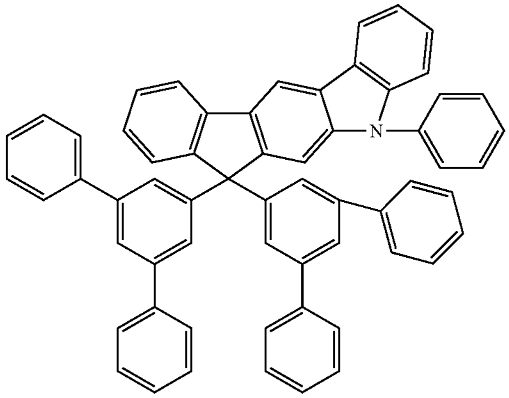 [SMILES: c1ccc(-c2cc(-c3ccccc3)cc(C3(c4cc(-c5ccccc5)cc(-c5ccccc5)c4)c4ccccc4-c4cc5c6ccccc6n(-c6ccccc6)c5cc43)c2)cc1]

a) 3-(2-Bromophenyl)-N-phenylcarbazole 1.1 g (1 mmol) of tetrakis(triphenylphosphino)palladium (0) are added to a mixture of 28.7 g (100 mmol) of N-phenylcarbazole-3-boronic acid, 36.1 ml (300 mmol) of 1,2-dibromobenzene in 150 ml of dioxane, 100 ml of 2-ethoxyethanol and 250 ml of 2 N sodium carbonate solution, and the mixture is heated under reflux for 16 h. After cooling, the organic phase is separated off, 500 ml of toluene are added, and the mixture is washed three times with 500 ml of water, dried over magnesium sulfate, filtered through silica gel and then freed from toluene and excess 1,2-dibromobenzene in vacuo. The residue is washed by stirring three times with hot ethanol. Yield: 26.7 g (67 mmol), 67.1%, purity 97% according to b) 12,12-Bis(3,5-dibromophenyl)-10-phenyl-10,12-dihydro-10-aza-indeno[2,1-b]fluorene 24.0 ml (60 mmol) of n-butyllithium (2.5 N in hexane) are added dropwise to a solution, cooled to −78° C., of 23.9 g (60 mmol) of 3-(2-bromophenyl)-N-phenylcarbazole in 500 ml of THF, the mixture is subsequently stirred at −78° C. for a further 30 min., and a solution of 38.0 g (60 mmol) of 9,9-bis-(3,5-dibromophenyl)fluorene in 100 ml of THF is then added dropwise. When the addition is complete, the mixture is allowed to warm to room temperature, the THF is removed in vacuo, the residue is taken up in 500 ml of glacial acetic acid, 5 ml of hydrogen bromide are added, and the suspension is heated under reflux for half an hour. After cooling, the solid is filtered off with suction, washed three times with 300 ml of ethanol and recrystallised once from toluene/ethanol. Yield: 36.2 g (45 mmol), 75.3%, purity about 97% (HPLC).

c) 10-Phenyl-12,12-bis[1,1';3,1"]terphenyl-5'-yl-10,12-dihydro-10-aza-indeno[2,1-b]fluorene Preparation analogous to Example 4. Instead of 30.4 g (48 mmol) of 9,9-bis(3,5-dibromophenyl)fluorene, 36.0 g (45 mmol) of 12,12-bis(3,5-dibromophenyl)-10-phenyl-10,12-dihydro-10-azaindeno[2,1-b]fluorene are used. The solid is recrystallised three times from NMP and, after drying, sublimed twice in vacuo ($p=1\times10^{-5}$ mbar, T=400° C.). Yield: 15.0 g (19 mmol), 42.3%, purity about 99.9% (HPLC).

Example 25

Production and Characterisation of Organic Electroluminescent Devices Comprising the Compounds According to the Invention Electroluminescent devices according to the invention can be produced as described, for example, in WO 05/003253. The results for various OLEDs are compared here. For better comparability, the basic structure, the materials used, the degree of doping and the layer thicknesses thereof are identical. The first device example describes a comparative standard in accordance with the prior art, in which the emission layer consists of the host material bis(9,9'-spirobifluoren-2-yl) ketone and the guest material (dopant) $Ir(ppy)_3$. Furthermore, OLEDs of various designs are described, with the guest material (dopant) in each case being $Ir(ppy)_3$. OLEDs having the following structure are produced analogously to the general process mentioned above:

| | |
|---|---|
| Hole-injection layer (HIL) | 20 nm of 2,2',7,7'-tetrakis(di-para-tolyl-amino)spiro-9,9'-bifluorene |
| Hole-transport layer (HTL) | 20 nm of NPB (N-naphthyl-N-phenyl-4,4'-diaminobiphenyl) or amine 1 as comparison or compound 1. |

-continued

| | |
|---|---|
| Emission layer (EML) | 40 nm of host: spiro-ketone (SK) (bis(9,9'-spirobifluoren-2-yl) ketone) as comparison or compound 2. Dopant: $Ir(ppy)_3$ (10% doping, vapour-deposited; synthesised in accordance with WO 04/085449). |
| Electron conductor (ETL) | 20 nm of $AlQ_3$ (tris(quinolinato)aluminium(III)) as comparison or compound 3. |
| Cathode | 1 nm of LiF, 150 nm of Al on top. |

For reasons of clarity, the structures of $Ir(ppy)_3$, spiro-ketone (SK) and amine 1 are depicted below. Amine 1 here is a comparative compound in accordance with the closest prior art (JP 2005/085599):

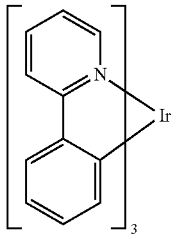

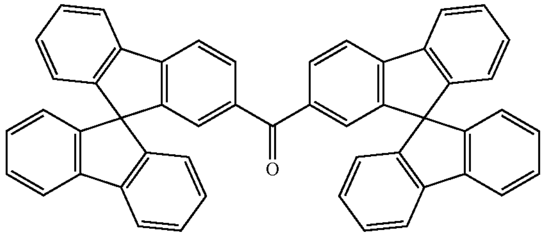

spiro-ketone (SK)

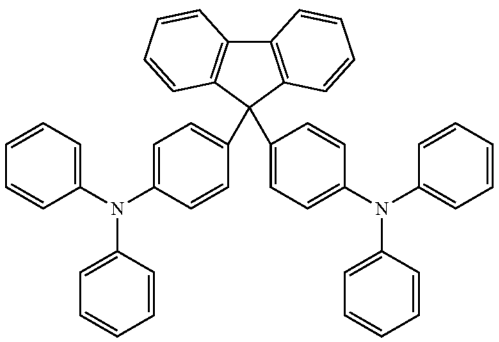

amine 1

Compounds 1 to 7 according to the invention are depicted below:

compound 1

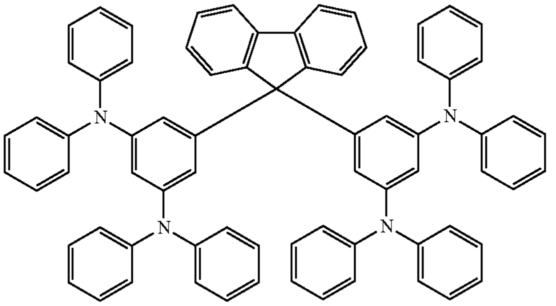

compound 2

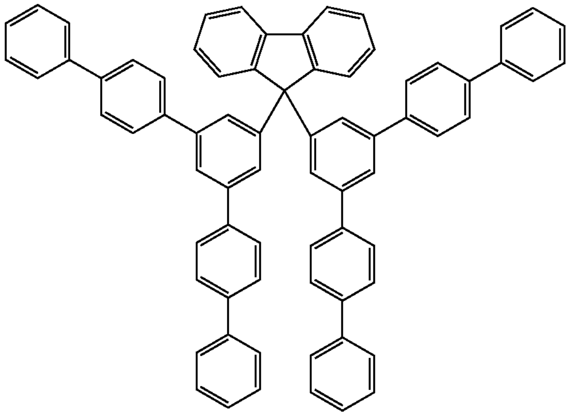

compound 3

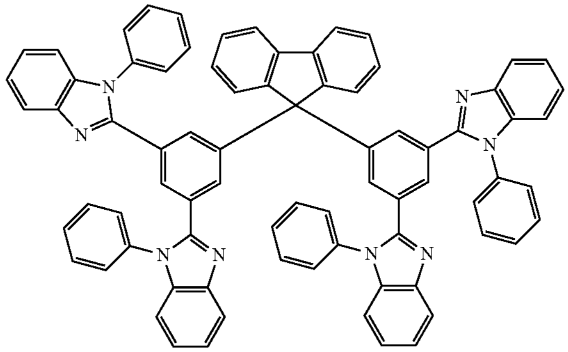

compound 4

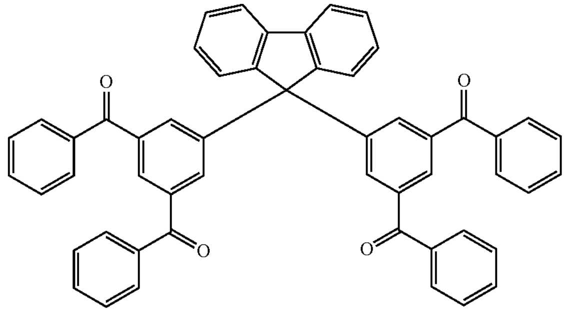

-continued compound 5

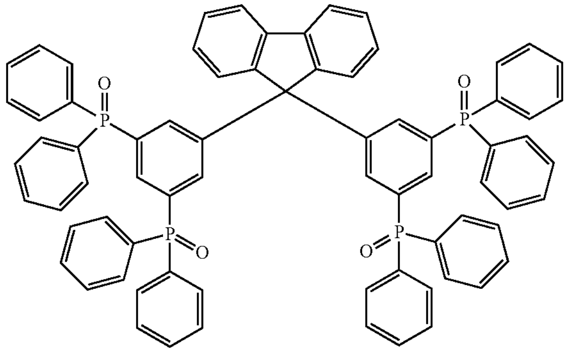

compound 6

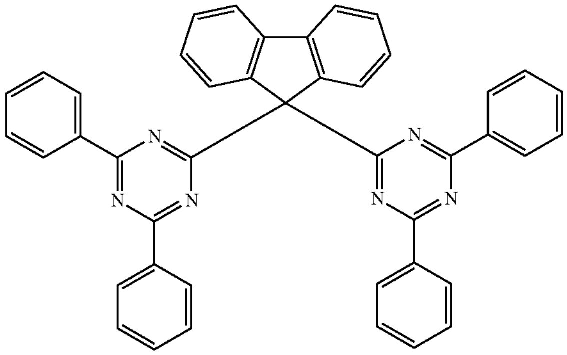

compound 7

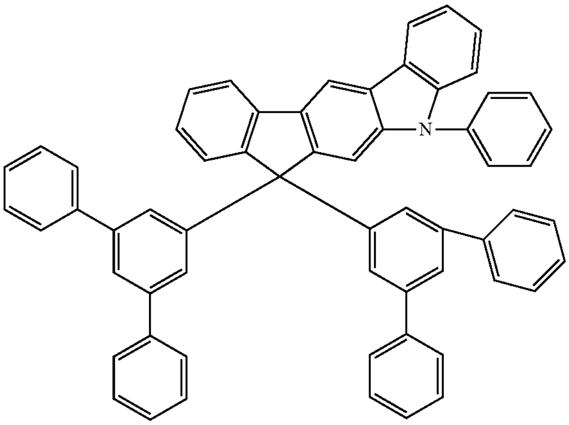

These still unoptimised OLEDs are characterised by standard methods; for this purpose, the electroluminescence spectra, the efficiency (measured in cd/A) as a function of the luminance, calculated from current-voltage-luminance characteristic lines (IUL characteristic lines), and the lifetime are determined.

With OLEDs produced in accordance with the structure described above and the materials as comparative experiment with NPB as hole-transport material, a maximum efficiency of about 30 cd/A with colour coordinates of CIE: x=0.38, y=0.57 is typically obtained under the conditions described above. For the reference luminous density of 1000 $cd/m^2$, voltages of 4.4 V are required. The lifetime is about 7700 h at an initial luminous density of 1000 $cd/m^2$ (see Table 1, Example 26). With amine 1 as hole-transport material in an otherwise identical device structure (see Table 1, Example 27), a better maximum efficiency in the region of 41 cd/A is obtained, but voltages of 5.3 V are required for the reference luminous density of 1000 cd/$m^2$, and the lifetime is only about 5600 h.

By contrast, OLEDs according to the invention produced using the electron-blocking material according to the invention (compound 1) exhibit a significantly increased maximum efficiency of 47 cd/A with colour coordinates of CIE: x=0.38, y=0.58, where the requisite voltage for the reference luminous density of 1000 cd/$m^2$ is 4.4 V (see Table 1, Example 28). The lifetime of 7400 h at an initial luminous density of 1000 cd/$m^2$ is comparable with Comparative Example 26 (see Table 1, Example 28). In contrast to the comparative experiment, OLEDs according to the invention produced using the host material (compound 2) instead of the spiroketone with an otherwise identical structure exhibit a maximum efficiency of 35 cd/A with improved colour coordinates of CIE: x=0.31, y=0.62, where the requisite voltage for the reference luminous density of 1000 cd/$m^2$ is 5.2 V (see Table 1, Example 29). The lifetime of 6900 h at an initial luminous density of 1000 cd/$m^2$ is comparable to that on use of the spiro-ketone (see Table 1, Example 29).

If compound 1 is employed as electron-blocking material and compound 3 as electron-transport material instead of Alq, maximum efficiencies of 54 cd/A with colour coordinates of CIE: x=0.37, y=0.59 are obtained, where the requisite voltage for the reference luminous density of 1000 cd/$m^2$ is 4.1 V (see Table 1, Example 30). The lifetime of 7200 h at an initial luminous density of 1000 cd/$m^2$ is comparable, and the voltage of 4.1 V is lower than with the reference material Alq (see Table 1, Example 22).

If compounds 4, 5 and 7 according to the invention are employed as matrix material, very good efficiencies are obtained in combination with good lifetimes. Compound 6 is suitable, inter alia, as electron conductor, which gives good efficiencies and lifetimes at low voltages.

TABLE 1

Device results with compounds according to the invention with $Ir(ppy)_3$ as dopant

| Ex. | HTL/EBL 20 nm | EML 40 nm | ETL 20 nm | Max. eff. [cd/A] | Voltage [V] at 1000 cd/$m^2$ | CIE (x, y) | Lifetime [h], initial luminance 1000 cd/$m^2$ |
|---|---|---|---|---|---|---|---|
| 26 comp. | NPB | SK: $Ir(ppy)_3$ | Alq | 30 | 4.4 | 0.38/0.57 | 7700 |
| 27 comp. | Amine 1 | SK: $Ir(ppy)_3$ | Alq | 41 | 5.3 | 0.38/0.58 | 5600 |
| 28 | Comp. 1 | SK: $Ir(ppy)_3$ | Alq | 47 | 4.4 | 0.38/0.58 | 7400 |
| 29 | NPB | Comp. 2: $Ir(ppy)_3$ | Alq | 35 | 5.2 | 0.31/0.62 | 6900 |
| 30 | Comp. 1 | SK: $Ir(ppy)_3$ | Comp. 3 | 54 | 4.1 | 0.37/0.59 | 7200 |
| 31 | NPB | Comp. 4: $Ir(ppy)_3$ | Alq | 41 | 5.2 | 0.36/0.59 | 7000 |
| 32 | Comp. 1 | Comp. 4: $Ir(ppy)_3$ | Alq | 57 | 4.3 | 0.36/0.59 | 7800 |
| 33 | Comp. 1 | Comp. 5: $Ir(ppy)_3$ | Alq | 61 | 4.5 | 0.36/0.59 | 7200 |
| 34 | Comp. 1 | SK: $Ir(ppy)_3$ | Comp. 6 | 52 | 4.0 | 0.37/0.60 | 7300 |
| 35 | Comp. 1 | Comp. 7: $Ir(ppy)_3$ | Alq | 53 | 3.9 | 0.38/0.59 | 8100 |

The invention claimed is:

1. A compound of formula (1)

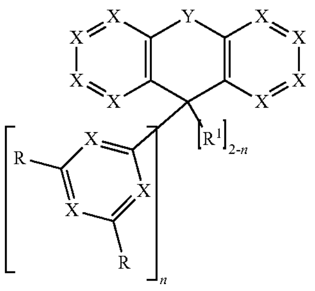

formula (1)

wherein

X is on each occurrence, identically or differently, $CR^1$ or N, wherein a maximum of 3 X groups in each ring are N or wherein two directly adjacent X groups are a unit of formula (7)

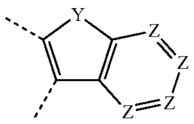

formula (7)

wherein the dashed bonds indicate the link of the unit of formula (7) to adjacent C or N atoms;

Y is on each occurrence, identically or differently, a single bond or $BR^1$, $C(R^1)_2$, C(=O), C(=$NR^1$), C(=$C(R^1)_2$), $Si(R^1)_2$, $P(=O)R^1$, O, S, $S(=O)$, $S(=O)_2$, $C(R^1)_2-C(R^1)_2$, $C(R^1)_2-NR^1$, or $CR^1=CR^1$;

is on each occurrence, identically or differently, $CR^1$ or N, wherein a maximum of two Z in each ring are N;

R is on each occurrence, identically or differently, $NAr_2$, $C(=O)Ar$, $P(=O)Ar_2$, or an aromatic or heteroaromatic ring system having from 5 to 30 aromatic ring atoms and is optionally substituted by one or more non-aromatic radicals $R^1$;

Ar is on each occurrence, identically or differently, an aromatic or heteroaromatic ring system having from 5 to 30 aromatic ring atoms and is optionally substituted by one or more non-aromatic radicals $R^1$; wherein two Ar bonded to the same nitrogen or phosphorus atom are optionally linked to one another by a single bond or a bridge selected from the group consisting of $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$, and $P(=O)R^2$;

$R^1$ is on each occurrence, identically or differently, H, F, Cl, Br, I, CHO, $N(R^2)_2$, $N(Ar)_2$, $C(=O)Ar$, $P(=O)(Ar)_2$, $S(=O)Ar$, $S(=O)_2Ar$, $CR^2=CR^2Ar$, CN, $NO_2$, $Si(R^2)_3$, $B(OR^2)_2$, $B(R^2)_2$, $B(N(R^2)_2)_2$, $OSO_2R^2$, a straight-chain alkyl, alkenyl, alkynyl, alkoxy, or thioalkoxy group having from 1 to 40 C atoms or a branched or cyclic alkyl, alkenyl, alkynyl, alkoxy, or thioalkoxy group having from 3 to 40 C atoms, wherein said straight-chain, branched, or cyclic alkyl, alkenyl, alkynyl, alkoxy, or thioalkoxy group is optionally substituted by one or more radicals $R^2$, wherein one or more non-adjacent $CH_2$ groups in said straight-chain, branched, or cyclic alkyl, alkenyl, alkynyl, alkoxy, or thioalkoxy group is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $CONR^2$, and wherein one or more H atoms in said straight-chain, branched, or cyclic alkyl, alkenyl, alkynyl, alkoxy, or thio-alkoxy group is optionally replaced by F, Cl, Br, I, CN, or $NO_2$, an aromatic or heteroaromatic ring system having from 5 to 60 aromatic ring atoms and is optionally substituted by one or more radicals $R^2$, or an aryloxy or heteroaryloxy group haying from 5 to 60 aromatic ring atoms and is optionally substituted by one or more radicals $R^2$, or a combination of these systems; and wherein two or more adjacent substituents $R^1$ optionally define a mono- or polycyclic, aliphatic or aromatic ring system with one another;

$R^2$ is on each occurrence, identically or differently, H, D, or an aliphatic, aromatic, and/or heteroaromatic hydrocarbon radical having from 1 to 20 C atoms, wherein H atoms of said aliphatic, aromatic, and/or heteroaromatic hydrocarbon radical is optionally replaced by F; and wherein two or more adjacent substituents $R^2$ optionally define a mono- or polycyclic, aliphatic, or aromatic ring system with one another;

n is 1 or 2; and with the proviso that said compound of formula (1) does not include the following compound:

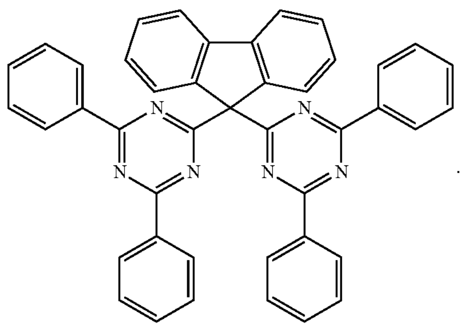 [SMILES: c1ccc(-c2nc(-c3ccccc3)nc(C3(c4nc(-c5ccccc5)nc(-c5ccccc5)n4)c4ccccc4-c4ccccc43)n2)cc1 ; "."]

2. The compound of claim 1, wherein said compound is a compound of formula (2), (3), (8), (9), (10), or (11):

formula (2)

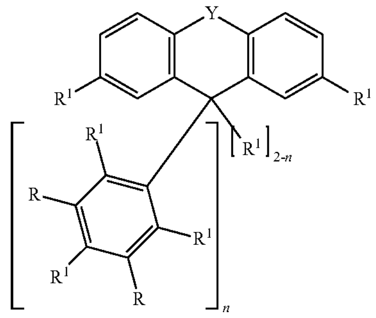

formula (3)

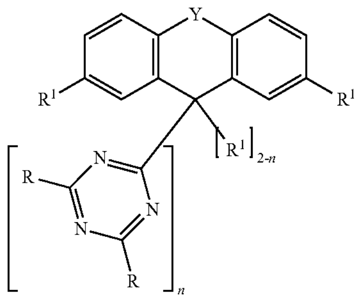

formula (8)

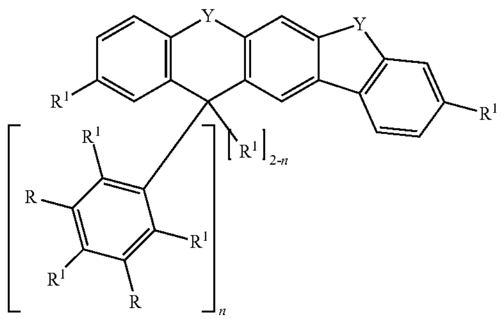

-continued
formula (9)
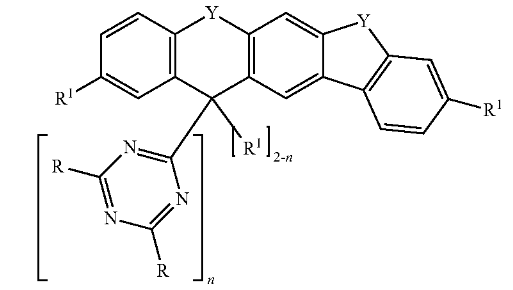
formula (10)
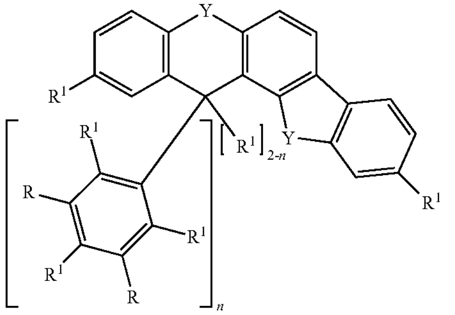
formula (11)
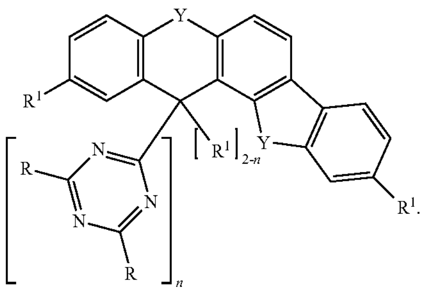
3. The compound of claim 1, wherein Y is a single bond, $C(R^1)_2$, O, or $NR^1$.
4. The compound of claim 1, wherein said compound is a compound of formula (2a), (3a), (8a), (8b), (9a), (9b), (10a), (10b), (11a), or (11b):
formula (2a)
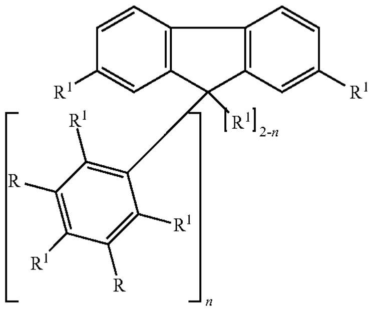
-continued
formula (3a)
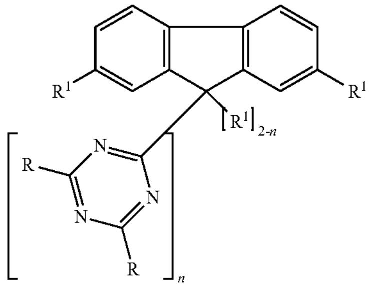
formula (8a)
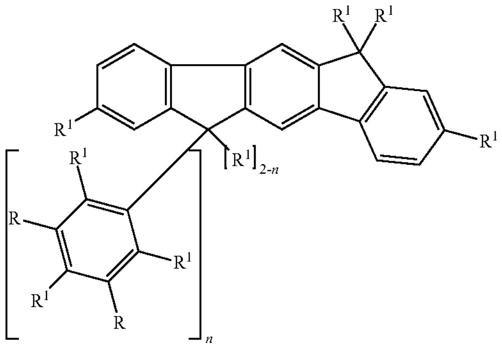
formula (8b)
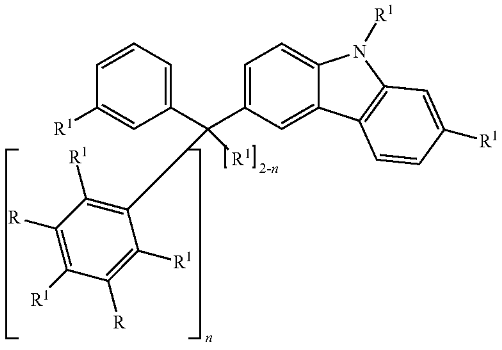
formula (9a)
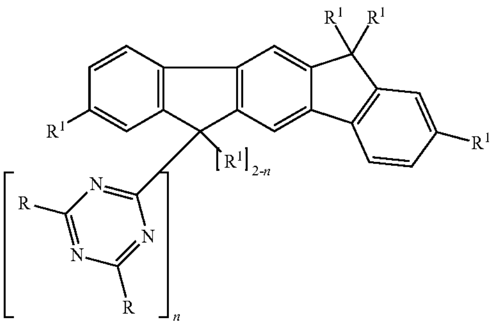

-continued
formula (9b)
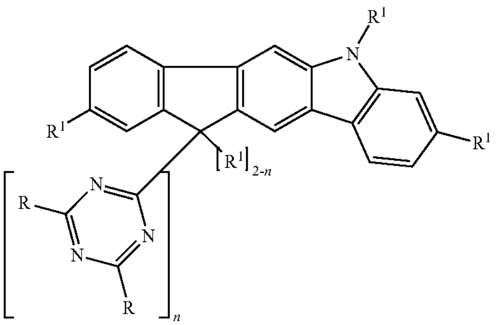
formula (10a)
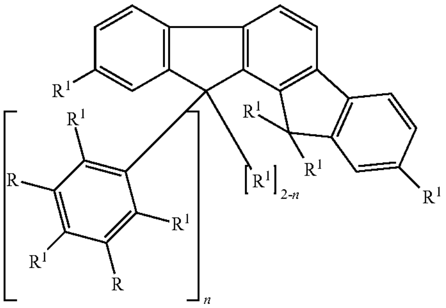
formula (10b)
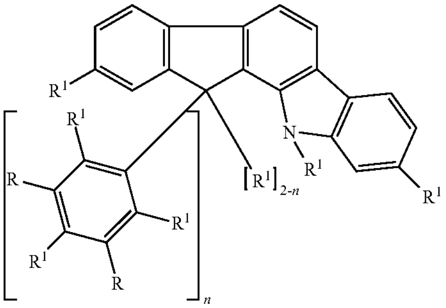
formula (11a)
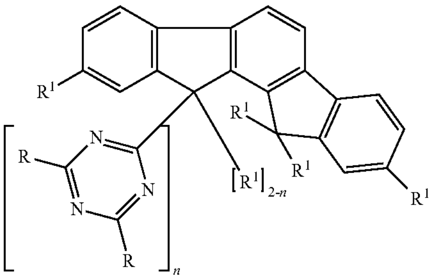
formula (11b)
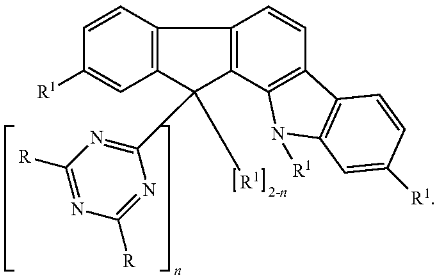
5. The compound of claim 1, wherein said compound is a compound of formula (4a) or (4b):
formula (4a)
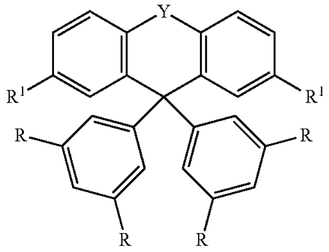
formula (4b)
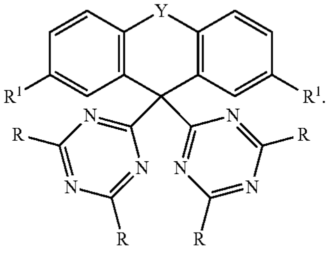
6. The compound of claim 1, wherein said compound is a compound of formula (4c), (4d), (8c), (8d), (9c), (9d), (10c), (10d), (11c), or (11d):
formula (4c)
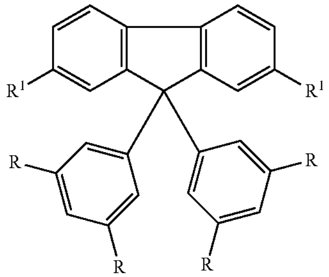
formula (4d)
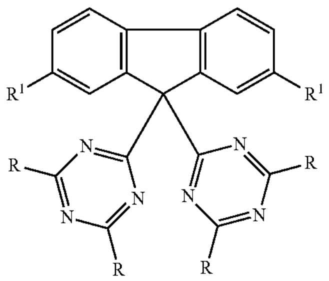

-continued
formula (8c)
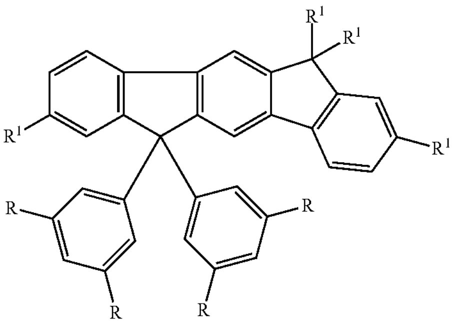
formula (8d)
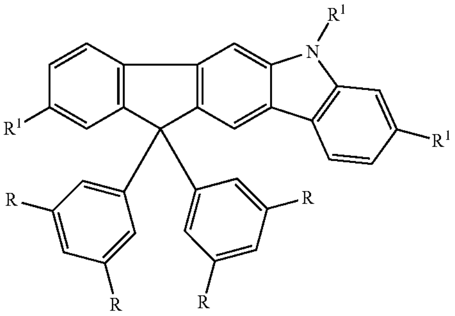
formula (9c)
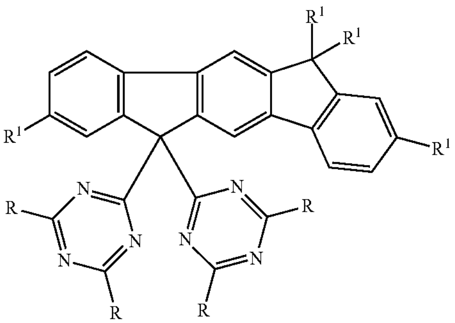
formula (9d)
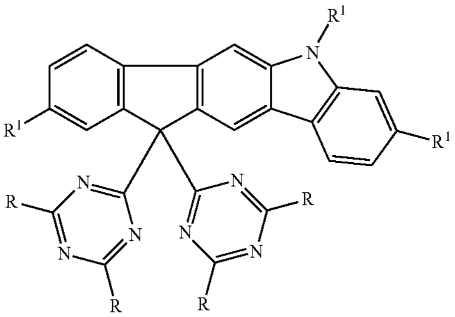
formula (10c)
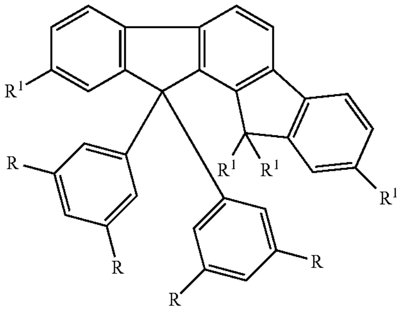
formula (10d)
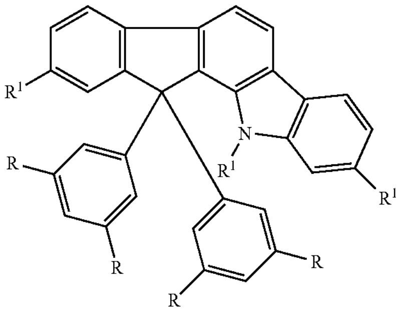
formula (11c)
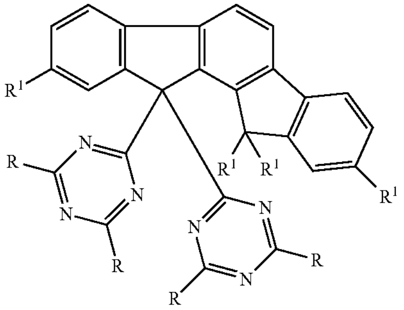
formula (11d)
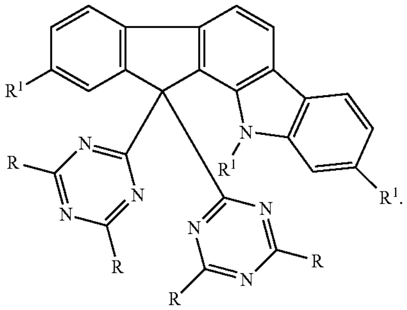

7. The compound of claim 1, wherein R or $R^1$ is $N(Ar)_2$, wherein $N(Ar)_2$ is a group of formula (5) or formula (6):

formula (5)

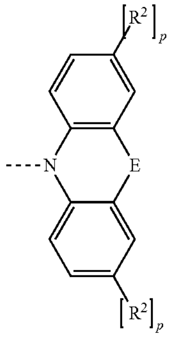

formula (6)

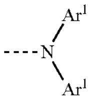

wherein is on each occurrence, identically or differently, H, D, or an aliphatic, aromatic, and/or heteroaromatic hydrocarbon radical having from 1 to 20 C atoms, wherein H atoms of said aliphatic, aromatic, and/or heteroaromatic hydrocarbon radical is optionally replaced by F; and wherein two or more adjacent substituents $R^2$ optionally define a mono- or polycyclic, aliphatic, or aromatic ring system with one another;

E is a single bond, O, S, $N(R^2)$, or $C(R^2)$;

$Ar^1$ is, identically or differently on each occurrence, an aromatic or heteroaromatic ring system having from 5 to 20 aromatic ring atoms or a triarylamine group having from 15 to 30 aromatic ring atoms, wherein said aromatic or heteroaromatic ring system or said triarylamine group is optionally substituted by one or more radicals $R^2$;

p is on each occurrence, identically or differently, 0 or 1;

and/or wherein R is an aromatic or heteroaromatic ring system selected from the group consisting of phenyl, 1-naphthyl, 2-naphthyl, anthracenyl, phenylanthracenyl, 1-naphthylanthracenyl, 2-naphthylanthracenyl, binaphthyl, pyrenyl, fluoranthenyl, 2-benz-anthracenyl, 3-benzanthracenyl, 4-benzanthracenyl, 5-benzanthracenyl, 6-benzanthracenyl, 7-benzanthracenyl, N-benzimidazolyl, phenyl-N-benzimidazolyl, N-phenylbenzimidazolyl, and phenyl-N-phenylbenzimidazolyl.

8. A process for preparing the compound of claim 1, comprising (1) reacting bis(3,5-dibromo)benzophenone with a substituted or unsubstituted 2-lithiobiphenyl, 2-lithiodiphenyl ether, 2-lithiodiphenyl thioether, 2-(2-lithiophenyl)-2-phenyl-1,3-dioxolane, 2-lithiophenyldiphenylamine, or a corresponding Grignard compound to give the corresponding triarylmethanols, (2) cyclizing said triarylmethanols under acidic conditions, and (3) optionally followed by further reaction of the bromine groups.

9. A dimer, trimer, tetramer, pentamer, oligomer, polymer, or den-drimer comprising one or more compounds of claim 1, wherein one or more radicals $R^1$ or $R^2$ are bonds between the compounds of formula (1) in said dimer, trimer, tetramer, or pentamer or are bonds from the compound of formula (1) to said polymer, oligomer, or dendrimer, or wherein this bonding takes place via substituents on the R groups.

10. A mixture comprising at least one compound of claim 1 and at least one further compound.

11. A solution comprising at least one compound of claim 1 and at least one organic solvent.

12. An electronic device comprising at least one compound of claim 1.

13. The electronic device of claim 12, wherein said electronic device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic laser diodes, or organic photo receptors.

14. An organic electroluminescent device comprising the compound of claim 1 as matrix material for fluorescent or phosphorescent compounds.

15. The electronic device of claim 12, wherein Y is C═O, P(═O), SO, or $SO_2$ and/or one or more groups R and/or $R^1$ is a heteroaryl group which is an electron-deficient heterocycle or is C(═O)Ar, S(═O)Ar, $S(=O)_2Ar$, or $P(=O)Ar_2$ and the compound of claim 1 is employed as an electron-transport material or as a hole-blocking material.

16. The electronic device of claim 12, wherein one or more groups R and/or $R^1$ is $N(Ar)_2$ and the compound of claim 1 is employed as hole transport material or as hole injection material or as electron-Hocking material or as exciton-blocking material.

17. The organic electroluminescent device of claim 14, wherein Y is C═O, P(═O), SO, or $SO_2$ and/or at least one of groups R and/or $R^1$ is a heteroaryl group which is an electron-deficient heterocycle, C(═O)Ar, $P(=O)Ar_2$, S(═O)Ar, or $S(O)_2Ar$.

* * * * *

UNITED STATES PATENT AND TRADEMARK OFFICE

CERTIFICATE OF CORRECTION

PATENT NO. : 8,361,638 B2
APPLICATION NO. : 12/936644
DATED : January 29, 2013
INVENTOR(S) : Philipp Stoessel et al.

It is certified that error appears in the above-identified patent and that said Letters Patent is hereby corrected as shown below:

In the Claims:

In Claim 1, in column 169, lines 1 and 2, "$Si(R^1)_2$, $P(=O)R^1$, O, S, S(=O), $S(=O)_2$, $C(R^1)_2$-$C(R^1)_2$, $C(R^1)_2$-$NR^1$, or $CR^1$=$CR^1$;" should read "$Si(R^1)_2$, $NR^1$, $PR^1$, $P(=O)R^1$, O, S, S(=O), $S(=O)_2$, $C(R^1)_2$-$C(R^1)_2$, $C(R^1)_2$-$NR^1$, or $CR^1$=$CR^1$;"

In Claim 1, in column 169, line 3, "is on each occurrence, identically or differently, $CR^1$ or N, wherein a maximum of two Z in each ring are N," should read "Z is on each occurrence, identically or differently, $CR^1$ or N, wherein a maximum of two Z in each ring are N,"

Signed and Sealed this
Third Day of June, 2014

Michelle K. Lee
*Deputy Director of the United States Patent and Trademark Office*